(12) United States Patent
Chishti et al.

(10) Patent No.: US 7,134,874 B2
(45) Date of Patent: Nov. 14, 2006

(54) COMPUTER AUTOMATED DEVELOPMENT OF AN ORTHODONTIC TREATMENT PLAN AND APPLIANCE

(75) Inventors: Muhammad Chishti, Sunnyvale, CA (US); Brian Freyburger, San Francisco, CA (US); Kelsey Wirth, Palo Alto, CA (US); Andrew Beers, Redwood City, CA (US); Huafeng Wen, Redwood Shores, CA (US); Phillips Alexander Benton, Mountain View, CA (US); Timothy N. Jones, Mountain View, CA (US); Ross J. Miller, Sunnyvale, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

(21) Appl. No.: 10/718,779

(22) Filed: Nov. 20, 2003

(65) Prior Publication Data
US 2004/0110110 A1    Jun. 10, 2004

Related U.S. Application Data

(63) Continuation of application No. 09/686,190, filed on Oct. 10, 2000, now abandoned, which is a continuation of application No. 09/169,276, filed on Oct. 8, 1998, now abandoned, which is a continuation-in-part of application No. PCT/US98/12681, filed on Jun. 19, 1998.

(60) Provisional application No. 60/050,342, filed on Jun. 20, 1997.

(51) Int. Cl.
*A61C 3/00*    (2006.01)

(52) U.S. Cl. ............................. 433/24; 433/6

(58) Field of Classification Search .................. 433/24, 433/6, 213
See application file for complete search history.

(56) References Cited

U.S. PATENT DOCUMENTS

| | | | |
|---|---|---|---|
| 2,467,432 A | 4/1949 | Kesling | |
| 3,660,900 A | 5/1972 | Andrews | |
| 3,860,803 A | 1/1975 | Levine | |
| 3,916,526 A | 11/1975 | Schudy | |
| 3,950,851 A | 4/1976 | Bergersen | |
| 4,014,096 A | 3/1977 | Dellinger | |
| 4,195,046 A | 3/1980 | Kesling | |
| 4,324,546 A | 4/1982 | Heitlinger et al. | |
| 4,348,178 A | 9/1982 | Kurz | |
| 4,478,580 A | 10/1984 | Barrut | |
| 4,504,225 A | 3/1985 | Yoshii | |
| 4,505,673 A | 3/1985 | Yoshii | |
| 4,575,805 A | 3/1986 | Moermann et al. | |

(Continued)

FOREIGN PATENT DOCUMENTS

EP    091876 A1    10/1983

(Continued)

OTHER PUBLICATIONS

Alexander et al., "The DigiGraph Work Station Part 2, Clinical Management," *JCO* (Jul. 1990), pp. 402-407.

(Continued)

*Primary Examiner*—John J Wilson
(74) *Attorney, Agent, or Firm*—Townsend and Townsend and Crew LLP

(57) ABSTRACT

A computer is used to create a plan for repositioning an orthodontic patient's teeth. The computer receives an initial digital data set representing the patient's teeth at their initial positions and a final digital data set representing the teeth at their final positions. The computer then uses the data sets to generate treatment paths along which the teeth will move from the initial positions to the final positions.

99 Claims, 28 Drawing Sheets

U.S. PATENT DOCUMENTS

| | | | |
|---|---|---|---|
| 4,611,288 | A | 9/1986 | Duret et al. |
| 4,656,860 | A | 4/1987 | Orthuber et al. |
| 4,663,720 | A | 5/1987 | Duret et al. |
| 4,742,464 | A | 5/1988 | Duret et al. |
| 4,755,139 | A | 7/1988 | Abbatte et al. |
| 4,763,791 | A | 8/1988 | Halverson et al. |
| 4,793,803 | A | 12/1988 | Martz |
| 4,798,534 | A | 1/1989 | Breads |
| 4,837,732 | A | 6/1989 | Brandestini et al. |
| 4,850,864 | A | 7/1989 | Diamond |
| 4,856,991 | A | 8/1989 | Breads et al. |
| 4,936,862 | A | 6/1990 | Walker et al. |
| 4,937,928 | A | 7/1990 | van der Zel |
| 4,964,770 | A | 10/1990 | Steinbichler et al. |
| 4,975,052 | A | 12/1990 | Spencer et al. |
| 5,011,405 | A | 4/1991 | Lemchen |
| 5,017,133 | A | 5/1991 | Miura |
| 5,027,281 | A | 6/1991 | Rekow et al. |
| 5,035,613 | A | 7/1991 | Breads et al. |
| 5,055,039 | A | 10/1991 | Abbatte et al. |
| 5,059,118 | A | 10/1991 | Breads et al. |
| 5,100,316 | A | 3/1992 | Wildman |
| 5,121,333 | A | 6/1992 | Riley et al. |
| 5,128,870 | A | 7/1992 | Erdman et al. |
| 5,131,843 | A | 7/1992 | Hilgers et al. |
| 5,131,844 | A | 7/1992 | Marinaccio et al. |
| 5,139,419 | A | 8/1992 | Andreiko et al. |
| 5,184,306 | A | 2/1993 | Erdman et al. |
| 5,186,623 | A | 2/1993 | Breads et al. |
| 5,257,203 | A | 10/1993 | Riley et al. |
| 5,273,429 | A | 12/1993 | Rekow et al. |
| 5,278,756 | A | 1/1994 | Lemchen et al. |
| 5,338,198 | A | 8/1994 | Wu et al. |
| 5,340,309 | A | 8/1994 | Robertson |
| 5,342,202 | A | 8/1994 | Deshayes |
| 5,368,478 | A | 11/1994 | Andreiko et al. |
| 5,382,164 | A | 1/1995 | Stern |
| 5,395,238 | A | 3/1995 | Andreiko et al. |
| 5,431,562 | A | 7/1995 | Andreiko et al. |
| 5,440,496 | A | 8/1995 | Andersson et al. |
| 5,447,432 | A | 9/1995 | Andreiko et al. |
| 5,452,219 | A | 9/1995 | Dehoff et al. |
| 5,454,717 | A | 10/1995 | Andreiko et al. |
| 5,456,600 | A | 10/1995 | Andreiko et al. |
| 5,474,448 | A | 12/1995 | Andreiko et al. |
| RE35,169 | E | 3/1996 | Lemchen et al. |
| 5,518,397 | A | 5/1996 | Andreiko et al. |
| 5,528,735 | A | 6/1996 | Strasnick et al. |
| 5,533,895 | A | 7/1996 | Andreiko et al. |
| 5,542,842 | A | 8/1996 | Andreiko et al. |
| 5,549,476 | A | 8/1996 | Stern |
| 5,587,912 | A | 12/1996 | Andersson et al. |
| 5,605,459 | A | 2/1997 | Kuroda et al. |
| 5,607,305 | A | 3/1997 | Andersson et al. |
| 5,621,648 | A | 4/1997 | Crump |
| 5,645,421 | A | 7/1997 | Slootsky |
| 5,655,653 | A | 8/1997 | Chester |
| 5,683,243 | A | 11/1997 | Andreiko et al. |
| 5,733,126 | A | 3/1998 | Andersson et al. |
| 5,740,267 | A | 4/1998 | Echerer et al. |
| 5,823,778 | A | 10/1998 | Schmitt et al. |
| 5,879,158 | A | 3/1999 | Doyle et al. |
| 5,975,893 | A | 11/1999 | Chishti et al. |
| 6,068,482 | A | 5/2000 | Snow |
| 6,217,334 | B1 | 4/2001 | Hultgren |
| 6,350,120 | B1 | 2/2002 | Sachdeva et al. |

FOREIGN PATENT DOCUMENTS

| | | |
|---|---|---|
| EP | 299490 A2 | 1/1989 |
| EP | 376873 A2 | 7/1990 |
| EP | 490848 B1 | 6/1992 |
| EP | 774933 B1 | 5/1997 |
| EP | 541500 A1 | 6/1998 |
| EP | 731673 B1 | 9/1998 |
| FR | 2 369 828 | 6/1978 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 | 5/1994 |
| WO | WO 94/10935 A1 | 5/1994 |
| WO | WO 98/32394 | 7/1996 |
| WO | WO 98/44865 A1 | 10/1998 |
| WO | WO 98/58596 A1 | 12/1998 |

OTHER PUBLICATIONS

Altschuler et al., "Laser Electro-Optic System for Rapid Three-Dimensional (3D) Topographic Mapping of Surfaces," *Optical Engineering*, vol. 20(6) (1981), pp. 953-961.

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," Program and Abstracts of Papers, Feb. 1975, *Journal of Dental Research*, vol. 54, IADR Abstracts 1979, 2 pages total.

Altschuler, "3D Mapping of Maxillo-Facial Prosthesis," AADR Abstract #607, 1980, 2 pages total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A stereophotogrammetric system for the detection of prosthesis loosening in total hip arthroplasty, Applications of Human Biostereometrics (NATO)," Proceedings of the Society of Photo-Optical Instrumentation Engineers, vol. 166, Jul. 9-13, 1978, pp. 112-123.

Baumrind et al., Mapping the Skull in 3-D, Reprinted from The Journal, *California Dental Association*, vol. 48, No. 2 (1972 Fall Issue) 11 pages total.

Baumrind et al., "Seminars in Orthodontics," *Seminars in Orthodontics*, vol. 7, No. 4 (Dec. 2001), p. 222.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. 1-25.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized diagnosis in Orthodontics for Epidemiological Studies" (progress report), Abstracts of Papers, *Journal of Dental Research*; vol. 71, Special Issue Mar. 1-14, 1992, pp. 28-36.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized analysis of occlusion in the postcanine dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Brandestini et al., "Computer Machined Ceramic Inlays: In Vitro Marginal Adaptation," *Journal of Dental Research*, vol. 64/Special Issue/Abstracts, IADR/AADR Abstracts 1985, 1 page total.

Brook et al., An Image Analysis System for the Determination of Tooth Dimensions from Study Casts: Comparison with Manual Measurements of Mesio-distal Diameter, Abstract of Papers, 1985, Dept. of Children's Dentistry and Orthodontics, *J Dent Res.*, Mar. 1986, pp. 428-431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7 , Jul. 1979; (Part 2) vol. 8, No. 8 pp. 539-551, Aug. 1979.

Burstone et al., "Precision adjustment of the transpalatal lingual arch: Computer arch form predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the gnathologic setup and positioner" *J. Clin. Orthod.*, 14:121-133, 1980.

Cottingham, "Gnathologic clear plastic positioner" *Am. J. Orthod.*, 55:23-31, 1969.

Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From The Front Desk To The Operatory, *Canadian Dental Journal*, vol. 54(9), , (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting malaligned mandibular incisors with removable retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol .7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

DeFranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 3 pages total.

DenTrac Corporation, Dentrac document, pp. 4-13.

Duret et al, "CAD-CAM in Dentistry," *Journal of the American Dental Association*, vol. 117 (Nov. 1988), pp. 715-720.

Duret et al., "CAD/CAM imaging in dentistry," *Current Opinion in Dentistry*, vol. 1 (1991), pp. 150-154.

Duret, "The Dental CAD/CAM, General Description of the Project," *Hennson International Product Brochure*, Jan. 1986., 18 pages total.

Duret, "Vers une prosthese informatisee," (English translation also attached), *Tonus*, vol. 75, (Nov. 15, 1985), pp. 55-57.

Economides, "The Microcomputer in the Orthodontic Office," *JCO*, (Nov. 1979), pp. 767-772.

Elsasser, "Some observations on the history and uses of the Kesling positioner" *Am. J. Orthod.*, 36:368-374, 1950.

Faber et al., "Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery," Abstracts of Papers, *Journal of Dental Research*, vol. 70 (1987), pp. 754-760.

Gim-Alldent Deutschland, "Das DUX System: Die Technik" 4 pages total.

Grayson, "New Methods for Three Dimensional Analysis of Craniofacial Deformity," Symposium: Computerized Facial Imaging in Oral and Maxilofacial Surgery, AAOMS Sep. 13, 1990, 3 pages total.

Guess et al., "Computer Treatment Estimates in Orthodontics and Orthognathic Surgery," *JCO*, (Apr. 1989), pp. 262-280.

Heaven et al., "Computer-base Image Analysis of Artificial Root Surface Caries," "Automated Identification of Landmarks in Cephalometric Radiographs," Abstracts of Papers, *Journal of Dental Research*, vol. 67, Mar. 9-13, 1988, 2 pages total.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

Inside the ADA, *Journal Of The American Dental Assoc.*, vol. 118 (Mar. 1989) 9 pages total.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The problem, electronic data transmission and the law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case reports on tooth positioners using LTV vinyl silicone rubber" J. Nihon University School of Dentistry, 26(1):11-29, 1984.

Kamada et al., "Construction of tooth positioners with LTV vinyl silicone rubber and some case reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.* , vol. 63, No. 11 (Nov. 1984), pp. 1298-1301.

Kesling, "Coordinating the predetermined pattern and tooth positioner with conventional treatment" *Am. J. Orthod. Oral. Surg.*, 32:285-293, 1946.

Kesling, "The philosophy of the tooth positioning appliance" *Am. J. Orthod. Oral. Surg.*, 31(6):297-304, 1945.

Kleeman et al., "The speed positioner" *J. Clin. Orthod.*, 30:673-680, 1996.

Kuroda et al., "Three-dimensional dental cast analyzing system using laser scanning" *Am. J. Orhtod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

McNamara et al., *Orthodontic and Orthopedic Treatment in the Mixed Dentition*, Needham Press, Jan. 1993. pp. 347-353.

McNamara et al., "Invisible Retainers", *J. Clinical Orthodontics*, (Aug. 1985) pp. 570-578.

Moermann et al., "Computer Machined Adhesive Porcelain Inlays: Margin Adaptation after Fatigue Stress," IADR Abstract 339, *Journal of Dental Research*, vol. 66(a) (1987), p. 339.

Mörmann et al., "Marginal Adaptation von adhasiven Porzellaninlays in vitro," *Schwizerische Monatsshrift fur Zahnmedizin*, vol. 85 (1985), p. 1118-1129.

Mörmann et al., "Marginate Adaptation von adhäsuven Porzellaninlays in vitro," Separatdruck aus: Schweiz. Mschr. Zahnmed. 95: 1118, 1985.

Nahoum, "The vacuum formed dental contour appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20. 22-23, 54.

Nishiyama et al., "A new construction of tooth repositioner by LTV vinyl silicone rubber" J. Nihon University School of Dentistry, 19(2):93-102, 1977.

Pinkham, "'Foolish' Concept Propels Technology," *Dentist*, Jan./Feb. 1989, 3 pages total.

Pinkham, "Inventor's CAD/CAM may transform dentistry," *Dentist*, Sep. 1990, 3 pages total.

Ponitz, Invisible Retainers, 59 *Am. J. Orthodontics*, Mar. 1971, pp. 266-272.

Procera Research Projects, *PROCERA Research Projects 1993*—Abstract Collection, 1993, pp. 3-28.

Rekow, "A Review of the Developments in Dental CAD/CAM Systems," (contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, Feasibility of an Automated System for Production of "Dental Restorations," PhD Thesis, Univ. of Minnesota, Nov. 1988, 244 pages total.

Richmond et al., Research Reports, "The development of a 3D Cast Analysis System," *British Journal of Orthodontics*, pp. 53-54.

Richmond, "Recording the dental cast in three dimensions," *Am. J. Orthod. Dentofac. Orthop.*, vol. 92, No. 3, (Sep. 1987), pp. 199-206.

Rudge, "Dental arch analysis: arch form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computer Tomography in Maxillofacial Surgical Planning," *Arch Otolamgol Head Neck Surg.* vol. 114 (Apr. 1988), pp. 438-442.

Segu et al., "Computer-aided Cefalometry and New Mechanics in Orthodontics" (Article Summary in English, article in German), *Fortschr. Kieferorthop.* 44, 370-376 (Nr. 5), 1983.

Shilliday, "Minimizing finishing problems with the mini-positioner" *Am. J. Orthod.* 59:596-599, 1971.

Siemens, "CEREC—Computer-Reconstruction," High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 21 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden et al., Three-Dimensional Analysis of Dental Casts by Means of the Optocom, *J Dent Res*, Jul.-Aug. 1972, p. 1101.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Várady et al., "Reverse Engineering of Geometric Models—An Introduction," May 13, 1996, pp. 1-28.

Warunek et al., "Clinical use of silicone elastomer appliances" *JCO*, MH (10):694-700, 1989.

Warunek et al., "Physical and mechanical properties of elastomers in orthodontic positioners" *Am. J. Orthod. Dentofac. Orthop.*, 95:388-400, 1989.

Wells, "Application of the positioner appliance in orthodontic treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery, AAOMS, Sep. 13, 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical measurement of dental cast profile and application to analysis of three-dimensional tooth movement in orthodontics," *Frontiers in Med. and Biol. Eng'g*, vol. 1, No. 2 (1988), pp. 119-130.

Chiappone, Constructing the Gnathologic Setup and Positioner, J. Clin. Orthod., Vol. 14, No. 2, Feb. 1980, pp. 121-133.

Cottingham, Gnathologic Clear Plastic Positioner, Am. J. Orhod., vol. 55, No. 1, Jan. 1969, pp. 23-31.

Cureton, Correcting Malaligned Manibular Incisors with Removable Retainers, J. Clin. Orthod., vol. 30, No. 7, Jul. 1996, pp. 390-395.

Doyle, "Digital Dentistry" Computers Graphics World (Oct. 2000) pp. 50-52, 54.

Elsasser, Some Observations on the History and Uses of the Kesling Positioner, Am. J. Orhod., vol. 36, Jan.-Dec. 1950, pp. 368-374.

Kamada et al., Construction of Tooth Positioners with LTV Vinyl Silicone Rubber and Some Case Reports, J. Nihon University School of Dentistry, vol. 24, No. 1, Mar. 1982, pp. 127.

Kesling, Coordinating the Predetermined Pattern and Tooth Positioner with Conventional Treatment, Am. J. Orthod. Oral. Surg., vol. 32, No. 5, May 1946, pp. 285-293.

Kesling, the Philosophy of the Tooth Positioning Appliance, Am. J. Orthod. Oral. Surg., vol. 31, No. 6, Jun. 1945, pp. 297-304.

Kleeman et al., The Speed Positioner, J. Clin. Orthod., vol. 30, No. 12, Dec. 1996, pp. 673-680.

Kuroda et al., Three-dimensional Dental Cast Analyzing System Using Laser Scanning, Am. J. Orhtod. Dentofac. Orthop., vol. 110, No. 4, Oct. 1996, pp. 365-369.

Nishiyama et al., a New Construction of Tooth Positioner by Ltv Vinyl Silicone Rubber, J. Nihon Univ. School of Dentistry, vol. 19, No. 2, Jun. 1977, pp. 93-102.

Redmond et al., "Clinical Implications of Digital Orthodontics" Am. J. Orthodont. Dentofacial Orthopedics (2000) 117(2) 240-242.

Sheridan, Moving Teeth with Essix™ Appliances: Windows & Divots™, Essix™ Appliances, Fabrication, Application and rationale, raintree Essix & ARS Materials, Inc., Technical Magazine, http://www.essix.com/magazine/default.html, Aug. 1997, 7 pgs.

Shilliday, Minimizing Finishing Problems with the Mini-positioner, Am. J. Orthod. vol. 59, No. 6, Jun. 1971, pp. 596-599.

Warunek et al., Physical and Mechanical Properties of Elastomers in Orthodontic Positioners, Am. J. Orthod. Dentofac. Orthop. vol. 95, No. 5, May 1989, pp. 388-400.

Wells, Application of the Positioner Appliance in Orthodontic Treatment, Am. J. Orthodont. vol. 58, No. 4, Oct. 1970, pp. 351-366.

Yoshii, Research on an New Orthodontic Appliance: The Dynamic Positioner (D.P.)-I. The D.P. Concept and Implementation of Transparent Silicone Resin (Orthocon), Nippon Dental Review, vol. 452, Jun. 1980, pp. 61-74.

Yoshii, Research on a New Orthodontic Appliance: The Dynamic Positioner (D.P.)-II. The D.P. Manufacturing Procedure and Clinical Applications, Nippon Dental Review, vol. 454, Aug. 1980, pp. 107-130).

Yoshii, Reseach on a New Orthodontic Appliance: The Dynamic Positioner (D.P.)-III. The General Concept of the D.P. Method and its Therapeutic Effect, Part 1. Dental and Functional Reversed Occlusion Case Reports, Nippon Dental Review, vol. 457, Nov. 1980, pp. 146-164.

Yoshii, Research on a New Orthodontic Appliance: The Dynamic Positioner (D.P.)-III. The General Concept of the D.P. Method and its Therapeutic Effect, Part 2. Skeletal Reversed Occulsion Case Reports, Nippon Dental Review, vol. 458, Dec. 1980, pp. 112-129.

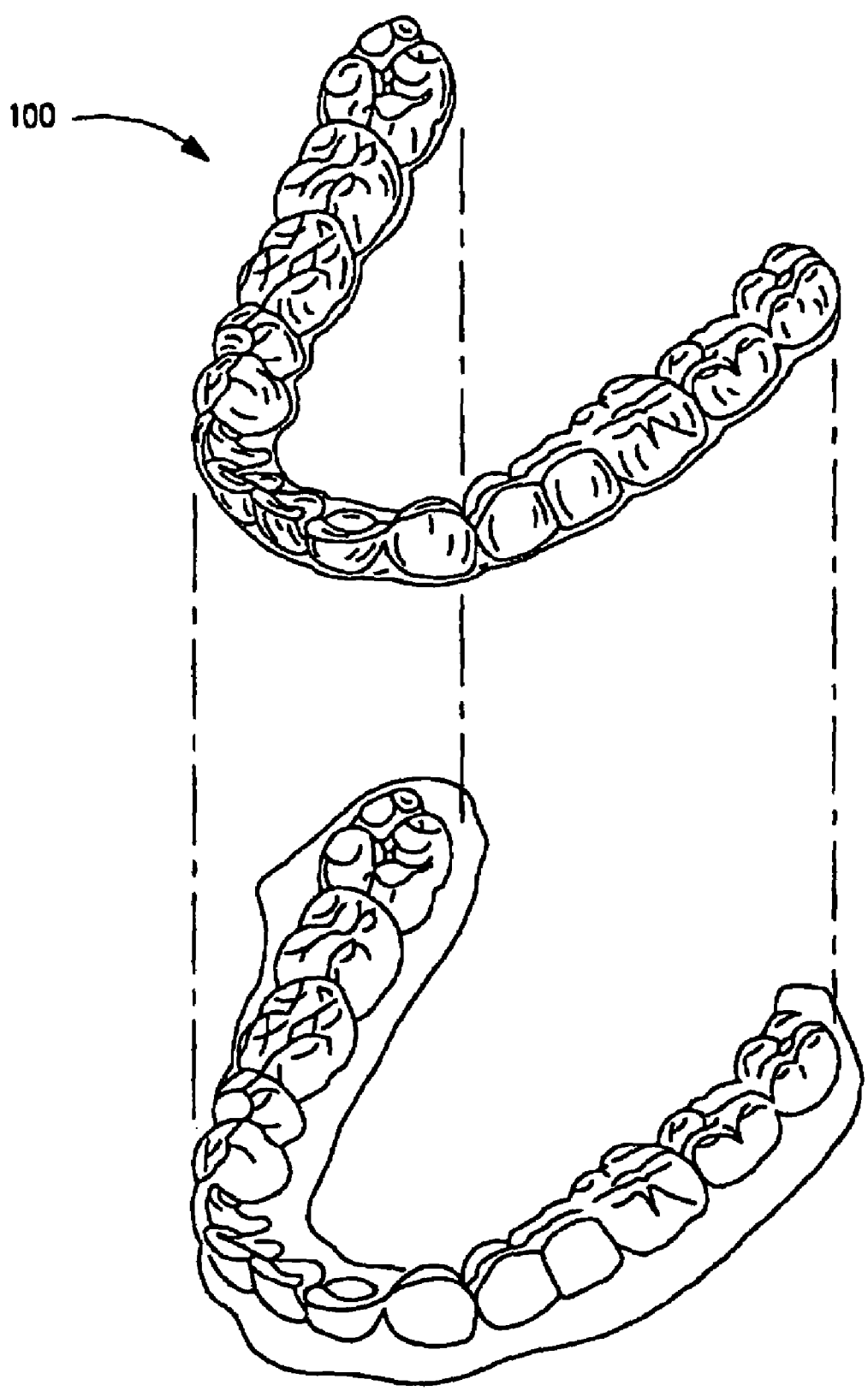
FIG. IC

COMPUTER AUTOMATED DEVELOPMENT OF AN ORTHODONTIC TREATMENT PLAN AND APPLIANCE

CROSS-REFERENCES TO RELATED APPLICATIONS

This application is a continuation of U.S. application Ser. No. 09/686,190, filed Oct. 10, 2000, (now abandoned), which was a continuation of U.S. application Ser. No. 09/169,276, filed Oct. 8, 1998, (now abandoned), which is a continuation-in-part of PCT Application No. PCT/US99/12691, filed on Jun. 19, 1998, which claimed priority from U.S. patent application Ser. No. 08/947,080, filed on Oct. 8, 1997, (now U.S. Pat. No. 5,975,893), which claims priority from U.S. Provisional Application No. 60/050,342, filed on Jun. 20, 1997, the full disclosures of which are incorporated in this application by reference.

This application is related to U.S. patent application Ser. No. 09/169,036, filed Oct. 8, 1998 (now U.S. Pat. No. 6,450,807) and U.S. patent application Ser. No. 09/169,034, filed Oct. 8, 1998, (now U.S. Pat. No. 6,471,511), both filed on Oct. 8, 1998, the full disclosures of which are incorporated herein by reference.

BACKGROUND OF THE INVENTION

1. Field of the Invention

The invention relates generally to the field of orthodontics and, more particularly, to computer automated development of an orthodontic treatment plan and appliance.

Repositioning teeth for aesthetic or other reasons is accomplished conventionally by wearing what are commonly referred to as "braces." Braces comprise a variety of appliances such as brackets, archwires, ligatures, and O-rings. Attaching the appliances to a patient's teeth is a tedious and time consuming enterprise requiring many meetings with the treating orthodontist. Consequently, conventional orthodontic treatment limits an orthodontist's patient capacity and makes orthodontic treatment quite expensive.

Before fastening braces to a patient's teeth, at least one appointment is typically possibly at a later meeting, an alginate mold of the patient's teeth is typically made. This mold provides a model of the patient's teeth that the orthodontist uses in conjunction with the X-rays and photographs to formulate a treatment strategy. The orthodontist then typically schedules one or more appointments during which braces will be attached to the patient's teeth.

At the meeting during which braces are first attached, the teeth surfaces are initially treated with a weak acid. The acid optimizes the adhesion properties of the teeth surfaces for brackets and bands that are to be bonded to them. The brackets and bands serve as anchors for other appliances to be added later. After the acid step, the brackets and bands are cemented to the patient's teeth using a suitable bonding material. No force-inducing appliances are added until the cement is set. For this reason, it is common for the orthodontist to schedule a later appointment to ensure that the brackets and bands are well bonded to the teeth.

The primary force-inducing appliance in a conventional set of braces is the archwire. The archwire is resilient and is attached to the brackets by way of slots in the brackets. The archwire links the brackets together and exerts forces on them to move the teeth over time. Twisted wires or elastomeric O-rings are commonly used to reinforce attachment of the archwire to the brackets. Attachment of the archwire to the brackets is known in the art of orthodontia as "ligation" and wires used in this procedure are called "ligatures." The elastomeric O-rings are called "plastics."

After the archwire is in place, periodic meetings with the orthodontist are required, during which the patient's braces will be adjusted by installing a different archwire having different force-inducing properties or by replacing or tightening existing ligatures. Typically, these meetings are scheduled every three to six weeks.

As the above illustrates, the use of conventional braes is a tedious and time consuming process and requires many visits to the orthodontist's office. Moreover, from the patient's perspective, the use of braces is unsightly, uncomfortable, presents a risk of infection, and makes brushing, flossing, and other dental hygiene procedures difficult.

For these reasons, it would be desirable to provide alternative methods and systems for repositioning teeth. Such methods and systems should be economical, and in particular should reduce the amount of time required by the orthodontist in planning and overseeing each individual patient. The methods and systems should also be more acceptable to the patient, in particular being less visible, less uncomfortable, less prone to infection, and more compatible with daily dental hygiene. At least some of these objectives will be met by the methods and systems of the present invention described hereinafter.

2. Description of the Background Art

Tooth positioners for finishing orthodontic treatment are described by Kesling in the *Am. J. Orthod. Oral. Surg.* 31:297–304 (1945) and 32:285–293 (1946). The use of silicone positioners for the comprehensive orthodontic realignment of a patient's teeth is described in Warunek et al. (1989) *J. Clin. Orthod.* 23:694–700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

Other publications describing the fabrication and use of dental positioners include Kleemann and Janssen (1996) *J. Clin. Orthodon.*, 30:673–680; Cureton (1996) *J. Clin. Orthodon.*, 30:390–395; Chiappone (1980) *J. Clin. Orthodon.*, 14:121–133; Shilliday (1971) *Am. J. Orthodontics*, 59:596–599; Wells (1970) *Am. J. Orthodontics*, 58:351–366; and Cottingham (1969) *Am. J. Orthodontics*, 55:23–31.

Kuroda et al. (1996) *Am. J. Orthodontics*, 110:365–369 describes a method for laser scanning a plaster dental cast to produce a digital image of the cast. See also U.S. Pat. No. 5,605,459.

U.S. Pat. Nos. 5.533.895; 5.474.448; 5.45-1,717: 5.447.432; 5.431.562: 5.395,238; 5,368,478: and 5,139,419. assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5.587,912. Computerized digital imaging of the jaw is described in U.S. Pat. Nos. 5,342,202 and 5,340,309. Other patents of interest include U.S. Pat. Nos. 5,549,476; 5,382,164; 5,273,429;

4,936,862; 3,860,803; 3,660,900; 5,645,421; 5,055,039; 4,798,534; 4,856,991; 5,035,613; 5,059,118; 5,186,623; and 4,755,139.

BRIEF SUMMARY OF THE INVENTION

In one aspect, the invention relates to the computer-automated creation of a plan for repositioning an orthodontic patient's teeth. A computer receives an initial digital data set representing the patient's teeth at their initial positions and a final digital data set representing the teeth at their final positions. The computer uses the data sets to generate treatment paths along which the teeth will move from the initial positions to the final positions.

In some implementations, the initial digital data set includes data obtained by scanning a physical model of the patient's teeth, such as by scanning a positive impression or a negative impression of the patient's teeth with a laser scanner or a destructive scanner. The positive and negative impression may be scanned while interlocked with each other to provide more accurate data. The initial digital data set also may include volume image data of the patient's teeth, which the computer can convert into a 3D geometric model of the tooth surfaces, for example using a conventional marching cubes technique. The computer also can be used to segment the initial digital data set automatically into individual tooth models, such as by performing a feature detection or matching operation on the image data. In some embodiments, the individual tooth models include data representing hidden tooth surfaces, such as roots imaged through x-ray, CT scan, or MRI techniques. Tooth roots and hidden surfaces also can be extrapolated from the visible surfaces of the patient's teeth.

In other embodiments, the computer applies a set of rules to detect collisions that will occur as the patient's teeth move along the treatment paths. One technique for collision detection is the creation of a collision buffer between two teeth at a given step along the treatment path. The computer also can be used to detect improper bite occlusions that will occur as the patient's teeth move along the treatment paths. Other embodiments allow the computer to render a three-dimensional (3D) graphical representation of the teeth at any selected treatment step. The computer also can be used to animate the graphical representation of the teeth to provide a visual display of the movement of the teeth along the treatment paths.

A VCR metaphor in the graphical user interface allows the user to control the animation. Level of detail compression can be used to improve the speed at with the 3D image of the teeth is rendered. Moreover, some embodiments allow the user to modify the underlying digital data set by repositioning a tooth in the 3D graphical representation.

In another aspect, the invention involves generating three-dimensional models of individual teeth from an initial data set that contains a 3D representation of a group of teeth. A computer performs this task by identifying points in the initial data set corresponding to each individual tooth and then segmenting the initial data set into multiple data sets, each containing the points identified for one of the teeth. In some embodiments, the computer stores each data set as a 3D geometric model representing the visible surfaces of the corresponding tooth. The computer can be used to modify each 3D model to include hidden surfaces of the corresponding tooth. In other embodiments, the initial data set contains digital volume image data, and the computer converts the volume image data into a 3D geometric model by detecting volume elements in the image data between which a sharp transition in digital image value occurs.

In another aspect, the invention relates to determining whether a patient's teeth can be moved from a first set of positions to a second set of positions. A computer performs this task by receiving a digital data set representing the teeth at the second set of positions and determining whether any of the teeth will collide while moving to the second set of positions. In some embodiments, the computer calculates distances between two of the teeth (a first tooth and a second tooth) by establishing a neutral projection plane between the first tooth and the second tooth, establishing a z-axis that is normal to the plane and that has a positive direction and a negative direction from each of a set of base points on the projection plane, computing a pair of signed distances comprising a first signed distance to the first tooth and a second signed distance to the second tooth, the signed distances being measured on a line passing through the base points and parallel to the z-axis, and determining that a collision will occur if any of the pair of signed distances indicates a collision.

In another aspect, the invention relates to determining final positions for an orthodontic patient's teeth. A computer receives a digital data set representing the teeth at recommended final positions, renders a three-dimensional (3D) graphical representation of the teeth at the recommended final positions, receives an instruction to reposition one of the teeth in response to a user's manipulation of the tooth in the graphical representation, and, in response to the instruction, modifies the digital data set to represent the teeth at the user-selected final positions.

In another aspect, the invention relates to analyzing a recommended treatment plan for an orthodontic patient's teeth. A computer receives a digital data set representing the patient's upper teeth after treatment, receives a digital data set representing the patient's lower teeth after treatment, orients the data in the data sets to simulate the patient's bite occlusion, manipulates the data sets in a manner that simulates motion of human jaws, and detects collisions between the patient's upper teeth and lower teeth during the simulation of motion. The simulation of motion can be based on observed motion of typical human jaws or the patient's jaws.

BRIEF DESCRIPTION OF THE DRAWINGS

FIG. 1C illustrates the jaw of FIG. 1A together with an incremental position adjustment appliance.

DETAILED DESCRIPTION OF THE INVENTION

Systems and methods are provided for moving teeth incrementally using a plurality of discrete appliances, where each appliance successively moves one or more of the patient's teeth by relatively small amounts. The tooth movements will be those normally associated with orthodontic treatment, including translation in all three orthogonal directions relative to a vertical centerline, rotation of the tooth centerline in the two orthodontic directions ("root angulation" and "torque"), as well as rotation about the centerline.

Figure 1A:
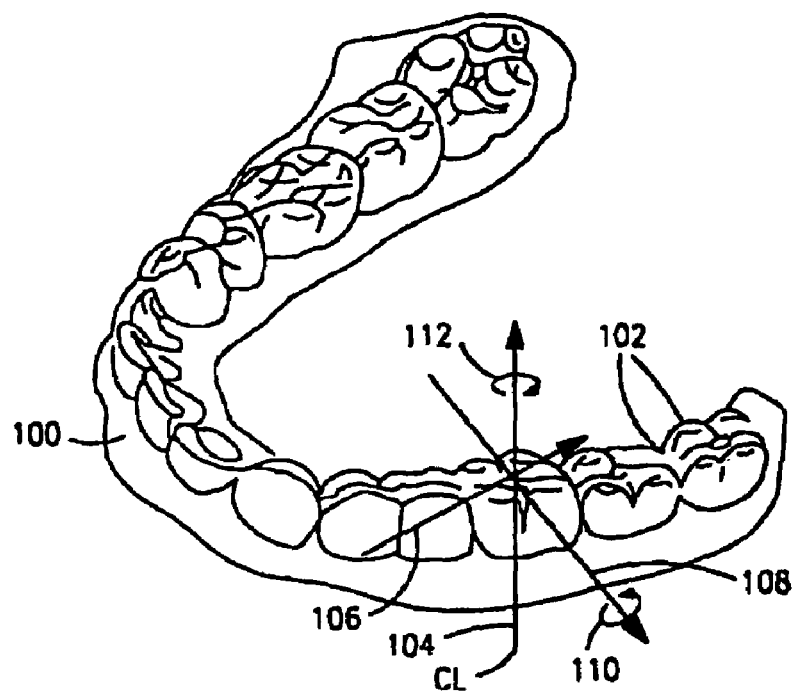
FIG. 1A illustrates a patient's jaw and provides a general indication of how teeth may be moved.

Referring now to FIG. 1A, a representative jaw 100 includes sixteen teeth, at least some of which are to be moved from an initial tooth arrangement to a final tooth arrangement. To understand how the teeth may be moved, an arbitrary centerline (CL) is drawn through one of the teeth 102. With reference to this centerline (CL), the teeth may be moved in the orthogonal directions represented by axes 104, 106, and 108 (where 104 is the centerline). The centerline may be rotated about the axis 108 (root angulation) and 104 (torque) as indicated by arrows 110 and 112, respectively. Additionally, the tooth may be rotated about the centerline, as represented by arrow 114. Thus, all possible free-form motions of the tooth can be performed.

Figure 1B:
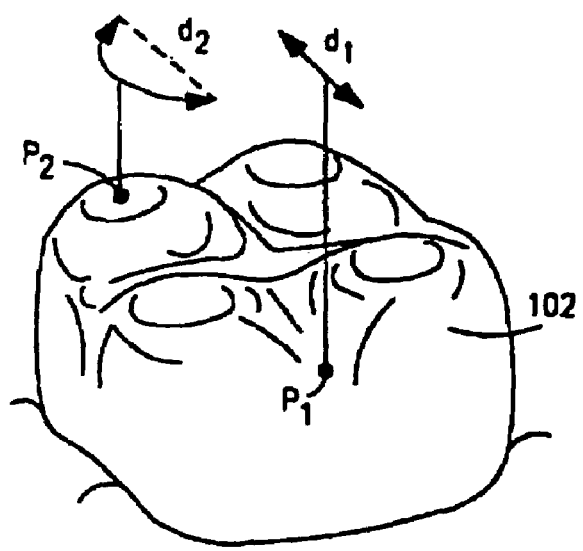
FIG. 1B illustrates a single tooth from FIG. 1A and defines how tooth movement distances are determined.

Referring now to FIG. 1B, the magnitude of any tooth movement is defined in terms of the maximum linear translation of any point P on a tooth 102. Each point $P_i$ will undergo a cumulative translation as that tooth is moved in any of the orthogonal or rotational directions defined in FIG. A. That is, while the point will usually follow a non-linear path, there will be a linear distance between any point in the tooth when determined at any two times during the treatment. Thus, an arbitrary point $P_1$ may in fact undergo a true side-to-side translation as indicated by arrow $d_1$, while a second arbitrary point P2 may travel along an arcuate path, resulting in a final translation d–). In many situations, the maximum permissible movement of a point $P_i$ in any particular tooth is defined as the maximum linear translation of that point $P_i$ on the tooth which undergoes the maximum movement for that tooth in any treatment step.

One tool for a incrementally repositioning the teeth in a patient's jaw is a set of one or more adjustment appliances. Suitable appliances include any of the known positioners, retainers, or other removable appliances which are used for finishing and maintaining teeth positions in connection with conventional orthodontic treatment. As described below, a plurality of such appliances can be worn by a patient successively to achieve gradual tooth repositioning. A particularly advantageous appliance is the appliance 100, shown in FIG. 1C, which typically comprises a polymeric shell having a cavity shaped to receive and resiliently reposition teeth from one tooth arrangement to another tooth arrangement. The polymeric shell typically fits over all teeth present in the upper or lower jaw. Often, only some of the teeth will be repositioned while others will provide a base or anchor region for holding the repositioning appliance in place as it applies the resilient repositioning force against the tooth or teeth to be repositioned. In complex cases, however, many or most of the teeth will be repositioned at some point during the treatment. In such cases, the teeth which are moved can also serve as a base or anchor region for holding the repositioning appliance. The gums and the palette also serve as an anchor region in some cases, thus allowing all or nearly all of the teeth to be repositioned simultaneously.

The polymeric appliance 100 of FIG. 1C is preferably formed from a thin sheet of a suitable elastomeric polymeric, such as Tru-Tain 0.03 in. thermal forming dental material, marketed by Tru-Tain Plastics, Rochester, Minn. 55902. In many cases, no wires or other means are provided for holding the appliance in place over the teeth. In some cases, however, it is necessary to provide individual attachments on the teeth with corresponding receptacles or apertures in the appliance 100 so that the appliance can apply forces that would not be possible or would be difficult to apply in the absence of such attachments.

Building a Digital Model of the Patient's Teeth
Gathering Data About the Teeth

Figure 2:
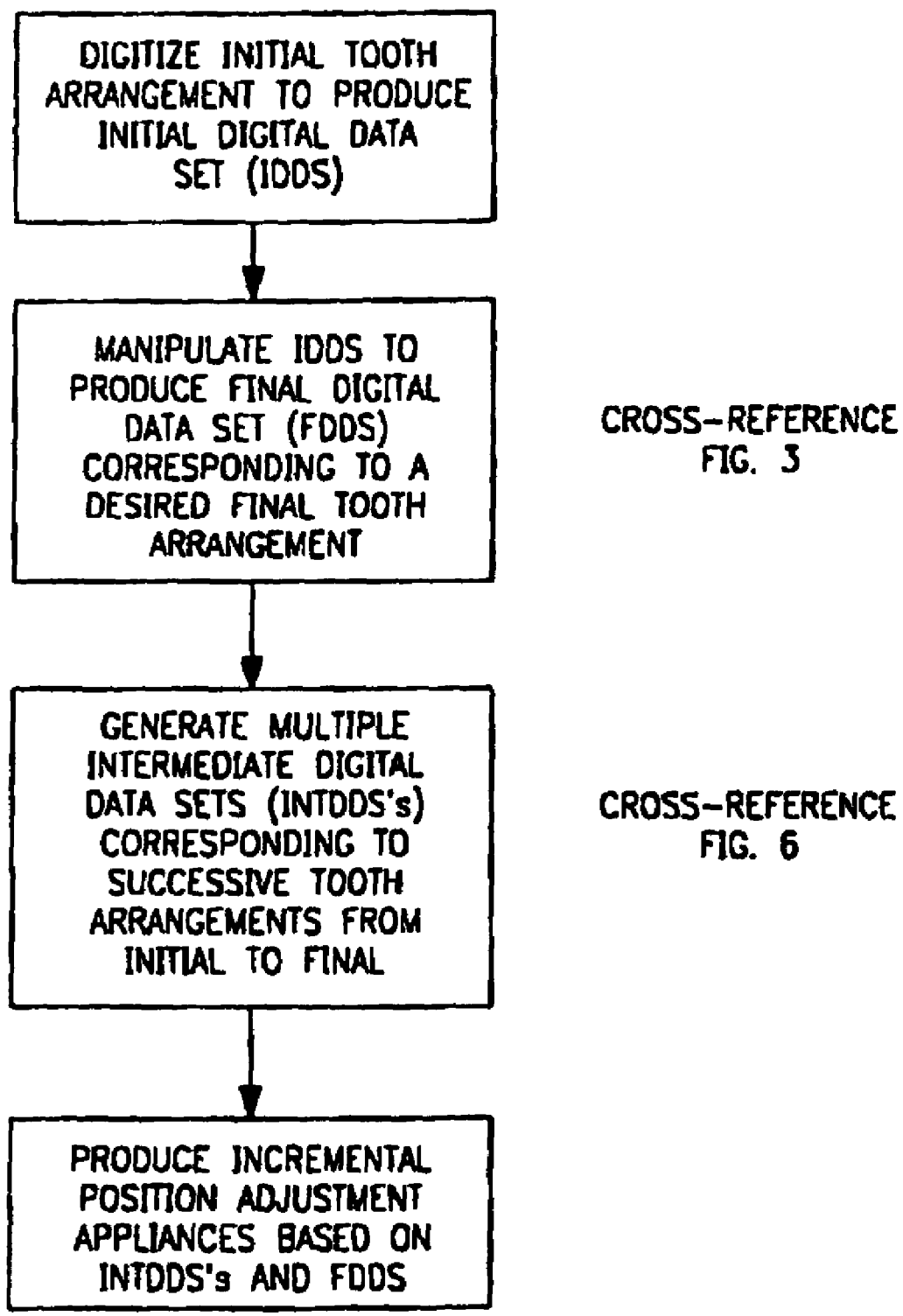
FIG. 2 is a block diagram illustrating steps for producing a system of incremental position adjustment appliances.

Referring now to FIG. 2, a method for producing the incremental position adjustment appliances for subsequent use by a patient to reposition the patient's teeth will be described. As a first step, a digital data set representing an initial tooth arrangement is obtained, referred to hereinafter as the initial digital data set, or IDDS. The IDDS may be obtained in a variety of ways. For example, the patient's teeth may be scanned or imaged using well known technology, such as X-rays, three-dimensional X-rays, computer-aided tomographic images or data sets, and magnetic resonance images. Methods for digitizing such conventional images to produce useful data sets are well known and described in the patent and medical literature. Usually, however, a plaster cast of the patient's teeth is obtained by well known techniques, such as those described in Graber, Orthodontics: Principle and Practice, Second Edition, Saunders, Philadelphia, 1969, pp. 401–415.

After the tooth casting is obtained, the casting is digitally scanned by a scanner, such as a non-contact type laser or destructive scanner or a contact-type scanner, to produce the IDDS. The data set produced by the scanner may be presented in any of a variety of digital formats to ensure compatibility with the software used to manipulate images represented by the data, as described in more detail below. General techniques for producing plaster casts of teeth and generating digital models using laser scanning techniques are described, for example, in U.S. Pat. No. 5,605,459, the full disclosure of which is incorporated in this application by reference.

Suitable scanners include a variety of range acquisition systems, generally categorized by whether the acquisition process requires contact with the three dimensional object being scanned. Some contact-type scanners use probes having multiple degrees of translational and/or rotational freedom. A computer-readable (i.e., digital) representation of the sample object is generated by recording the physical displacement of the probe as it is drawn across the sample surface.

Conventional non-contact-type scanners include reflective-type and transmissive-type systems. A wide variety of reflective systems are in use today, some of which utilize non-optical incident energy sources such as microwave radar or sonar. Others utilize optical energy. Non-contact-type systems that use reflected optical energy usually include special instrumentation that carry out certain measuring techniques (e.g., imaging radar, triangulation and interferometry).

One type of non-contact scanner is an optical. reflective scanner, such as a laser scanner. ion-contact scanners such as this are inherently nondestructive (i.e., do not damage the sample object), generally are characterized by a relatively high capture resolution, and are capable of scanning a sample in a relatively short period of time. One such scanner is the Cyberware, Model 15 scanner manufactured by Cyberware, Inc., Monterey, Calif.

Both non-contact-type and contact-type scanners also can include color cameras which, when synchronized with the scanning capabilities, provide means for capturing, in digital format, color representations of the sample objects. The importance of this ability to capture not just the shape of the sample object but also its color is discussed below.

Other scanners, such as the CSS-1000 model destructive scanner produced by Capture Geometry Inside (CGI), Minneapolis, Minn., can provide more detailed and precise information about a patient's teeth than a typical range acquisition scanner can provide. In particular, a destructive scanner can image areas that are hidden or shielded from a range acquisition scanner and therefore may not be subject to adequate imaging. The CSS-1000 scanner gathers image data for an object by repeatedly milling thin slices from the object and optically scanning the sequence of milled surfaces to create a sequence of 2D image slices, so none of the object's surfaces are hidden from the scanner. Image processing software combines the data from individual slices to form a data set representing the object, which later is converted into a digital representation of the surfaces of the object, as described below.

The destructive scanner may be used in conjunction with a laser scanner to create a digital model of a patient's teeth. For example, a laser scanner may be used first to build a low resolution image of a patient's upper and lower arches coupled with the patient's wax bite, as described below. The destructive scanner then may be used to form high-resolution images of the individual arches. The data obtained by the laser scanner indicates the relation between the patient's upper and lower teeth which later can be used to relate to each other the images generated by the destructive scanner and the digital models derived from them.

The destructive scanner can be used to form the initial digital data set (IDDS) of the patient's teeth by milling and scanning a physical model, such as a plaster casting, of the teeth. To ensure a consistent orientation of the casting throughout the destructive scanning process, a scanning system operator pots the casting in potting material, such as Encase-It epoxy from CGI. and cures the material in a pressure vacuum (PV) chamber to form a mold. Placing the potting material into the PV chamber ensures that the material sets relatively quickly with virtually no trapped air bubbles. The color of the potting material is selected to contrast sharply with the color of the casting material to ensure the clarity of the scanned image. The operator, then mounts the mold to a mounting plate and places the molding plate in the destructive scanning system.

A slicing mechanism ("cutter") in the destructive scanning system mills a thin slice (typically between 0.001" and 0.006" thick) from the mold, and a positioning arm places the milled surface near an optical scanner. The optical scanner, which may be an off-the-shelf device such as a flatbed scanner or a digital camera, scans the surface to create a 2D image data set representing the surface. The positioning arm then repositions the mold below the cutter, which again mills a thin slice from mold. The resulting output of the destructive scanning system is a 3D image data set, which later is converted into a digital model of surfaces, as described in detail below. A destructive scanning system and the corresponding destructive scanning and data processing are described in U.S. Pat. No. 5,621,648.

Figure 12:
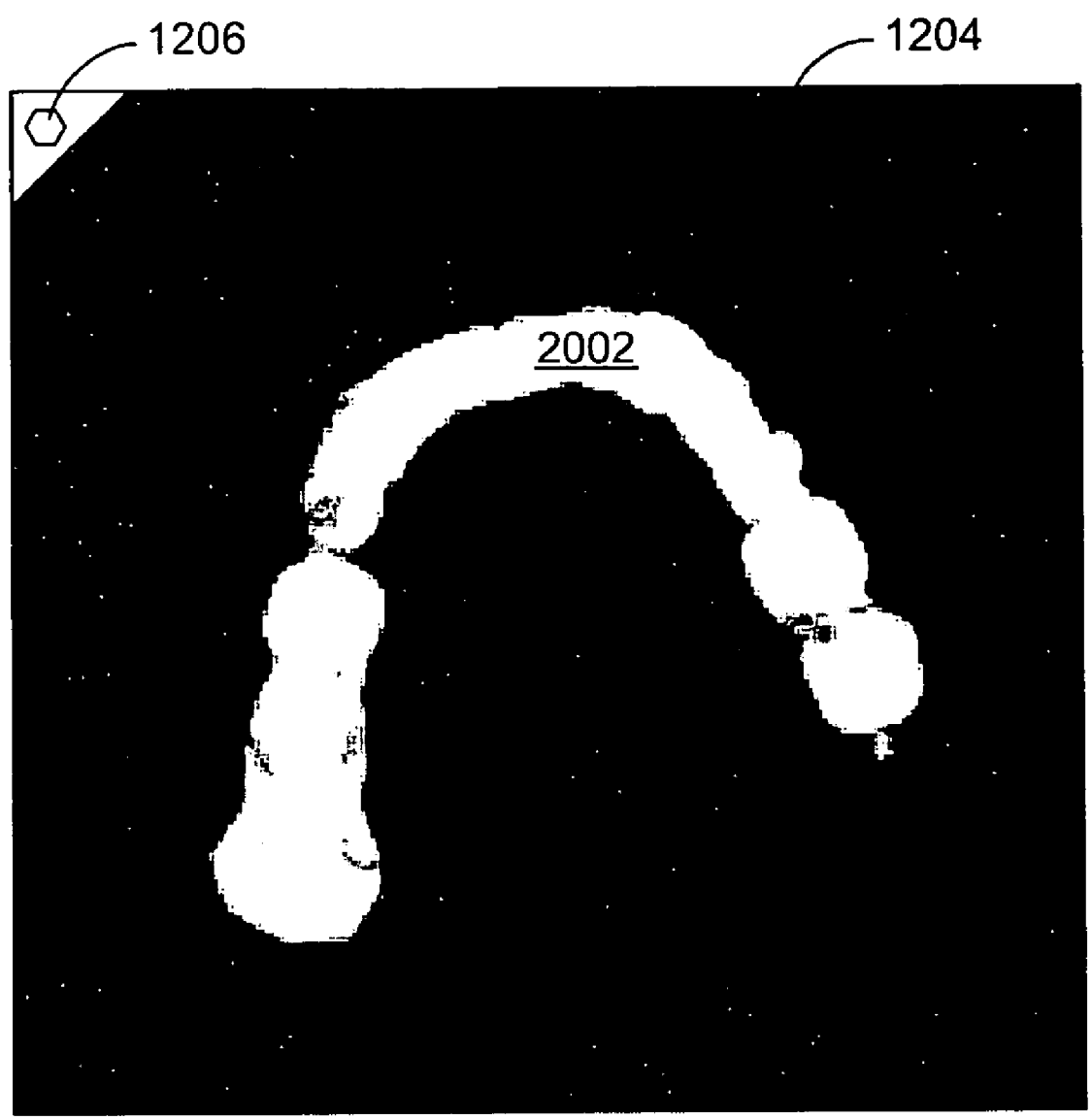
FIG. 12 is cross-sectional image of a plaster tooth casting in an epoxy mold.

FIG. 12 shows a scanned image 1200 of an exposed surface of a plaster tooth casting 1202 embedded in an epoxy mold 1204. The black color of the epoxy mold 1204 provides sharp contrast with the white color of the plaster casting 1202. An orientation guide 1206 appears in a corner of each image slice to ensure proper alignment of the image data after the destructive scan. The orientation guide 1206 can include a rigid structure, such as a piece of PVC tubing, embedded in the mold 1204.

A patient's wax bite can be used to acquire the relative positions of the upper and lower teeth in centric occlusion. For a laser scan, this can be accomplished by first placing the lower cast in front of the scanner, with the teeth facing upwards, then placing the wax bite on top of the lower cast. and finally placing the upper cast on top of the lower cast. with the teeth facing downwards. resting on the wax bite. A cylindrical scan is then acquired for the lower and upper casts in their relative positions. The scanned data provides a digital model of medium resolution representing an object which is the combination of the patient's arches positioned in the same relative configuration as in the mouth.

The digital model acts as a template guiding the placement of the two individual digital models (one per arch). More precisely, using software, for example the CyberWare alignment software, each digital arch is in turn aligned to the pair scan. The individual models are then positioned relative to each other corresponding to the arches in the patient's mouth.

The waxbite can also be scanned separately to provide a second set of data about the teeth in the upper and lower arches. In particular, the plaster cast provides a "positive" image of the patient's teeth, from which one set of data is derived, and the waxbite provides a "negative" image of the teeth, from which a second, redundant set of data is derived. The two sets of data can then be matched to form a single data set describing the patient's teeth with increased accuracy and precision. The impression from which the plaster cast was made also can be used instead of or in addition to the waxbite.

Figure 13:
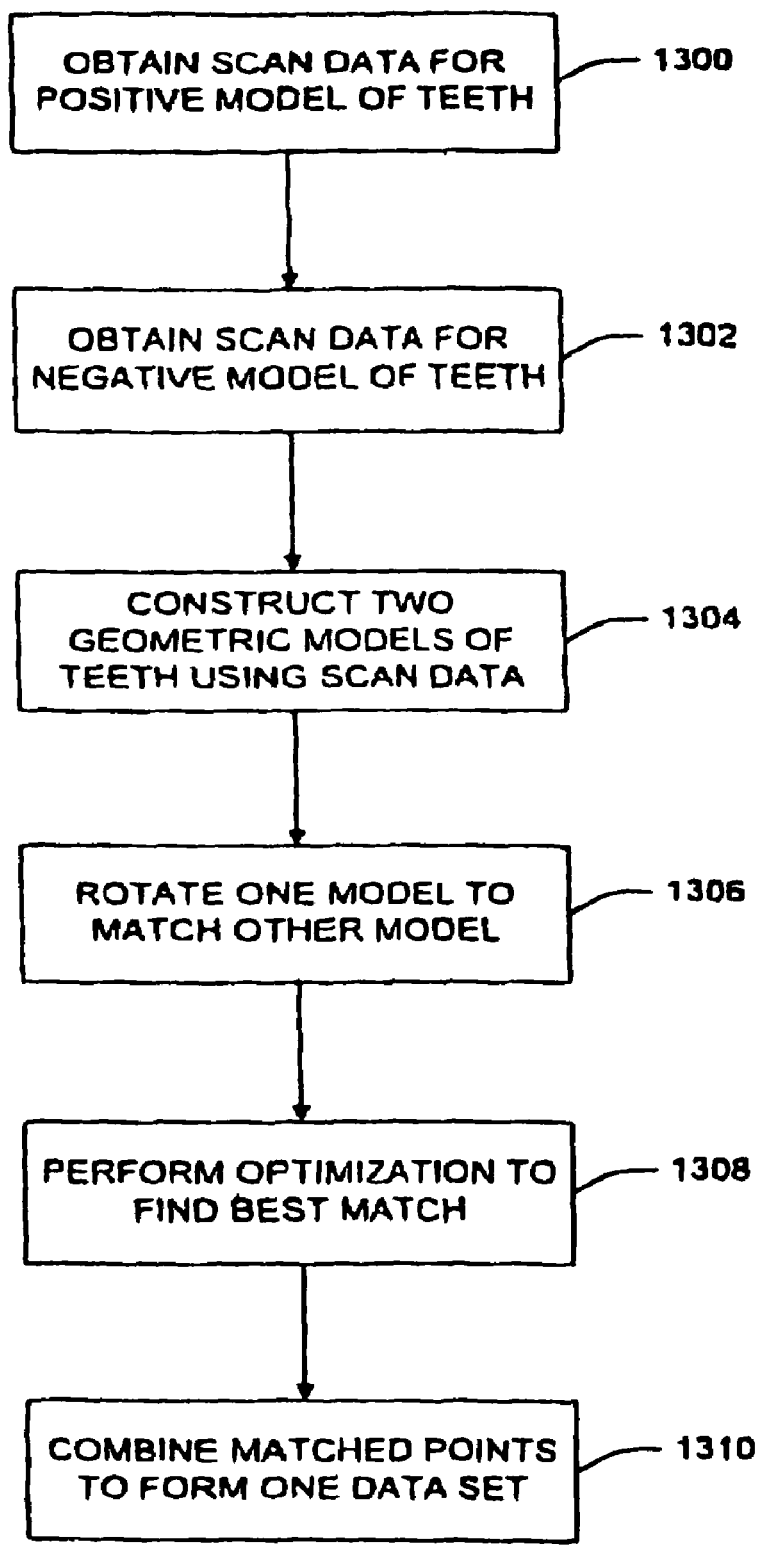
FIG. 13 is a flow chart of a process for forming one 3D image data set of teeth from two sets of image data.

FIG. 13 is a flow chart of a process for deriving a single set of data from a positive data set and a negative data set. First, scan data representing positive and negative physical tooth models is obtained (steps 1300, 1302). If the scan data was acquired through a destructive scanning process, two digital 3D geometric models are constructed from the data, as described below (step 1304). Scan data acquired from an optical or range acquisition scanner system typically suffices as a geometric model. One of the geometric models is positioned to match roughly with the other model in the digital model space (step 1306), and an optimization process is performed to determine the best match between the models (step 1308). The optimization process attempts to match one point in each model to one point in the other model. Each pair of matched points then is combined into a single point to form a single set of data (step 1310). The combining of matched points can be carried out in a variety of ways, for example, by averaging the coordinates of the points in each pair.

While a laser scanning system typically must perform three scans to image a patient's full set of teeth adequately (one high resolution scan for each of the upper and lower casts and a medium resolution waxbite scan), the destructive scanning system described above can image a patient's full set of teeth adequately with only a single waxbite scar. Scanning both casts with the wax bite in place ensures that all important surfaces of the upper and lower teeth are captured during a destructive scan. Scanning both casts in this manner also provides a high resolution image data set that preserves the relation between the patient's upper and lower teeth. Like the potting material described above, the wax bite should have a color that contrasts sharply with the color of the casting material to ensure the clarity of the scanned image. The wax bite may be the same color as the potting material if no contrast is desired between the waxbite and the potting material. Alternatively, the color of the wax bite may contrast sharply with the tooth casts and the potting material if an image of the wax bite is needed.

In addition to the 3D image data gathered by laser scanning or destructive scanning the exposed surfaces of the teeth, a user may wish to gather data about hidden features, such as the roots of the patient's teeth and the patient's jaw bones. This information is used to build a more complete model of the patient's dentition and to show with more accuracy and precision how the teeth will respond to treatment. For example, information about the roots allows modeling of all tooth surfaces, instead of just the crowns, which in turn allows simulation of the relationships between the crowns and the roots as they move during treatment. Information about the patient's jaws and gums also enables a more accurate model of tooth movement during treatment. For example, an x-ray of the patient's jaw bones can assist in identifying ankylose teeth, and an MRI can provide information about the density of the patient's gum tissue. Moreover, information about the relationship between the patient's teeth and other cranial features allows accurate alignment of the teeth with respect to the rest of the head at each of the treatment steps. Data about these hidden features may be gathered from many sources, including 2D and 3D x-ray systems, CT scanners, and magnetic resonance imaging (MRI) systems. Using this data to introduce visually hidden features to the tooth model is described in more detail below.

Developing an orthodontic treatment plan for a patient involves manipulating the IDDS at a computer or workstation having a suitable graphical user interface (GUI) and software appropriate for viewing and modifying the images. Specific aspects of the software will be described in detail hereinafter. However, dental appliances having incrementally differing geometries can be produced by non-computer-aided techniques. For example, plaster casts obtained as described above may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare sets of multiple appliances. generally as described below. using pressure and vacuum molding techniques.

Creating a 3D Surface Model of the Teeth

Many types of scan data, such as that acquired by an optical scanning system, provide a 3D geometric model (e.g., a triangular surface mesh) of the teeth when acquired. Other scanning techniques, such as the destructive scanning technique described above, provide data in the form of volume elements ("voxels") that can be converted into a digital geometric model of the tooth surfaces.

Figure 14:
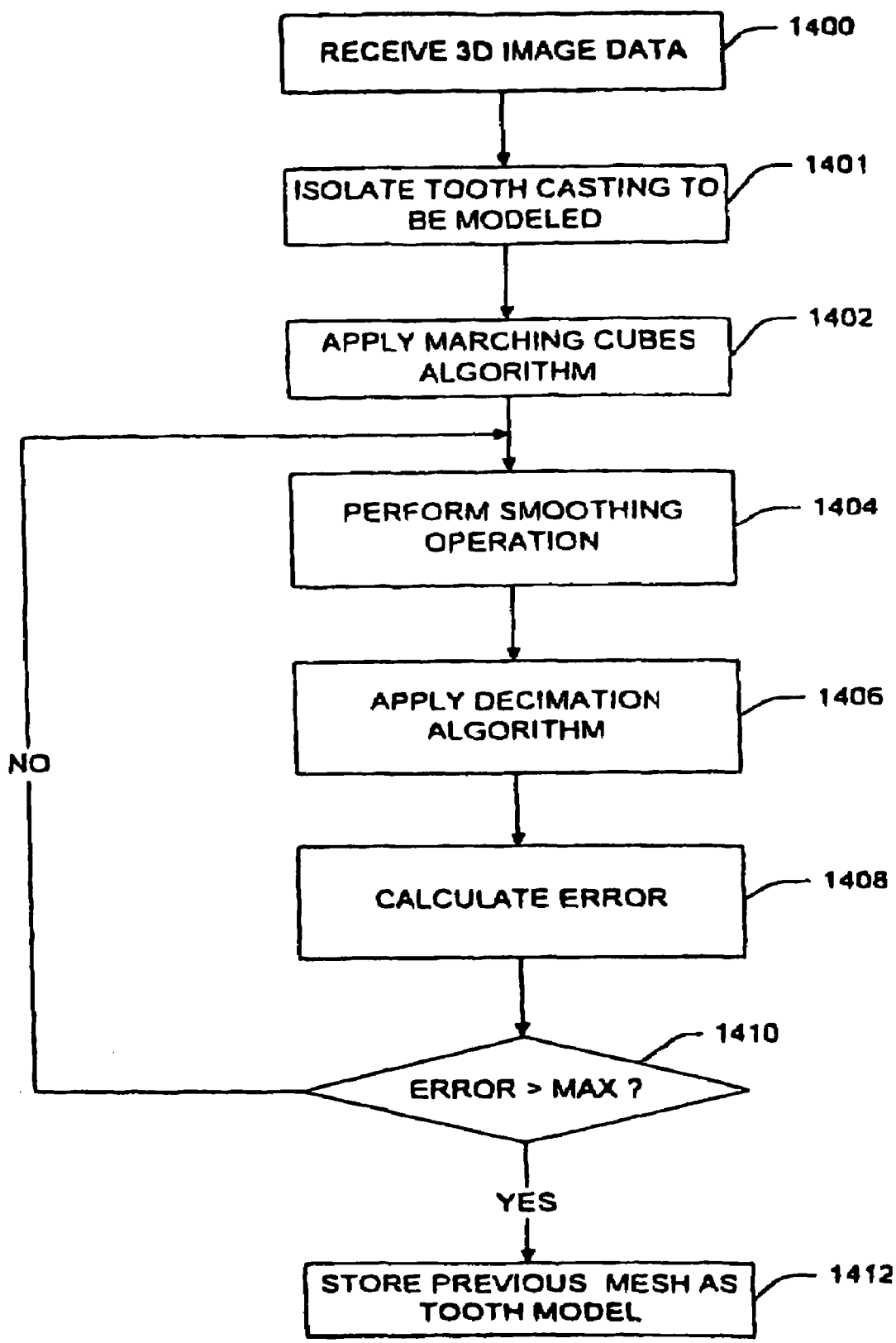
FIG. 14 is a flow chart of a process for forming a 3D surface mesh from 3D image data.

FIG. 14 is a flowchart of a process for forming a surface mesh from voxel image data. This approach involves receiving the image data from the destructive scanner (step 1400), processing the data to isolate the object to be modeled (step 1401), and applying a conventional "marching cubes" technique to create a surface mesh of the object (step 1402).

Each set of image data can include images of multiple tooth casts or of a tooth cast and extraneous, "noisy" objects, such as air bubbles in the potting material. The system identifies each object in the image by assigning each voxel a single-bit binary value (e.g., "0" for black and "1" for white) based on the voxel's 8-bit gray scale image value, and then connecting adjacent voxels that have been assigned the same single-bit value. Each group of connected voxels represents one of the objects in the image. The system then isolates the tooth casting to be modeled by masking from the image all objects except the tooth casting of interest. The system removes noise from the masked image data by passing the data through a low-pass filter.

Once the tooth casting is isolated from the image data, the system performs a conventional marching cubes technique to locate tooth and tissue surfaces in the image data. This technique involves the identification of pairs of adjacent voxels having 8-bit image values that fall on opposite sides of a selected threshold value. Specifically, each voxel has an associated image value typically a number between 0 and 255 that represents the image color or gray scale value at that voxel. Because the tooth casting and the surrounding potting material have sharply contrasting colors (see FIG. 12), the image values at voxels forming the image of the tooth casting differ greatly from the values at voxels forming the image of the surrounding material. Therefore. the marching cube algorithm, can locate the tooth surfaces by identifying the voxels at which a sharp transition in image value occurs. The algorithm can position the surface precisely between two voxels by determining the difference between the threshold value and the image value at each voxel and then placing the surface a corresponding distance from the centerpoint of each voxel.

In some implementations, after the marching cubes algorithm is applied, the resulting mesh undergoes a smoothing operation to reduce the jaggedness on the surfaces of the tooth model caused by the marching cubes conversion (step 1404). A conventional smoothing operation can be used, such as one that moves individual triangle vertices to positions representing the averages of connected neighborhood vertices to reduce the angles between triangles in the mesh.

Another optional step is the application of a decimation operation to the smoothed mesh to eliminate data points, which improves processing speed (step 1406). Conventional decimation operations identify pairs of triangles that lie almost in the same plane and combine each identified pair into a single triangle by eliminating the common vertex. The decimation operation used here also incorporates orthodontic-specific decimation rules, which rely on an understanding of the general characteristics of the teeth and gums and of the orthodontic appliances that will be used to carry out a treatment plan. For example, aligners typically do not contact the portions of the tooth surfaces adjacent to the gums, so these tooth surfaces can be modeled less accurately than the rest of the tooth. The decimation operation incorporates this knowledge by decimating more heavily along the gum line. When an appliance such as a polymeric shell aligner will be used to treat the patient's teeth, the algorithm also decimates more heavily on the sides of the teeth, where the aligner usually is required only to push orthogonally to the surface, than it decimates on the tops of the teeth, where the aligner usually must form a solid grip.

After the smoothing and decimation operation are performed, an error value is calculated based on the differences between the resulting mesh and the original mesh or the original data (step 1408), and the error is compared to an acceptable threshold value (step 1410). The smoothing and decimation operations are applied to the mesh once again if the error does not exceed the acceptable value. The last set of mesh data that satisfies the threshold is stored as the tooth model (step 1412).

Creating 3D Models of the Individual Teeth

Once a 3D model of the tooth surfaces has been constructed, models of the patient's individual teeth can be derived. In one approach, individual teeth and other components are "cut" to permit individual repositioning or removal of teeth in or from the digital data. After the components are "freed," a prescription or other written specification provided by the treating professional is followed to reposition the teeth. Alternatively, the teeth may be repositioned based on the visual appearance or based on rules and algorithms programmed into the computer. Once an acceptable final arrangement has been created, the final tooth arrangement is incorporated into a final digital data set (FDDS).

Based on both the IDDS and the FDDS, a plurality of intermediate digital data sets (INTDDS's) are generated to correspond to successive intermediate tooth arrangements. The system of incremental position adjustment appliances can then be fabricated based on the INTDDS's, as described in more detail below. Segmentation of individual teeth from the tooth model and determining the intermediate and final positions of teeth also are described in more detail below.

Simplifying the 3D Model

Figure 3:
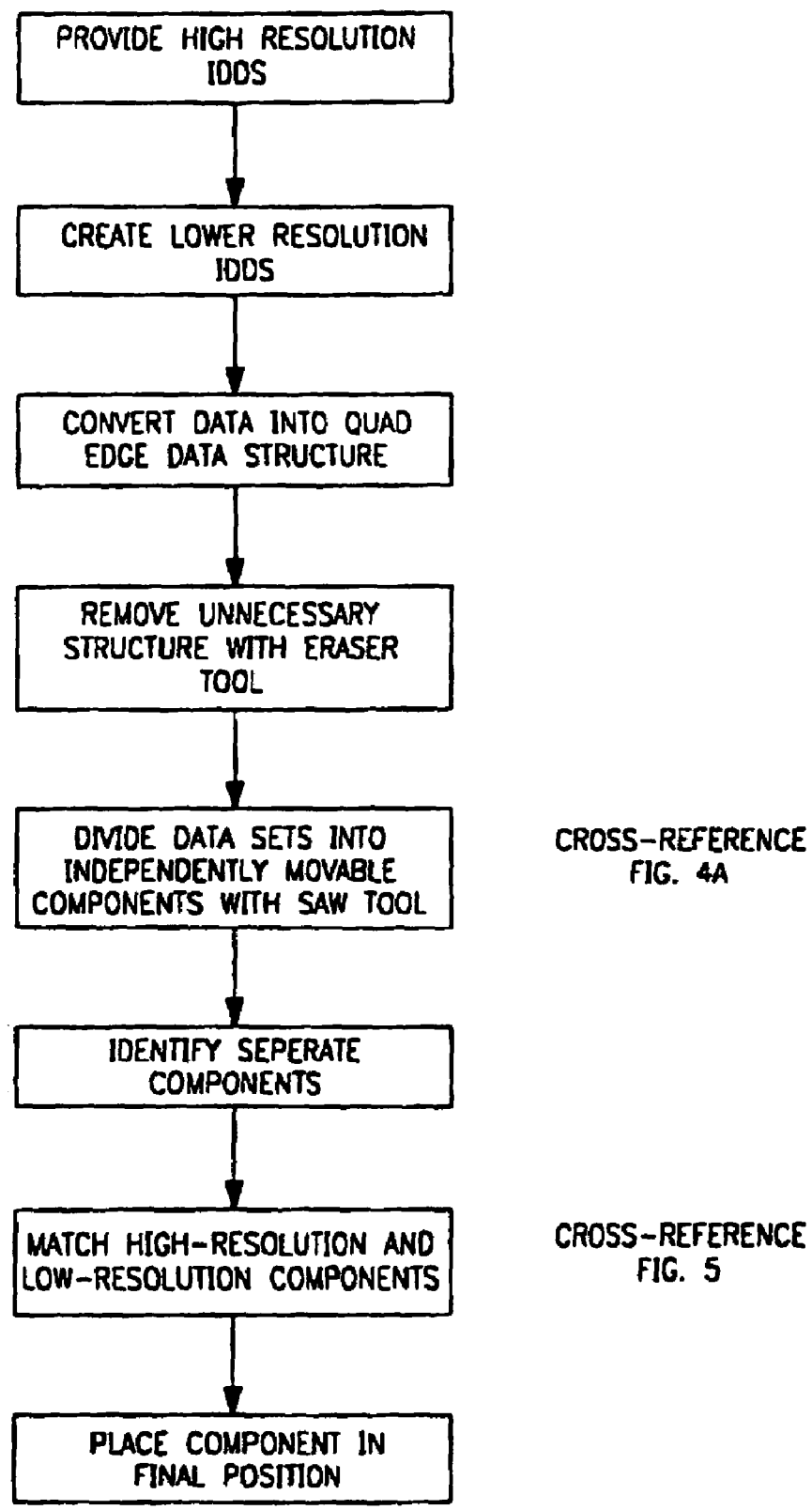
FIG. 3 is a block diagram setting forth the steps for manipulating an initial digital data set representing an initial tooth arrangement to produce a final digital data set corresponding to a desired final tooth arrangement.

FIG. 3 illustrates a representative technique for user-assisted manipulation of the IDDS to produce the FDDS on the computer. Usually, the data from the digital scanner is acquired in high resolution form. In order to reduce the computer time necessary to generate images, a parallel set of digital data representing the IDDS at a lower resolution can be created. The user can manipulate the lower resolution images while the computer updates the high resolution data set as necessary. The user can also view and manipulate the high resolution model if the extra detail provided in that model is useful. The IDDS also can be converted into a quad edge data structure if not already present in that form. A quad edge data structure is a standard topological data structure defined in *Primitives for the Manipulation of General Subdivisions and the Computation of Voronoi Diagrams*, ACM Transactions of Graphics, Vol. 4, No. 2, April 1985, pp. 74–123. Other topological data structures, such as the winged-edge data structure, could also be used.

As an initial step, while viewing the three-dimensional image of the patient's jaw, including the teeth, gingivae, and other oral tissue, the user usually deletes structure which is unnecessary for image manipulation and final production of an appliance. These unwanted sections of the model may be removed using an eraser tool to perform a solid modeling subtraction. The tool is represented by a graphic box. The volume to be erased (the dimensions, position, and orientation of the box) are set by the user employing the GUI. Typically, unwanted sections would include extraneous gum area and the base of the originally scanned cast. Another application for this tool is to stimulate the extraction of teeth and the "shaving down" of tooth surfaces. This is necessary when additional space is needed in the jaw for the final positioning of a tooth to be moved. The treating professional may choose to determine which teeth will be shaved and which teeth will be extracted. Shaving allows the patient to maintain teeth when only a small amount of space is needed. Typically, extraction and shaving are used in the treatment planning only when the actual patient teeth are to be extracted or shaved prior to initiating repositioning.

Removing unwanted or unnecessary sections of the model increases data processing speed and enhances the visual display. Unnecessary sections include those not needed for creation of the tooth repositioning appliance. The removal of these unwanted sections reduces the complexity and size of the digital data set, thus accelerating manipulations of the data set and other operations.

After the user positions and sizes the eraser tool and instructs the software to erase the unwanted section, all triangles within the box set by the user are removed and the border triangles are modified to leave a smooth, linear border. The software deletes all of the triangles within the box and clips all triangles which cross the border of the box. This requires generating new vertices on the border of the box. The holes created in the model at the faces of the box are retriangulated and closed using the newly created vertices.

In alternative embodiments. the computer automatically simplifies the digital model by performing the user-oriented functions described above. The computer applies a knowledge of orthodontic relevance to determine which portions of the digital model are unnecessary for image manipulation.

Segmenting the Teeth in the 3D Model

Human-Assisted Segmentation

The saw tool is used to define the individual teeth (or possibly groups of teeth) to be moved. The tool separates the scanned image into individual graphic components enabling the software to move the tooth or other component images independent of remaining portions of the model. In one embodiment, the saw tool defines a path for cutting the graphic image by using two cubic B-spline curves lying in space, possibly constrained to parallel planes, either open or closed. A set of lines connects the two curves and shows the user the general cutting path. The user may edit the control points on the cubic B-splines, the thickness of the saw cut, and the number of erasers used, as described below.

In an alternative embodiment, the teeth are separated by using the saw as a "coring" device, cutting the tooth from above with vertical saw cuts. The crown of the tooth, as well as the gingivae tissue immediately below the crown are separated from the rest of the geometry, and treated as an individual unit, referred to as a tooth. When this model is moved, the gingivae tissue moves relative to the crown, creating a first order approximation of the way that the gingivae will reform within a patient's mouth.

Each tooth may also be separated from the original trimmed model. Additionally, a base may be created from the original trimmed model by cutting off the crowns of the teeth. The resulting model is used as a base for moving the teeth. This facilitates the eventual manufacture of a physical mold from the geometric model, as described below.

Thickness: When a cut is used to separate a tooth, the user will usually want the cut to be as thin as possible. However, the user may want to make a thicker cut, for example, when shaving down surrounding teeth, as described above. Graphically. the cut appears as a curve bounded by the thickness of the cut on one side of the curve.

Figure 4A:
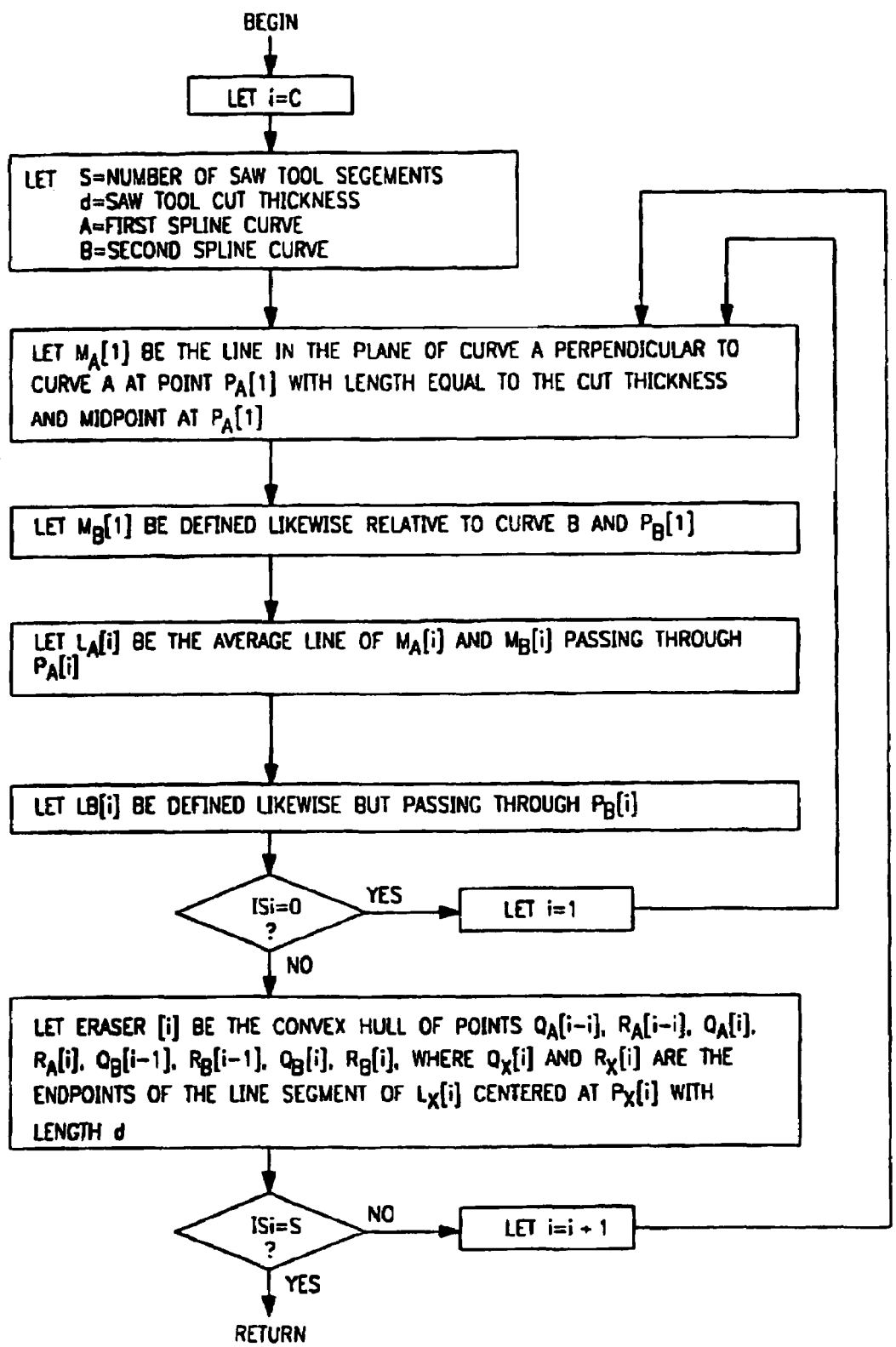
FIG. 4A is a flow chart illustrating an eraser toot for the methods herein.
Figure 4B:
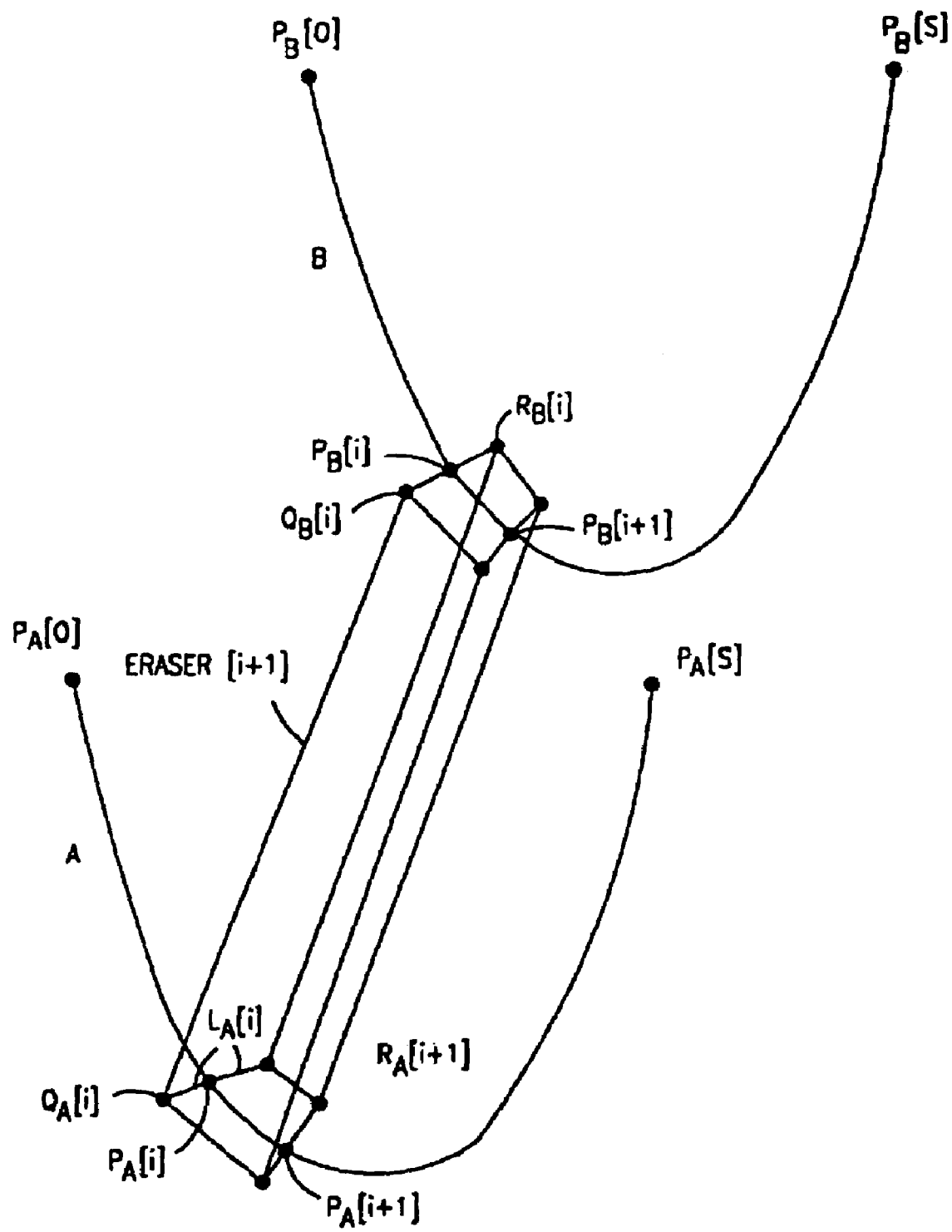
FIG. 4B illustrates the volume of space which is being erased by the program of FIG. 4A.

Number of Erasers: A cut is comprised of multiple eraser boxes arranged next to each other as a piecewise linear approximation of the Saw Tool's curve path. The user chooses the number of erasers, which determines the sophistication of the curve created: the greater the number of segments, the more accurately the cutting will follow the curve. The number of erasers is shown Graphically by the number of parallel lines connecting the two cubic B-spline curves. Once a saw cut has been completely specified the user applies the cut to the model. The cut is performed as a sequence of erasings, as shown in FIG. 4A. FIG. 4B shows a single erasing iteration of the cut as described in the algorithm for a open ended B-spline curve. For a vertical cut, the curves are closed, with $P_A[O]$ and $P_A[S]$ being the same point and $P_B[O]$ and $P_B[S]$ being the same point.

In one embodiment, the software may automatically partition the saw tool into a set of erasers based upon a smoothness measure input by the user. The saw is adaptively subdivided until an error metric measures the deviation from the ideal representation to the approximate representation to be less than a threshold specified by the smoothness setting. One error metric compares the linear length of the subdivided curve to the arclength of the ideal spline curve. When the difference is greater than a threshold computed from the smoothness setting, a subdivision point is added along the spline curve.

A preview feature may also be provided in the software. The preview feature visually displays a saw cut as the two surfaces that represent opposed sides of the cut. This allows the user to consider the final cut before applying it to the model data set.

After the user has completed all desired cutting operations with the saw tool, multiple graphic solids exist. However, at this point, the software has not determined which triangles of the quad edge data structure belong to which components. The software chooses a random starting point in the data structure and traverses the data structure using adjacency information to find all of the triangles that are attached to each other, identifying an individual component. This process is repeated starting with the triangle whose component is not yet determined. Once the entire data structure is traversed, all components have been identified.

Figure 5:
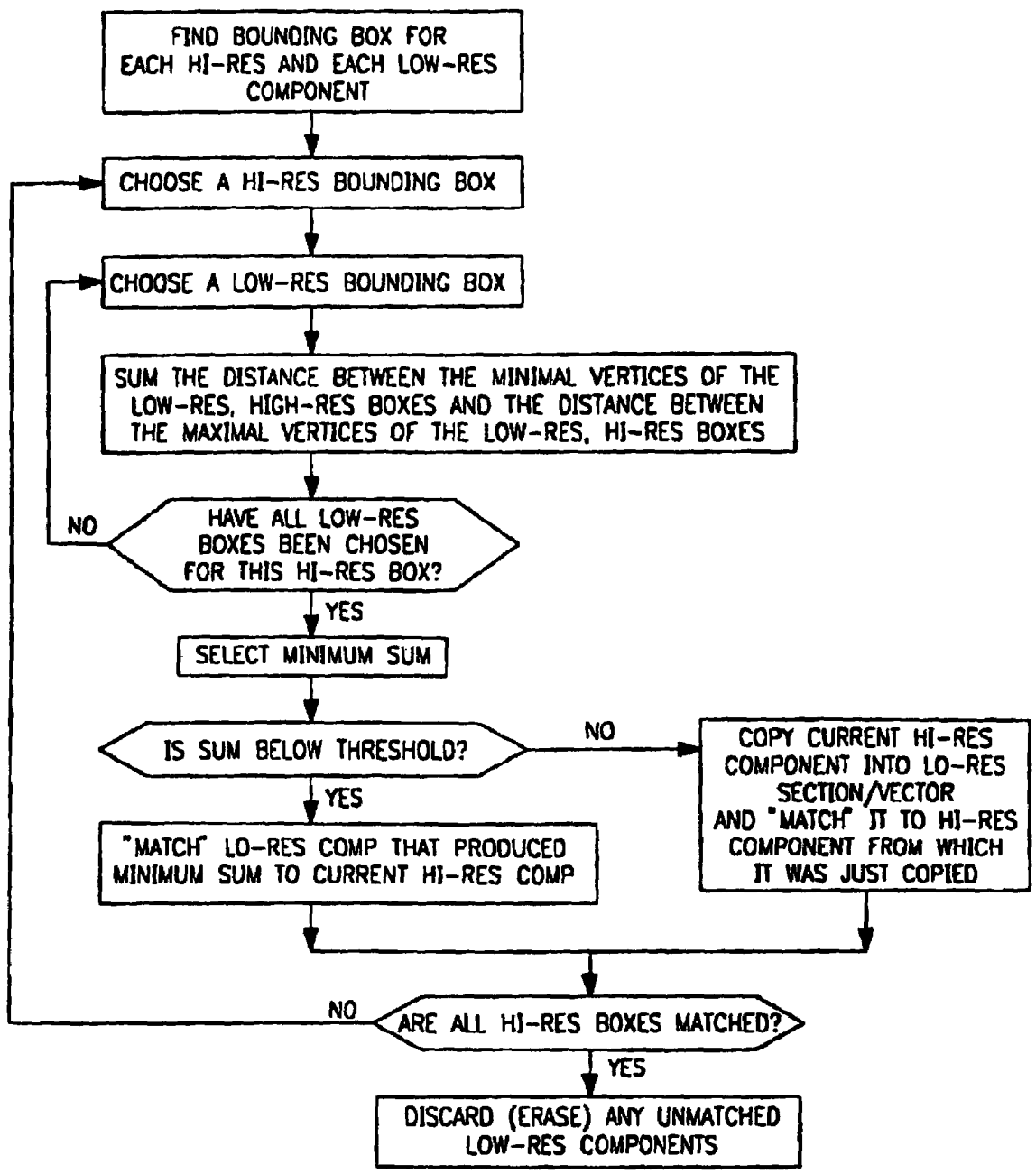
FIG. 5 is a flow chart illustrating a program for matching high-resolution and low resolution components in the manipulation of data sets of FIG. 3.

To the user, all chances made to the high resolution model appear to occur simultaneously in the low resolution model, and vice versa. However. there is not a one-to-one correlation between the different resolution models. Therefore, the computer "matches" the high resolution and low resolution components as best as it can subject to defined limits. One process for doing so is described in FIG. 5.

Automated Segmentation

The system can optionally include a segmentation subsystem that performs automatic or semi-automatic segmentation of the 3D dentition model into models of individual teeth. The segmentation subsystem is advantageously implemented as one or more computer program processes implementing a segmentation process. In alternative implementations, the segmentation process can act on the 3D volume data or on the 3D surface mesh. The segmentation process applies conventional feature detection techniques tailored to exploit the characteristics and known features of teeth. For example, feature detection algorithms generally act on images in which the features to be distinguished from each other have different colors or shades of gray. Features to be detected also usually are separated spatially from each other. However, features to be detected in a 2D or 3D image of a plaster tooth casting (e.g., the individual teeth and the gum tissue) all have the same color (white), and some features, such as an individual tooth and the surrounding gum tissue, have no spacial separation.

The segmentation process can be implemented to employ any of several feature detection techniques and advantageously uses a combination of techniques to increase the accuracy of feature identification. One feature detection technique uses color analysis to distinguish objects based on variations in color. Color analysis can be used in situations where individual teeth are separated by gaps large enough for the potting material to fill. Because the tooth casting and the potting material have contrasting colors, these teeth appear in the model as white areas separated by thin strips of black.

Another feature detection technique uses shape analysis to distinguish certain features, such as tooth from gum. In general, tooth surfaces are smooth while gum surfaces have texture, and teeth and gums typically form a U-shaped ridge where they meet. Detecting these features through shape analysis assists in distinguishing tooth from gum. Shape analysis can also detect individual teeth, for example by searching for the largest objects in the 3D image or by recognizing the cusps of a molar as four isolated patches of one color arranged in a certain pattern. One cusp-detection algorithm is described below.

Other feature detection techniques use databases of known cases or statistical information against which a particular 3D image is matched using conventional image pattern matching and data fitting techniques. One such technique, known as "Maximum a posteriori" (MAP), uses prior images to model pixel values corresponding to distinct object types (classes) as independent random variables with normal (Gaussian) distributions whose parameters (mean and variance) are selected empirically. For each class, a histogram profile is created based on a Gaussian distribution with the specified mean and variance. The prior images supply for each pixel and each class the probability that the pixel belongs to the class, a measure which reflects the relative frequency of each class. Applying Bayes' Rule to each class, the pixel values in the input image are scaled according to the prior probabilities, then by the distribution function. The result is a posterior probability that each pixel belongs to each class. The Maximum a posteriori (MAP) approach then selects for each pixel the class with the highest posterior probability as the output of the segmentation.

Another feature detection technique uses automatic detection of tooth cusps. Cusps are pointed projections on the chewing surface of a tooth. In one implementation, cusp detection is performed in two stages: (1) a "detection" stage, during which a set of points on the tooth are determined as candidates for cusp locations; and (2) a "rejection" stage, during which candidates from the set of points are rejected if they do not satisfy a set of criteria associated with cusps.

Figure 6A:
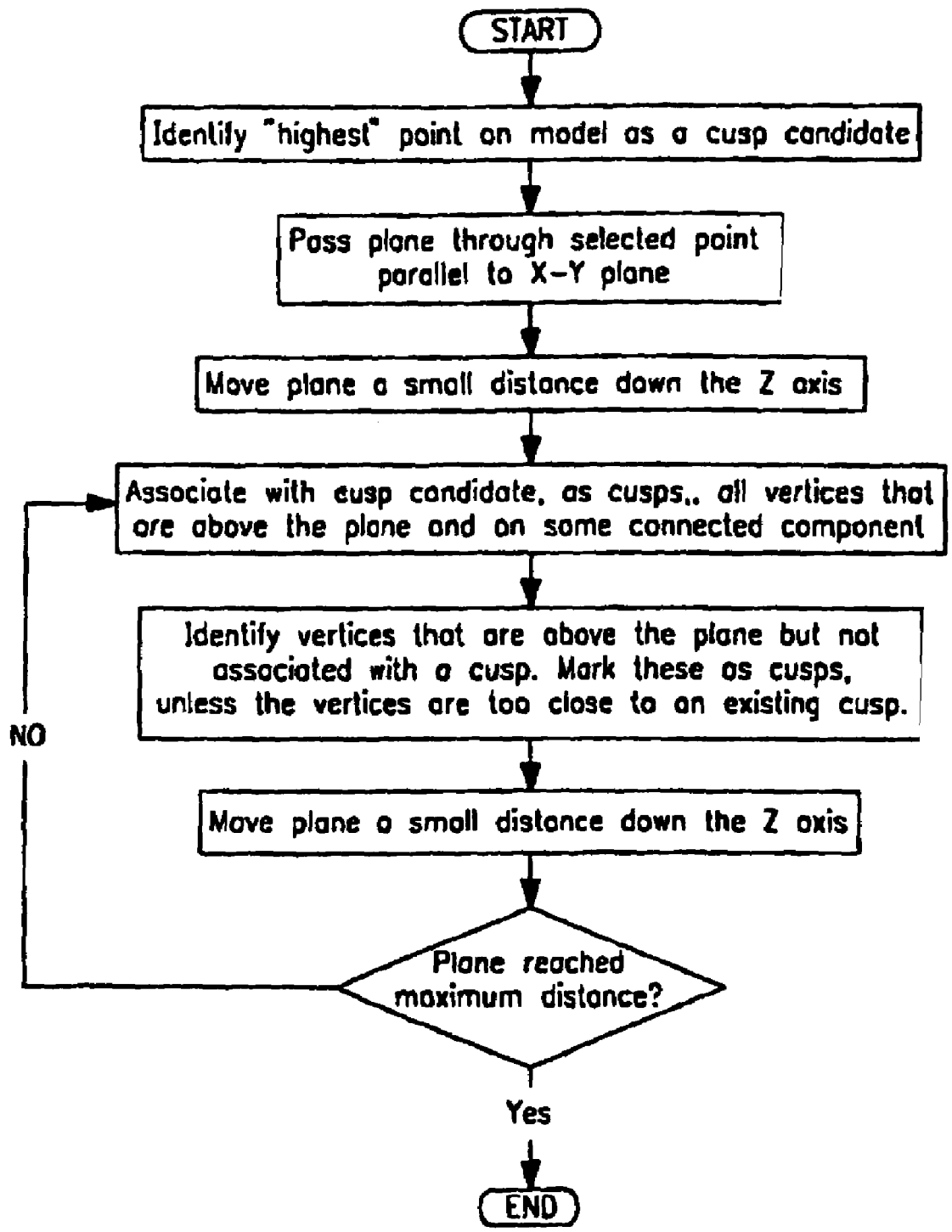
FIG. 6A is a flow chart illustrating a program for performing the "detection" stage of the cusp detection algorithm.

One process for the "detection" stage is set forth in FIG. 6A. In the detection stage, a possible cusp is viewed as an "island" on the surface of the tooth, with the candidate cusp at the highest point on the island. "Highest" is measured with respect to the coordinate system of the model, but could just as easily be measured with respect to the local coordinate system of each tooth if detection is performed after the cutting phase of treatment.

The set of all possible cusps is determined by looking for all local maxima on the tooth model that are within a specified distance of the top of the bounding box of the model. First, the highest point on the model is designated as the first candidate cusp. A plane is passed through this point, perpendicular to the direction along which the height of a point is measured. The plane is then lowered by a small predetermined distance along the Z axis. Next, all vertices connected to the tooth and which are above the plane and on some connected component are associated with the candidate cusp as cusps. This step is also referred to as the "flood fill" step. From each candidate cusp point, outward "flooding" is performed, marking each vertex on the model visited in this matter as "part of the corresponding candidate cusp. After the flood fill step is complete, every vertex on the model is examined. Any vertex that is above the plane and has not been visited by one of the flood fills is added to the list of candidate cusps. These steps are repeated until the plane is traveled a specified distance.

While this iterative approach can be more time consuming than a local maximum search, the approach described above leads to a shorter list of candidate cusps. Since the plane is lowered a finite distance at each step, very small local maxima that can occur due to noisy data are skipped over.

After the "detection" stage, the cusp detection algorithm proceeds with the "rejection" stage. One process for the "rejection" stage is set forth in FIG. 6B. In this stage, the local geometries around each of cusp candidates are analyzed to determine if they possess "non-cusplike features." Cusp candidates that exhibit "non-cusp-like features" are removed from the list of cusp candidates.

Figure 6B:
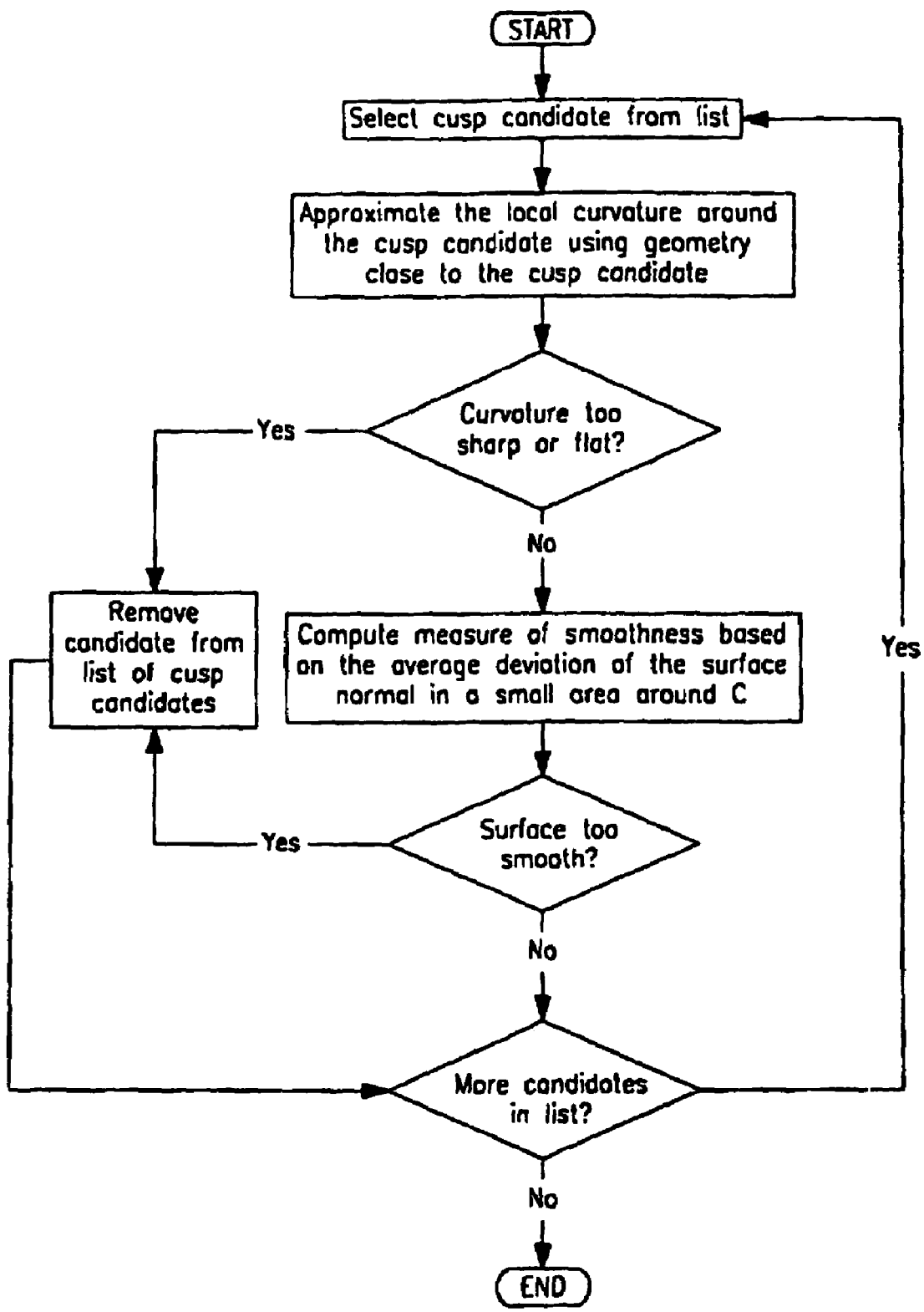
FIG. 6B is a flow chart illustrating a program for performing the "rejection" stage of the cusp detection algorithm.

Various criteria may be used to identify "non-cusp-like features." According to one test, the local curvature of the surface around the cusp candidate is used to determine whether the candidate possesses non-cusp-like features. As depicted in FIG. 6B, the local curvature of the surface around the cusp candidate is approximated and then analyzed to determine if it is too large (very pointy surface) or too small (very flat surface), in which case the candidate is removed from the list of cusp candidates. Conservative values are used for the minimum and maximum curvature values to ensure that genuine cusps are not rejected by mistake.

Under an alternative test, a measure of smoothness is computed based on the average normal in an area around the candidate cusp. If the average normal deviates from the normal at the cusp by more than a specified amount, the candidate cusp is rejected. In one embodiment, the deviation of a normal vector N from the cusp normal CN is approximated by the formula:

$$\text{deviation} = 1 - Abs(N - C),$$

which is zero at no deviation, and 1 when N and CN are perpendicular.

For both the human-assisted and automated segmentation techniques, the clinician can simplify the tooth identification process by marking the physical tooth model before the model is scanned. Upon scanning, these marks become part of the digital tooth model. The types of marks that the clinician might use include marks identifying the rotational axis of a tooth, marks identifying the principal axis of a tooth (e.g., a straight line marked on the tooth's occlusal edge), and marks identifying the boundaries between teeth. A mark identifying the rotational axis of a tooth often is used to restrict how the tooth can rotate during the course of treatment. The clinician also may wish to paint the teeth in the physical model with various colors to assist in segmenting the individual teeth from the digital tooth model.

Adding Roots and Hidden Tooth Surfaces to the Individual Tooth Models

The system can optionally be configured to add roots and hidden surfaces to the tooth models to allow more thorough and accurate simulation of tooth movement during treatment. In alternative implementations, this information is added automatically without human assistance, semi-automatically with human assistance, or manually by human operator, using a variety of data sources.

In some implementations, 2D and 3D imaging systems, such as x-ray systems, computed tomography (CT) scanners, and MRI systems, are used to gather information about the roots of the patient's teeth. For example, several 2D x-ray images of a tooth taken in different planes allow the construction of a 3D model of the tooth's roots. Information about the roots is available by visual inspection of the x-ray image and by application of a computer-implemented feature identification algorithm to the x-ray data. The system adds the roots to the tooth model by creating a surface mesh representing the roots. Physical landmarks on the patient's teeth, e.g., cavities or cusps, are extracted from the 2D and 3D data and are used to register the roots to the tooth model. Like the roots, these landmarks can be extracted manually or by use of a feature detection algorithm.

Another alternative for the addition of roots and hidden surfaces is to model typical root and crown shapes and to modify the digital model of each tooth to include a root or a hidden surface corresponding to a typical shape. This approach assumes that the roots and hidden surfaces of each patient's teeth have typical shapes. A geometric model of each typical shape is acquired, e.g., by accessing an electronic database of typical root and crown models created before the analysis of a particular patient's teeth begins.

Portions of the typical root and crown models are added to the individual tooth models as needed to complete the individual tooth models.

Yet another alternative for the addition of roots and hidden surfaces is the extrapolation of the 3D tooth model to include these features based on observed characteristics of the tooth surfaces. For example, the system can use the curvature of a particular molar between the tips of the cusps and the gumline to predict the shape of the roots for that molar. In other implementations, x-ray and CT scan data of a patient's teeth are used to provide comparison points for extrapolation of the patients roots and hidden surfaces. Models of typical root and crown shapes also can be used to provide comparison points for root and hidden surface extrapolation.

Determining the Final Tooth Positions

Once the teeth have been separated, the FDDS can be created from the IDDS. The FDDS is created by following the orthodontists' prescription to move the teeth in the model to their final positions. In one embodiment, the prescription is entered into a computer, which automatically computes the final positions of the teeth. In alternative other embodiments, a user moves the teeth into their final positions by independently manipulating one or more teeth while satisfying the constraints of the prescription. Various combinations of the above described techniques may also be used to arrive at the final tooth positions.

One method for creating the FDDS involves moving the teeth in a specified sequence. First, the centers of each of the teeth are aligned to a standard arch. Then, the teeth are rotated until their roots are in the proper vertical position. Next, the teeth are rotated around their vertical axis into the proper orientation. The teeth are then observed from the side, and translated vertically into their proper vertical position. The inclusion of roots in the tooth models, described more fully above, ensures the proper vertical orientation of the entire tooth, not just the crown. Finally, the two arches are placed together, and the teeth moved slightly to ensure that the upper, and lower arches properly mesh together. The meshing of the upper and lower arches together is visualized using a collision detection process to highlight the contacting points of the teeth in red.

Apart from its role in identifying individual teeth, cusp detection also is useful in determining final tooth orientation. For example. the cusps on a typical molar are relatively level when the tooth is oriented vertically, so the relative positions of the cusp tips indicate the tooth's position. Cusp detection therefore is incorporated into the final position determination.

One tool for use in visualizing the interaction of a patient's upper and lower teeth at the final positions is a computer-implemented "virtual" articulator. The virtual articulator provides a graphical display that simulates the operation of the patient's jaw or the operation of a conventional mechanical articulator attached to a physical model of the patient's teeth. In particular, the virtual articulator orients the digital models of the patient's upper and lower arches in the same manner that the patient's physical arches will be oriented in the patient's mouth at the end of treatment. The articular then moves the arch models through a range of motions that simulate common motions of the human jaw.

The quality of the virtual articulator's simulation depends on the types of information used to create the articulator and the tooth models. In some implementations, the virtual articulator includes a digital model of a mechanical articular created, for example, from a computer-aided drafting (CAD) file or image data gathered during a laser scan of the articulator. Other implementations include a digital model of human jaws created, for example, from 2D or 3D x-ray data, CT scan data, or mechanical measurements of the jaws, or from a combination of these types of data. In many respects, the most useful virtual articulator is the one that simulates the jaws of the patient whose teeth are being treated, which is created from image data or mechanical measurements of the patient's head.

Animation instructions define the movements that the virtual articulator simulates. Like the articulator itself, the animation instructions are derived from a variety of sources. The animation instructions associated with the simulation of a mechanical articulator require little more than a mathematical description of the motion of a mechanical hinge. A virtual articulator simulating the human jaw, on the other hand, requires a more complex set of instructions, based on human anatomical data. One method of building this set of instructions is the derivation of mathematical equations describing the common motions of an ideal human jaw. Another method is through the use of a commercially available jaw-tracking system, which contacts a person's face and provides digital information describing the motion of the lower jaw. X-ray and CT scan data also provide information indicating how the teeth and jaws relate to each other and to the rest of the person's head. Jaw-tracking systems and x-ray and CT scan data are particularly useful in developing an articulator that simulates a particular patient's anatomy.

As the virtual articulator simulates the motion of a patient's teeth, a collision detection process, such as one implementing the oriented bounding box (OBB) algorithm described below, determines whether and how the patient's teeth will collide during the normal course of oral motion. Visual indicators, such as red highlights, appear on a displayed image of the teeth to indicate collision points. The final tooth positions are adjusted, automatically or manually, to avoid collisions detected by the collision detection algorithm.

An automated system for determining final tooth positions and creating the FDDS is described in the above-mentioned U.S. patent application Ser. No. 09/169,036. That application describes a computer-implemented process for generating a set of final positions for a patient's teeth. The process involves creating an ideal model of final tooth positions based on "ideal" tooth arrangements, repositioning the individual teeth in a digital model of the patient's teeth to mimic the ideal model, and modeling the motion of the patient's jaw to perfect the final tooth arrangement.

The display and use of orthodontic-specific information also assists in the determination of final tooth positions. In some implementations, a user can elect to have malocclusion indices, such as Peer Assessment Review (PAR) metrics; shape-based metrics, or distance-based metrics, calculated and displayed with the final tooth positions. If the user is not satisfied with values of the displayed index or indices, the user can adjust the final tooth positions manually until the parameters fall within acceptable ranges. If the tooth positioning system is fully automated, the orthodontic-specific parameters are provided as feedback and used to adjust the final tooth positions until the parameters fall within acceptable ranges.

For human-assisted tooth positioning. the human user also can elect to have positioning tips displayed. Tips are available, for example, to suggest a treatment path for an individual tooth and to warn of excessive forces that might cause patient discomfort or compromise the mechanical integrity of the orthodontic appliance. Tips also are available to suggest target positions that best suit the patient's jaw structure and that ensure proper inner digitation and occlusion parameters.

Determining the Steps from the Initial to the Final Position

Figure 7:
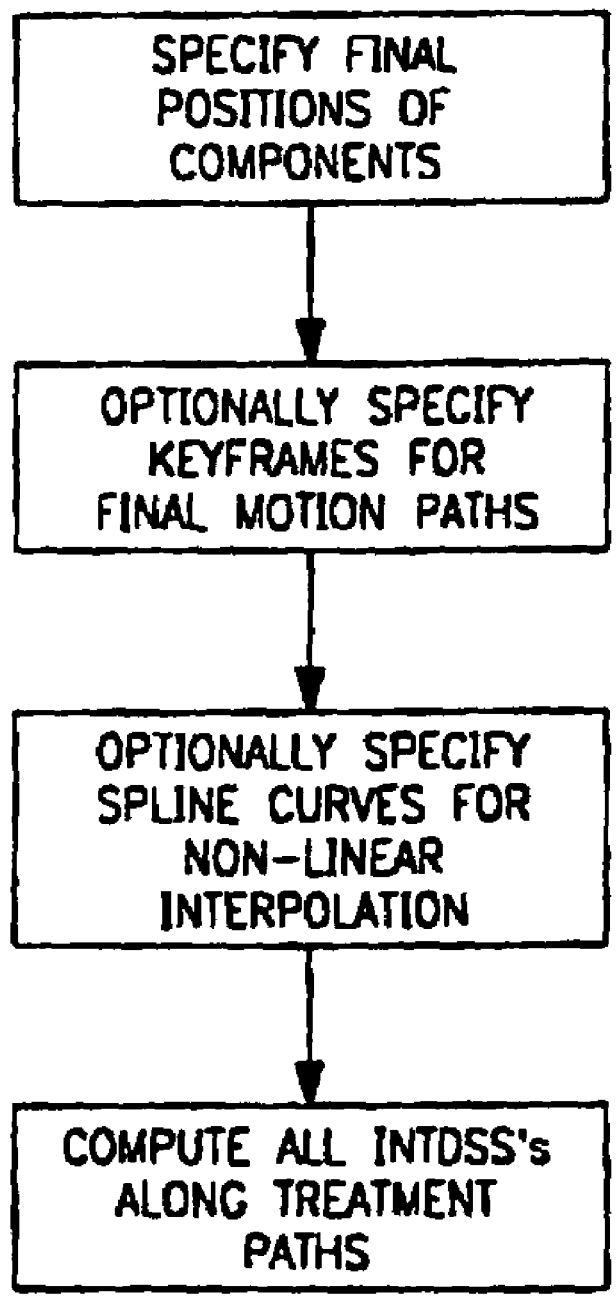
FIG. 7 illustrates a method for generating multiple intermediate digital data sets which are used for producing the adjustment appliances.

After the teeth and other components have been placed or removed to produce a model of the final tooth arrangement, it is necessary to generate a treatment plan, as illustrated in FIG. 7. The treatment plan will ultimately produce the series of INTDDS's and FDDS as described previously. To produce these data sets, it is necessary to define or map the movement of selected individual teeth from the initial position to the final position over a series of successive steps. In addition, it may be necessary to add other features to the data sets in order to produce desired features in the treatment appliances. For example, it may be desirable to add wax patches to the image in order to define cavities or recesses for particular purposes, such as to maintain a space between the appliance and particular regions of the teeth or jaw in order to reduce soreness of the gums, avoid periodontal problems, allow for a cap, and the like. Additionally, it will often be necessary to provide a receptacle or aperture intended to accommodate an anchor which is to be placed on a tooth in order to permit the tooth to be manipulated in a manner that requires the anchor, e.g., to be lifted relative to the jaw.

Accounting for Physical Constraints and Additions to the Model

Some methods for manufacturing the tooth repositioning appliances require that the separate, repositioned teeth and other components be unified into a single continuous structure in order to permit manufacturing. In these instances, "wax patches are used to attach otherwise disconnected components of the INTDDS's. These patches are added to the data set underneath the teeth and above the gum so that they do not effect the geometry of the tooth repositioning appliances. The application software provides for a variety of wax patches to be added to the model, including boxes and spheres with adjustable dimensions. The wax patches that are added are treated by the software as additional pieces of geometry, identical to all other geometries. Thus, the wax patches can be repositioned during the treatment path, as can the teeth and other components. One method of separating the teeth using vertical coring, as described above, removes the need for most of these "wax patches".

In the manufacturing process, adding a wax patch to the graphic model will generate a positive mold that has the same added wax patch geometry. Because the mold is a positive of the teeth and a polymeric appliance is a negative of the teeth, when the appliance is formed over the mold, the appliance will also form around the wax patch that has been added to the mold. When placed in the patient's mouth, the appliance will thus allow for a space between the inner cavity surface of the appliance and the patient's teeth or gums. Additionally, the wax patch may be used to form a recess or aperture within the appliance which engages an anchor placed on the teeth in order to move the tooth in directions which could not otherwise be accomplished.

For some patients an optimal treatment plan requires the interaction of aligners with tooth attachments, such as brackets and anchors, to ensure proper orthodontic correction in a reasonable amount of time. In these situations, the aligners must grip the attachments to ensure that the proper force is exerted on the patient's teeth. For example, an aligner may be designed to grip an anchor planted in the patient's jaw to move the patient's teeth back in the jaw. Likewise, an aligner may grip a bracket attached to a patient's tooth to increase the aligner's leverage or grip on the tooth.

The creation of digital attachment models allows the system to model the effects of attachments in analyzing the digital model of a patient's teeth. Each attachment model represents a physical attachment that may be placed in a patient's mouth, generally on a tooth, during the course of treatment. Many attachments, such as conventional brackets, are available in standard shapes and sizes, the models of which can be selected from a library of virtual attachments and added to a patient's tooth model. Other attachments are patient-specific and must be modeled by the user for inclusion in the digital tooth model. The presence of virtual attachments in a patient's tooth model ensures that the aligners fabricated for the patient's treatment plan will accommodate the corresponding physical attachments placed in the patient's mouth during treatment.

The wax patches and virtual attachments described above, and individual components of the tooth model, can be reduced or enlarged in size, which will result in a manufactured appliance having a tighter or looser fit.

Selecting the Intermediate Treatment Stages

Number of Treatment Stages:

The user can change the number of desired treatment stases from the initial to the target states of the teeth. Any component that is not moved is assumed to remain stationary, and thus its final position is assumed to be the same as the initial position (likewise for all intermediate positions, unless one or more key frames are defined for that component).

Key Frames:

The user may also specify "key frames" by selecting an intermediate state and making changes to component position(s). In some embodiments, unless instructed otherwise, the software automatically linearly interpolates between all user-specified positions (including the initial position, all key frame positions, and the target position). For example, if only a final position is defined for a particular component, each subsequent stage after the initial stage will simply show the component an equal linear distance and rotation (specified by a quaternion) closer to the final position. If the user specifies two key frames for that component, the component will "move" linearly from the initial position through different stages to the position defined by the first key frame. It will then move, possibly in a different direction, linearly to the position defined by the second key frame. Finally, it will move, possibly in yet a different direction, linearly to the target position.

These operations may be done independently to each component, so that a key frame for one component will not affect another component, unless the other component is also moved by the user in that key frame. One component may accelerate along a curve between one pair of stages (e.g., stages 3 and 8 in a treatment plan having that many stages), while another moves linearly between another pair of stages (e.g., stages 1 to 5), and then changes direction suddenly and slows down along a linear path to a later stage (e.g., stage 10). This flexibility allows a great deal of freedom in planning a patient's treatment.

In some implementations, non-linear interpolation is used instead of or in addition to linear interpolation to construct a treatment path among key frames. In general. a non-linear path such as a spline curt e. created to tit among selected points is shorter than a path formed from straight line segments connecting the points. A "treatment path" describes the transformation curve applied to a particular tooth to move the tooth from its initial position to its final position. A typical treatment path includes some combination of rotational and translational movement of the corresponding tooth, as described above.

Figure 15A:
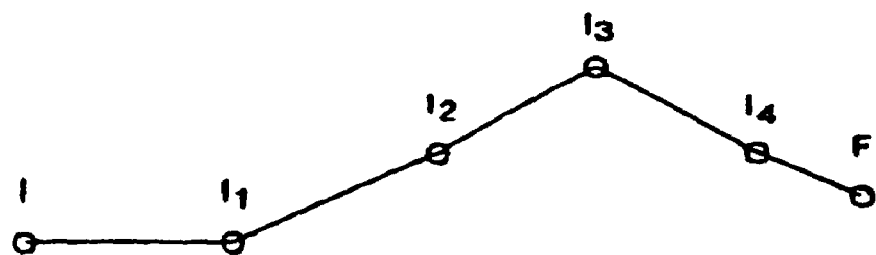
FIGS. 15A, 15B, and 15C illustrate the positioning of teeth at various steps of an orthodontic treatment plan.
Figure 15B:
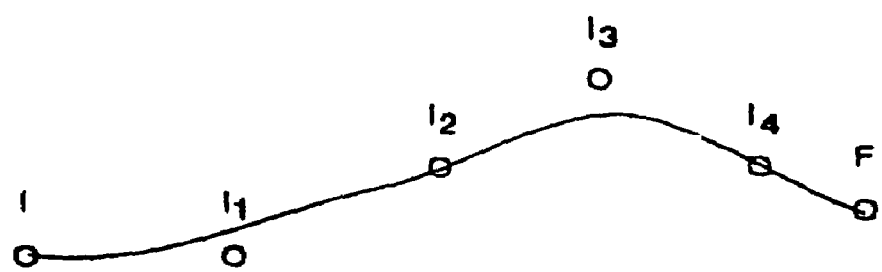

FIGS. 15A and 15B show a linearly interpolated treatment path and a non-linearly interpolated path. respectively, connecting an initial tooth position I to a final tooth position F. The linearly interpolated path consists of straight line segments connecting the initial and final tooth positions as well as the four intermediate tooth positions $I_1$, $I_2$, $I_3$, $I_4$. The non-linear interpolated path consists of a curved line fitted among the intermediate tooth positions. The curved path can be formed using a conventional spline-curve fitting algorithm.

Figure 16:
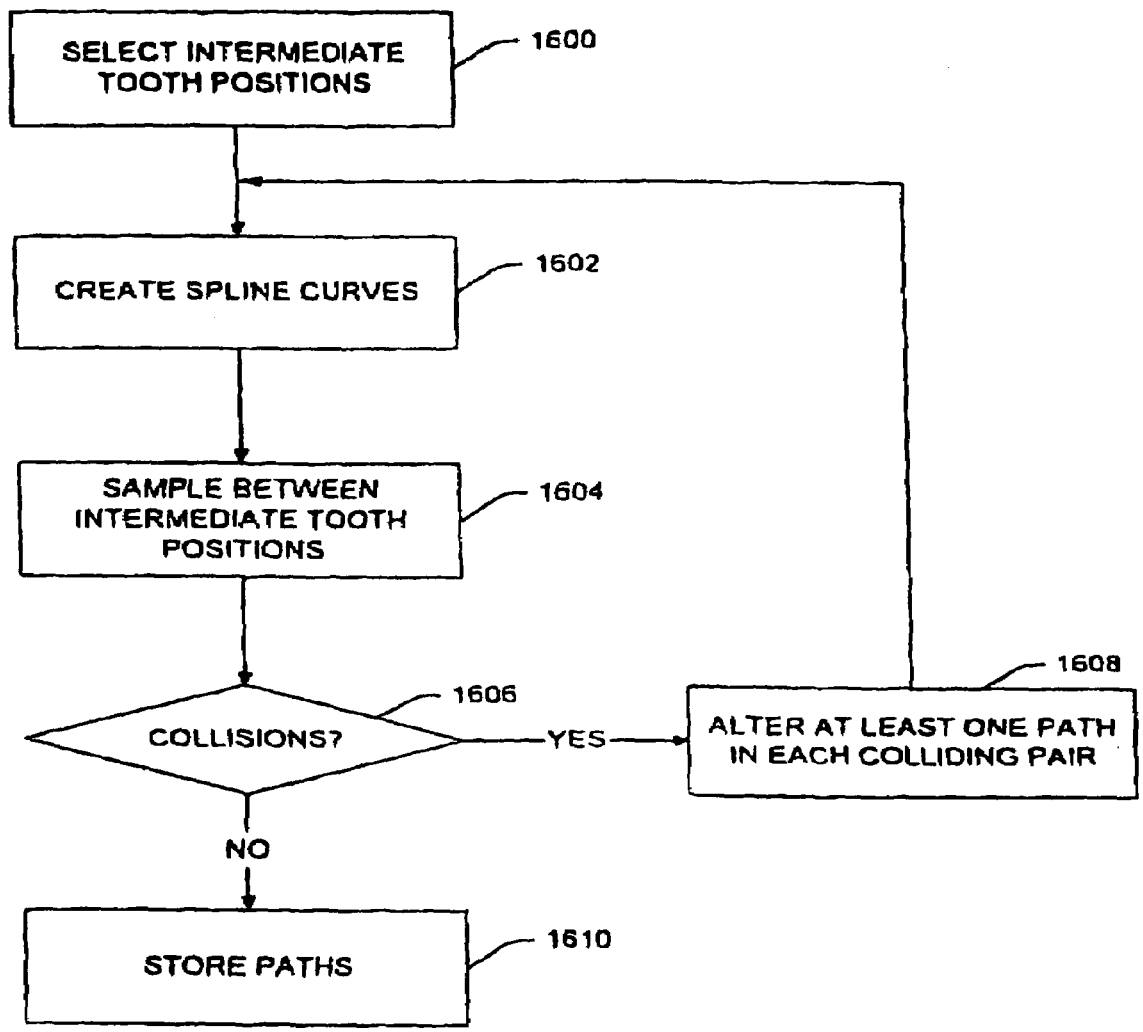
FIG. 16 is a flow chart of a process for determining a tooth's path among intermediate positions during an orthodontic treatment plan.

FIG. 16 is a flow chart of a computer-implemented process for generating non-linear treatment paths along which a patient's teeth will travel during treatment. The non-linear paths usually are generated automatically by computer program, in some cases with human assistance. The program receives as input the initial and final positions of the patient's teeth and uses this information to select intermediate positions for each tooth to be moved (step 1600). The program then applies a conventional spline curve calculation algorithm to create a spline curve connecting each tooth's initial position to the tooth's final position (step 1602). In many situations, the curve is constrained to follow the shortest path between the intermediate positions. The program then samples each spline curve between the intermediate positions (step 1604) and applies the collision detection algorithm to the samples (step 1606). If any collisions are detected, the program alters the path of at least one tooth in each colliding pair by selecting a new position for one of the intermediate steps (step 1603) and creating a new spline curve (1602). The program then samples the new path (1604) and again applies the collision detection algorithm (1606). The program continues in this manner until no collisions are detected. The routine then stores the paths, e.g., by saving the coordinates of each point in the tooth at each position on the path in an electronic storage device, such as a hard disk (step 1610).

Figure 15C:
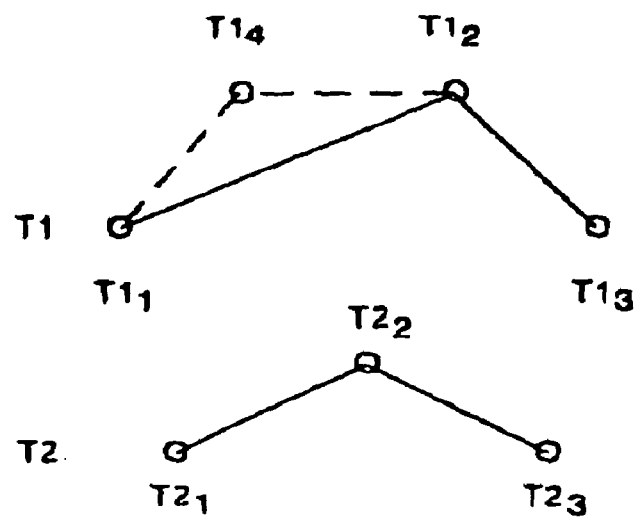

The path-generating program, whether using linear or non-linear interpolation, selects the treatment positions so that the tooth's treatment path has approximately equal lengths between each adjacent pair of treatment steps. The program also avoids treatment positions that force portions of a tooth to move with more than a given maximum velocity. FIG. 15C shows a tooth that is scheduled to move along a first path T1 from an initial position $T1_1$; to a final position $T1_3$, through an intermediate position $T1_2$, which lies closer to the final position $T1_3$. Another tooth is scheduled to move along a shorter path T2 from an initial position $T2_1$ to a final position $T2_3$; through an intermediate position $T2_2$, which is equidistant from the initial and final positions $T2_1$, $T2_3$. In this situation, the program may choose to insert a second intermediate position $T1_4$ along the first path T1 that is approximately equidistant from the initial position $T1_1$ and the intermediate position $T1_2$ and that is separated from these two positions by approximately the same distance that separates the intermediate position $T1_2$ from the final position $T1_3$.

Altering the first path T1 in this manner ensures that the first tooth will move in steps of equal size. However, altering the first path T1 also introduces an additional treatment step having no counterpart in the second path T2. The program can respond to this situation in a variety of ways, such as by allowing the second tooth to remain stationary during the second treatment step (i.e., as the first tooth moves from one intermediate position $T1_4$ to the other intermediate position $T1_3$) or by altering the second path T2 to include four equidistant treatment positions. The program determines how to respond by applying a set of orthodontic constraints that restrict the movement of the teeth.

Orthodontic constraints that may be applied by the path-generating program include the minimum and maximum distances allowed between adjacent teeth at any given time, the maximum linear or rotational velocity at which a tooth should move, the maximum distance over which a tooth should move between treatment, steps, the shapes of the teeth, the characteristics of the tissue and bone surrounding the teeth (e.g., ankylose teeth cannot move at all), and the characteristics of the aligner material (e.g., the maximum distance that the aligner can move a given tooth over a given period of time). For example, the patient's age and jaw bone density may dictate certain "safe limits" beyond which the patient's teeth should not forced to move. In general, a gap between two adjacent, relatively vertical and non-tipped central and lateral teeth should not close by more than about 1 mm every seven weeks. The material properties of the orthodontic appliance also limit the amount by which the appliance can move a tooth. For example, conventional retainer materials usually limit individual tooth movement to approximately 0.5 mm between treatment steps. The constraints have default values that apply unless patient-specific values are calculated or provided by a user. Constraint information is available from a variety of sources, including text books and treating clinicians.

In selecting the intermediate positions for each tooth, the path-generating program invokes the collision detection program to determine whether collisions will occur along the chosen paths. The program also inspects the patient's occlusion at each treatment step along the path to ensure that the teeth align to form an acceptable bite throughout the course of treatment. If collisions or an unacceptable bite will occur, or if a required constraint cannot be satisfied, the program iteratively alters the offending tooth path until all conditions are met. The virtual articulator described above is one tool for testing bite occlusion of the intermediate treatment positions.

Figure 17:
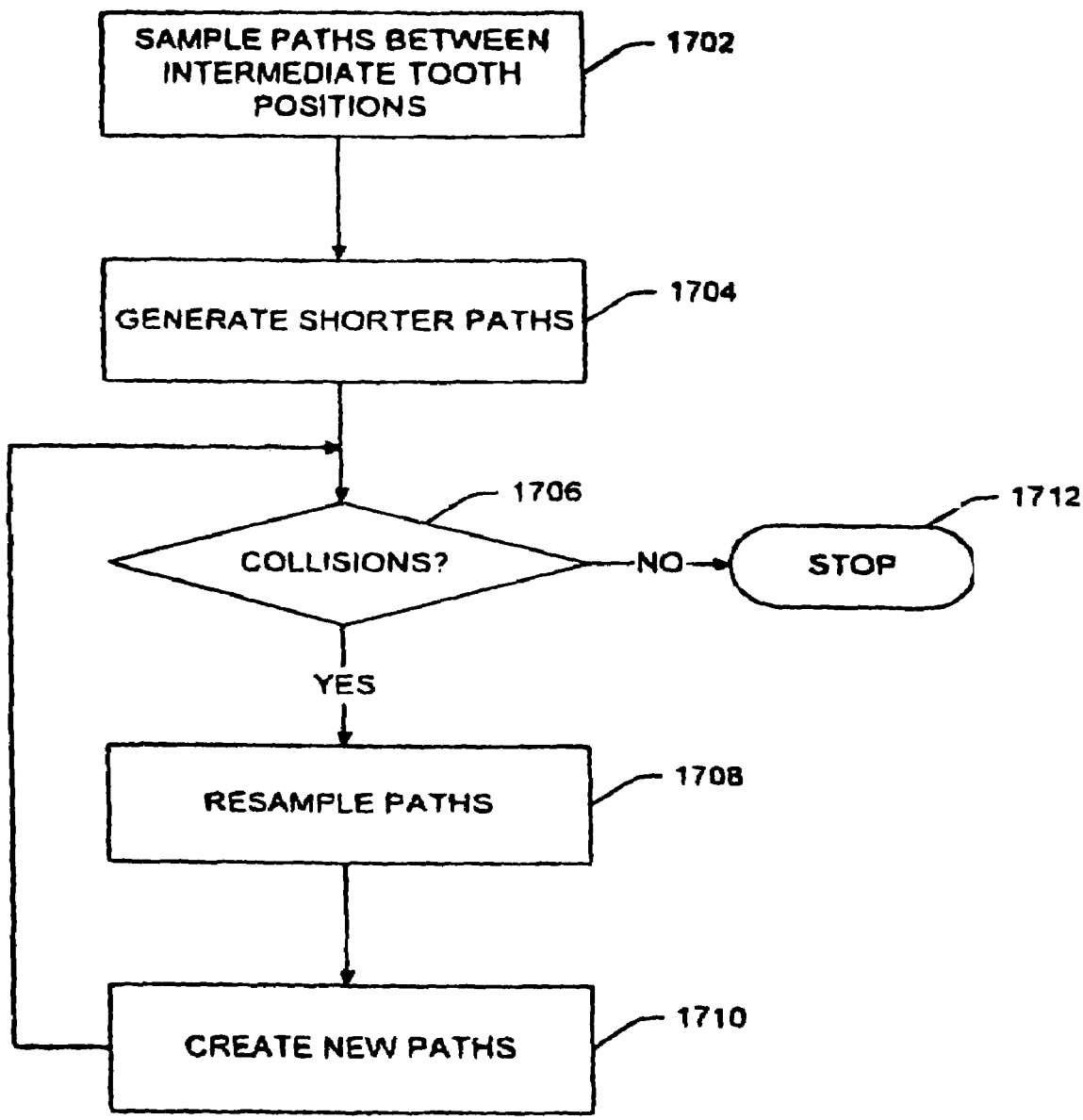
FIG. 17 is a flow chart of a process for optimizing the path of a tooth from an initial position to a final position during an orthodontic treatment plan.

As shown in FIG. 17, once the path-generating program has established collision-free paths for each tooth to be moved, the program calls an optimization routine that attempts to make the transformation curve for each tooth between the initial and final positions more linear. The routine begins by sampling each treatment path at points between treatment steps (step 1702), e.g., by placing two sample points between each treatment step, and calculating for each tooth a more linear treatment path that fits among the sample points (step 1704). The routine then applies the collision detection algorithm to determine whether collisions result from the, altered paths (step 1706). If so, the routine resamples the altered paths (step 1708) and then constructs for each tooth an alternative path among the samples (step 1710). The routine continues in this manner until no collisions occur (step 1712).

In some embodiments, as alluded to above, the software automatically computes the treatment path, based upon the IDDS and the FDDS. This is accomplished using a path scheduling algorithm which determines the rate at which each component, i.e., each tooth, moves along the path from the initial position to the final position. The path scheduling algorithm determines the treatment path while avoiding "round-tripping," i.e., while avoiding moving a tooth along a distance greater than absolutely necessary to straighten the teeth. Such motion is highly undesirable, and has potential negative effects on the patient.

One implementation of the path scheduling algorithm attempts first to schedule or stage the movements of the teeth by constraining each tooth to the most linear treatment path between the initial and final positions. The algorithm then resorts to less direct routes to the final positions only if collisions will occur between teeth along the linear paths or if mandatory constraints will be violated. The algorithm applies one of the path-generation processes described above, if necessary, to construct a path for which the intermediate treatment steps do not lie along a linear transformation curve between the initial and final positions. Alternatively, the algorithm schedules treatment paths by drawing upon a database of preferred treatments for exemplary tooth arrangements. This database can be constructed over time by observing various courses of treatment and identifying the treatment plans that prove most successful with each general class of initial tooth arrangements. The path scheduling algorithm can create several alternative paths and present each path graphically to the user. The algorithm provides as output the path selected by the user.

In other implementations, the path scheduling algorithm utilizes a stochastic search technique to find an unobstructed path through a configuration space which describes possible treatment plans. One approach to scheduling motion between two user defined global key frames is described below. Scheduling over a time interval which includes intermediate key frames is accomplished by dividing the time interval into subintervals which do not include intermediate key frames, scheduling each of these intervals independently, and then concatenating the resulting schedules.

Figure 8A:
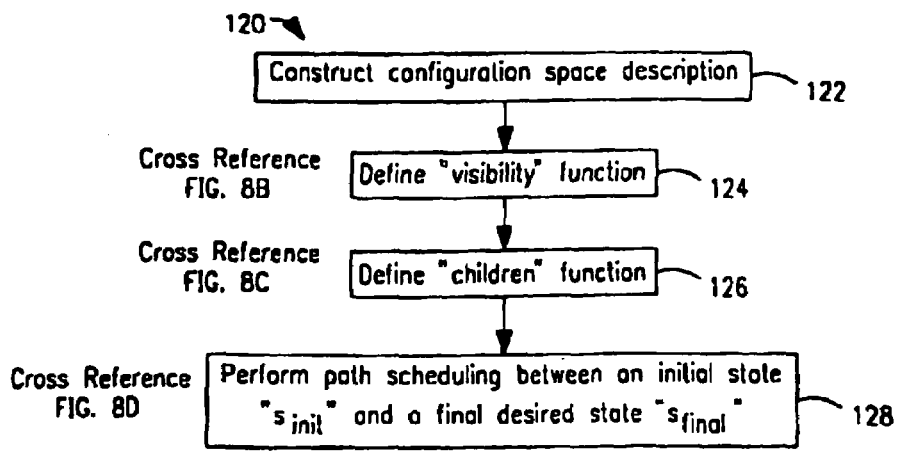
FIG. 8A is a flow chart illustrating the steps performed by the path scheduling algorithm.

Flow chart 120 in FIG. 8A depicts a simplified path scheduling algorithm. As shown in FIG. 8A, first step 122 involves construction of the "configuration space" description. A "configuration," in this context, refers to a given set of positions of all the teeth being considered for movement. Each of these positions may be described in multiple ways. In a common implementation, the positions are described by one affine transformation to specify change in location and one rotational transformation to specify the change in orientation of a tooth from its initial position to its final position. The intermediate positions of each tooth are described by a pair of numbers which specify how far to interpolate the location and orientation between the two endpoints. A "configuration" thus consists of two numbers for each tooth being moved, and the "configuration space" refers to the space of all such number pairs. Thus, the configuration space is a Cartesian space, any location in which can be interpreted as specifying the positions of all teeth.

The affine transformation describing the movement of each tooth from its starting position to its ending position is decomposed into translational and rotational components; these transformations are independently interpolated with scalar parameters which are considered two dimensions of the configuration space. The entire configuration space thus consists of two dimensions per moved tooth, all of which are treated equivalently during the subsequent search.

The configuration space is made of "free space" and "obstructed space." "Free" configurations are those which represent valid, physically realizable positions of teeth, while "obstructed" configurations are those which do not. To determine whether a configuration is free or obstructed, a model is created for the positions of the teeth which the configuration describes. A collision detection algorithm is then applied to determine if any of the geometries describing the tooth surfaces intersect. If there are no obstructions, the space is considered free; otherwise it is obstructed. Suitable collision detection algorithms are discussed in more detail below.

Figure 8B:
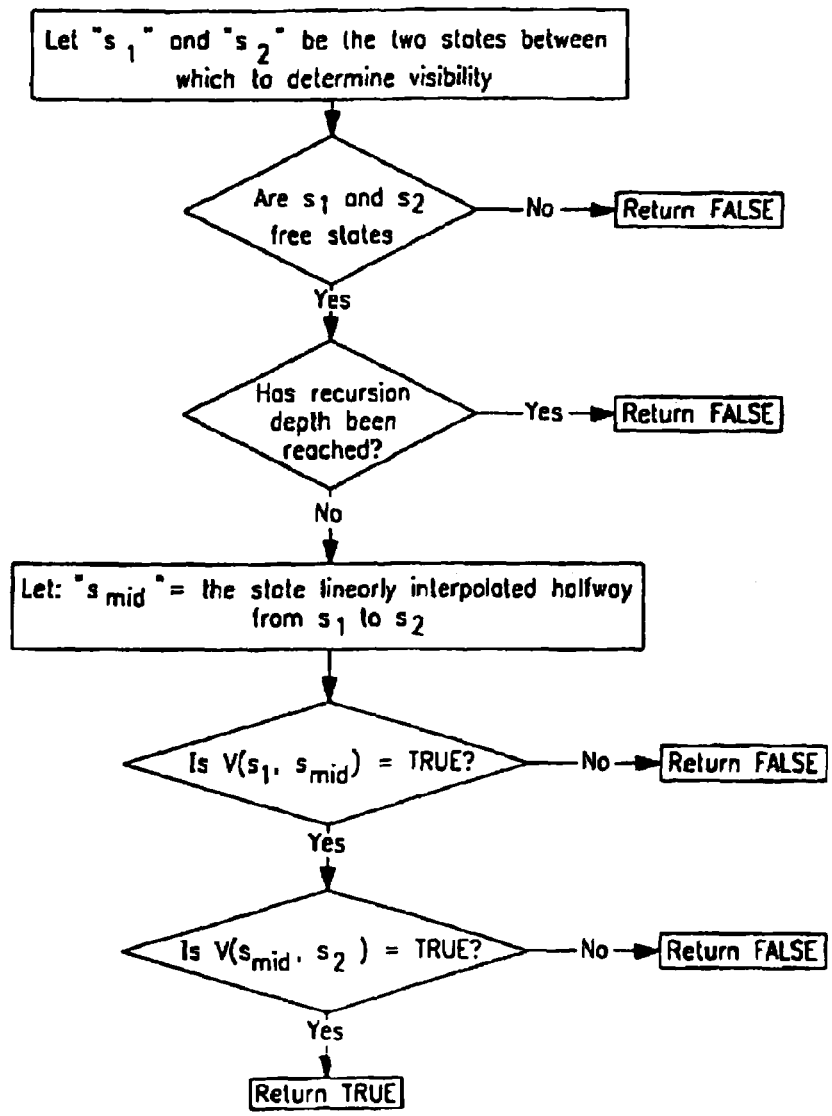
FIG. 8B is a flow chart illustrating the steps for performing a "visibility" function.

At step 124, a "visibility" function $V(s_1, s_2)$ is defined which takes two vectors in the configuration space, "$s_1$" and "$s_2$", as input and returns a true or false boolean value. The visibility function returns a true value if and only if a straight line path connecting $s_1$ and $s_2$ passes entirely through a free and unobstructed region of the configuration space. One process for carrying out the visibility function is set forth in FIG. 8B. The visibility function is approximately computed by testing the teeth model for interferences at discretely sampled points along the line $s_1$–$s_2$. Techniques such as early termination on failure and choosing the order of sample points by recursively subdividing the interval to be tested, may be used to increase the efficiency of the visibility function.

Figure 8C:
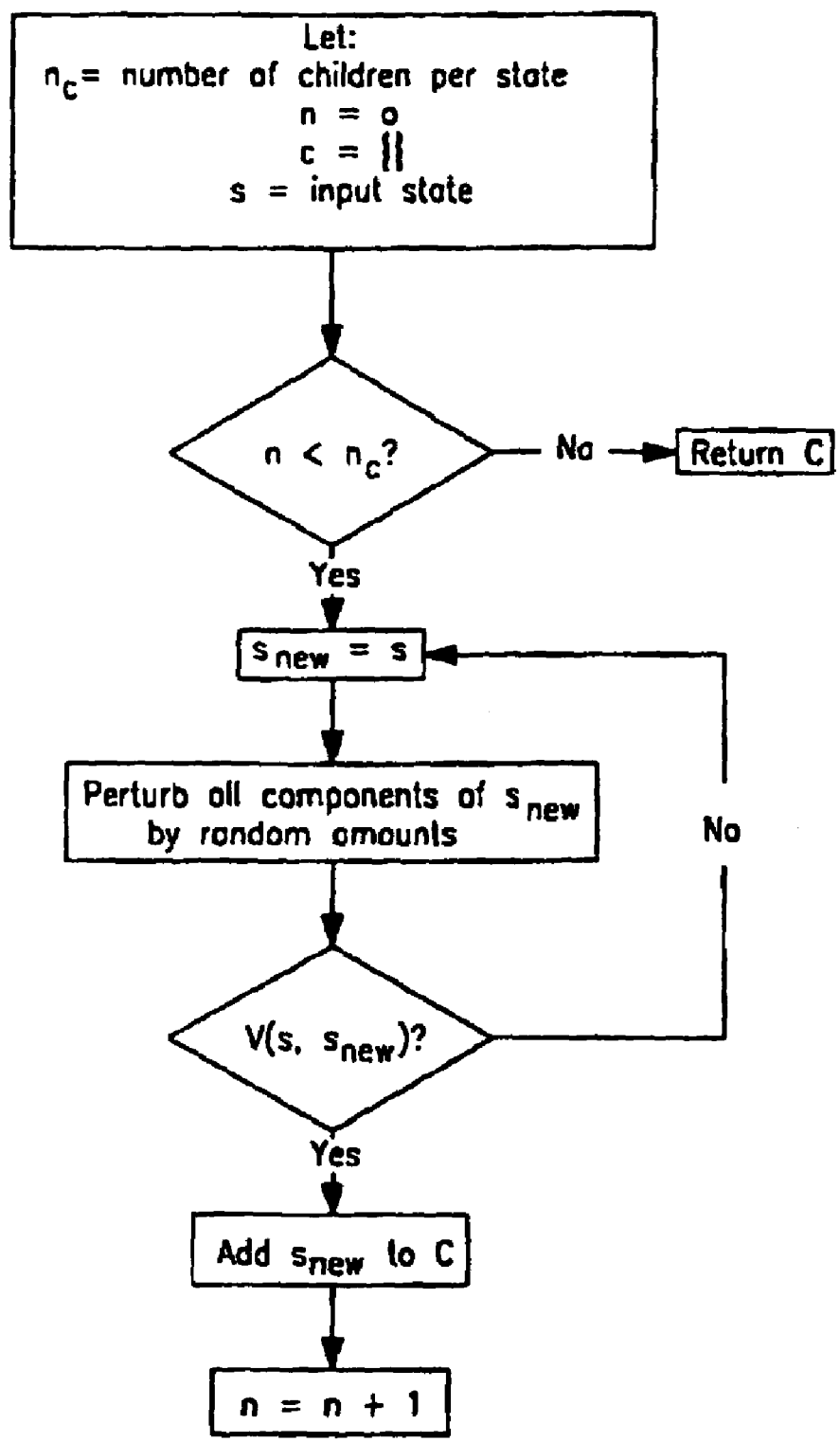
FIG. 8C is a flow chart illustrating the steps for performing a "children" function.

At step 126 of FIG. 8A, a "children" function C(s) is defined whose input parameter; "s", is a vector in the configuration space and which returns a set of vectors "$s_c$" in the configuration space. FIG. 8C depicts a simplified flow chart illustrating the steps followed for computing children function C(s). Each vector within set sc satisfies the property that $V(s, s_c)$ is true and that each of its components are greater than or equal to the corresponding component of "s." This implies that any state represented by such a vector is reachable from "s" without encountering any interferences and without performing any motion which is not in the direction prescribed by treatment. Each vector of set "$s_c$" is created by perturbing each component of "s" by some random, positive amount. The visibility function $V(s, s_c)$ is then computed and "s" added to the set "$s_c$" if the visibility function returns a true boolean value. Additionally, for each such vector generated, a pointer to its parent "s" is recorded for later use.

Figure 8D:
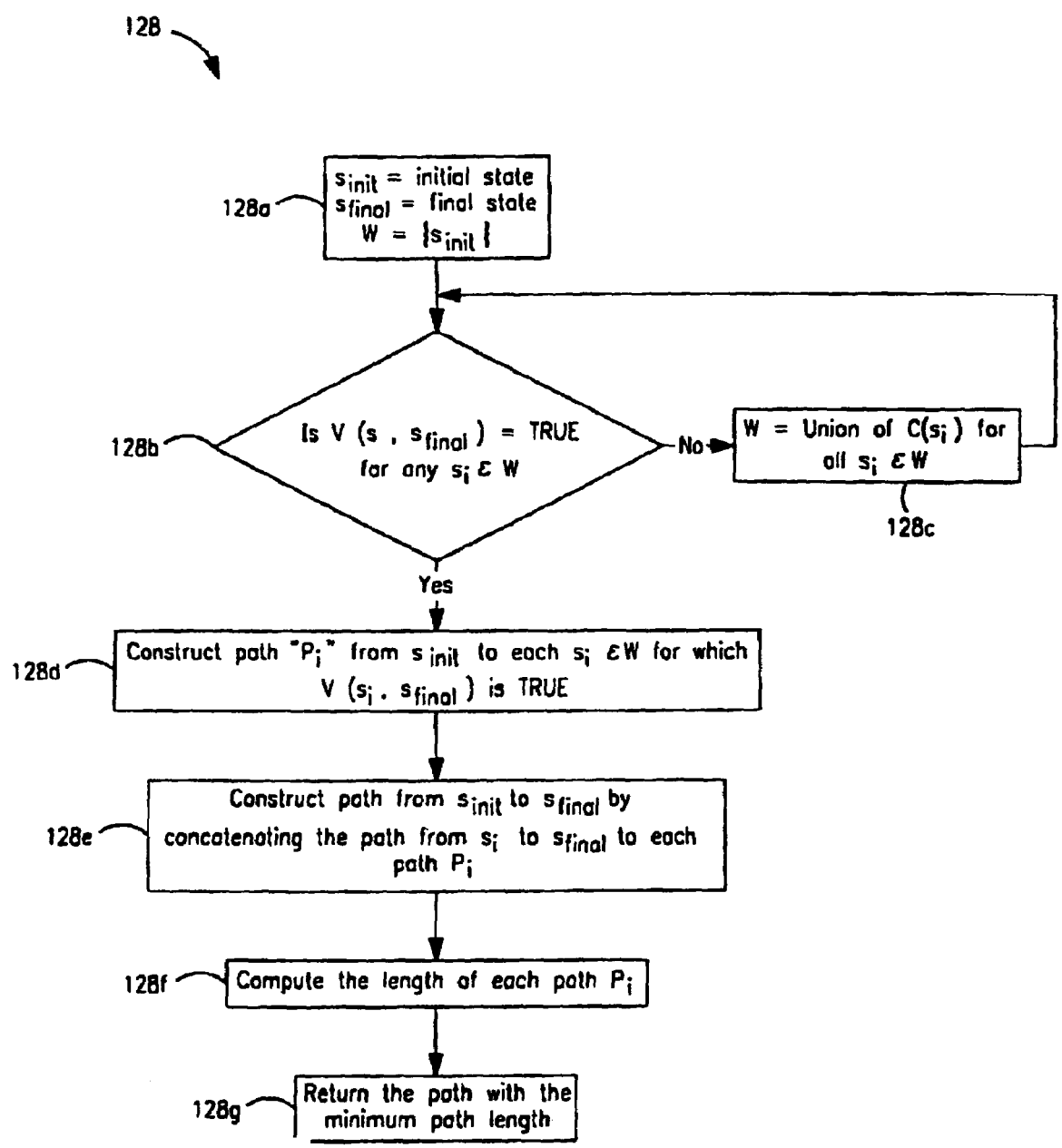
FIG. 8D is a flow chart illustrating the steps for performing path scheduling step 128 of FIG. 8A.

After the configuration space has been defined, at step 128, path scheduling is performed between an initial state "$s_{init}$" and a final state "$s_{final}$". FIG. 8D depicts a flow chart for performing step 128 depicted in FIG. 8A. As illustrated in FIG. 8D, at step 128a, a set of states "W" is defined to initially contain only the initial state $s_{init}$. Next. at step 128b, the visibility function is invoked to determine if $V(s, s_{final})$ is true for at least one state $s_i$ in W. If the visibility function returns a false boolean value, at step 128c, the set of states "W" is replaced with the union of $C(s_i)$ for all $s_i$ in W. Steps 128b and 128c are repeated until $V(s_i, s_{final})$ returns a true boolean value for any $s_i$ belonging to W.

At step 128d, for each $s_i$ for which $V(s_i, s_{final})$ is true, an unobstructed path $P_i$ is constructed from $s_i$ to $s_{init}$ by following the parent pointers back to $s_{init}$. At step 128e, the path from $s_{init}$ to $s_{final}$ is then constructed by concatenating the paths $P_i$ with the final step from $s_i$ to $s_{final}$. If there are multiple paths from $s_{init}$ to $s_{final}$, the total length of each path is computed at step 128f. Finally, at step 128g, the path with the shortest length is then chosen as the final path. The length of the chosen path corresponds to the total time and stages required for a treatment plan.

The resulting final path consists of a series of vectors, each of which represents a group of values of the interpolation parameters of the translational and rotational components of the transformations of the moving teeth. Taken together, these constitute a schedule of tooth movement which avoids tooth-to-tooth interferences.

A collision or interference detection algorithm employed in one embodiment is based on the algorithm described in SIGGRAPH article, Stefan Gottschalk et al. (1996): "*OBBTree: A Hierarchical Structure for Rapid Interference*

*Detection.*" The contents of the SIGGRAPH article are herein incorporated by reference.

The algorithm is centered around a recursive subdivision of the space occupied by an object, which is organized in a binary-tree like fashion. Triangles are used to represent the teeth in the DDS. Each node of the tree is referred to as an oriented bounding boat (OBB) and contains a subset of triangles appearing in the node's parent. The children of a parent node contain between them all of the triangle data stored in the parent node.

Figure 9A:
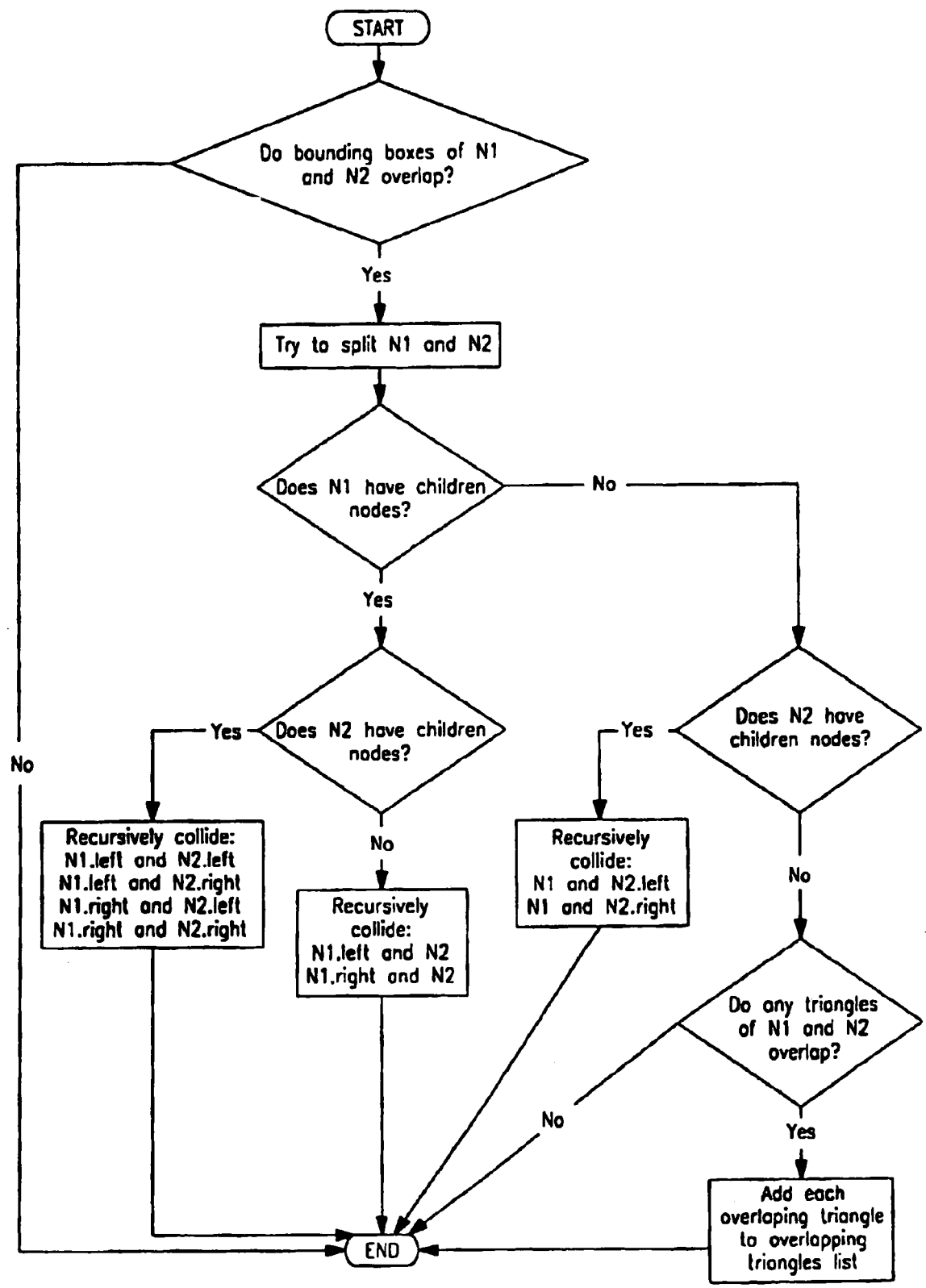
FIG. 9A is a flow chart illustrating the steps for performing recursive collision testing during collision detection.

The bounding box of a node is oriented so it tightly fits around all of the triangles in that node. Leaf nodes in the tree ideally contain a single triangle, but can possibly contain more than one triangle. Detecting collisions between two objects involves determining if the OBB trees of the objects intersect. FIG. 9A sets forth a flow chart depicting a simplified version of a recursive collision test to check if a node "N1" from a first object intersects with node "N2" of a second object. If the OBBs of the root nodes of the trees overlap, the root's children are checked for overlap. The algorithm proceeds in a recursive fashion until the leaf nodes are reached. At this point, a robust triangle intersection routine is used to determine if the triangles at the leaves are involved in a collision.

Figure 9B:
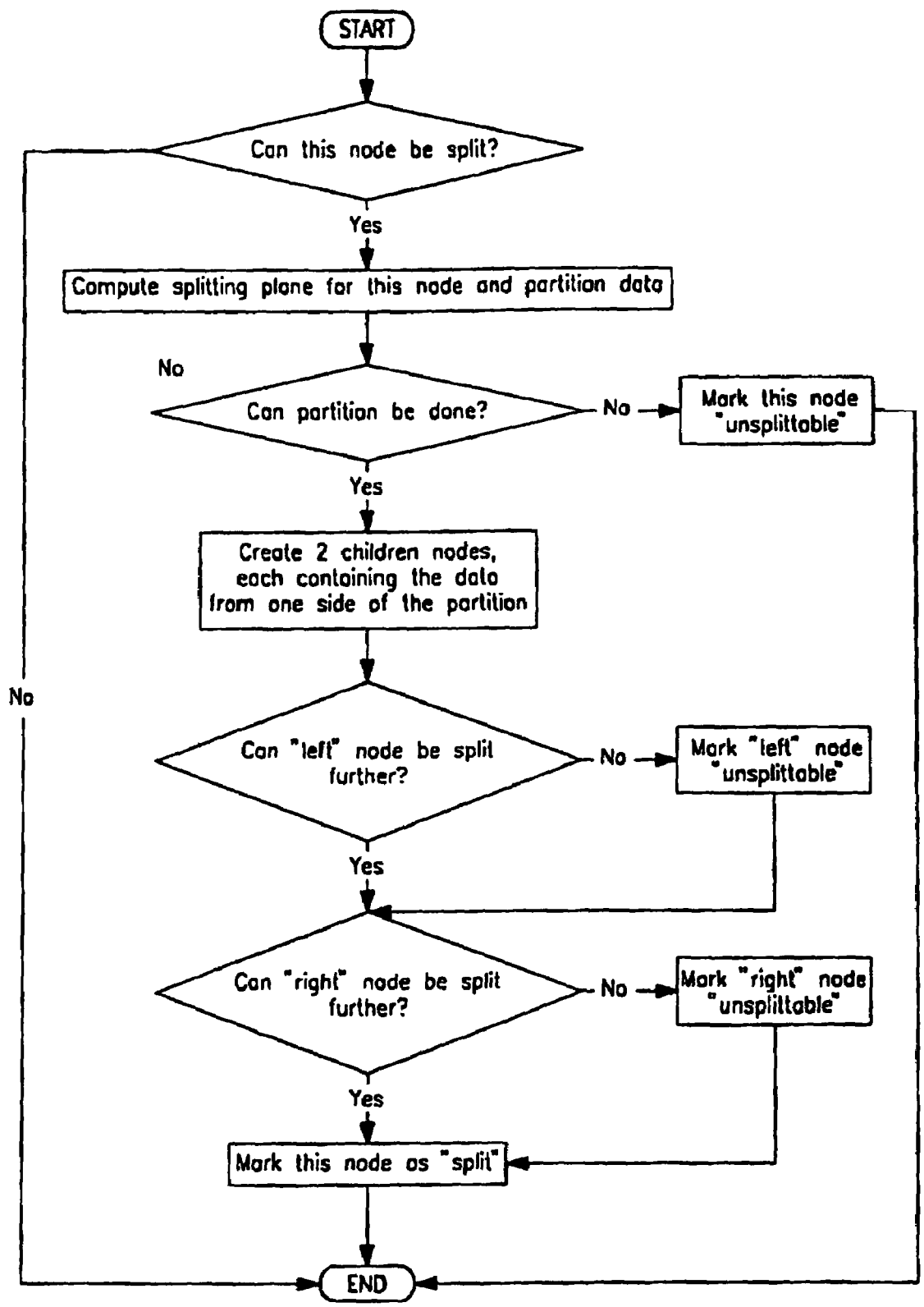
FIG. 9B is a flow chart illustrating node splitting performed during collision detection.

The collision detection technique described here provides several enhancements to the collision detection algorithm described in the SIGGRAPH article. For example, OBB trees can be built in a lazy fashion to save memory and time. This approach stems from the observation that some parts of the model will never be involved in a collision, and consequently the OBB tree for such parts of the model need not be computed. The OBB trees are expanded by splitting the internal nodes of the tree as necessary during the recursive collision determination algorithm, as depicted in FIG. 9B.

Figure 9C:
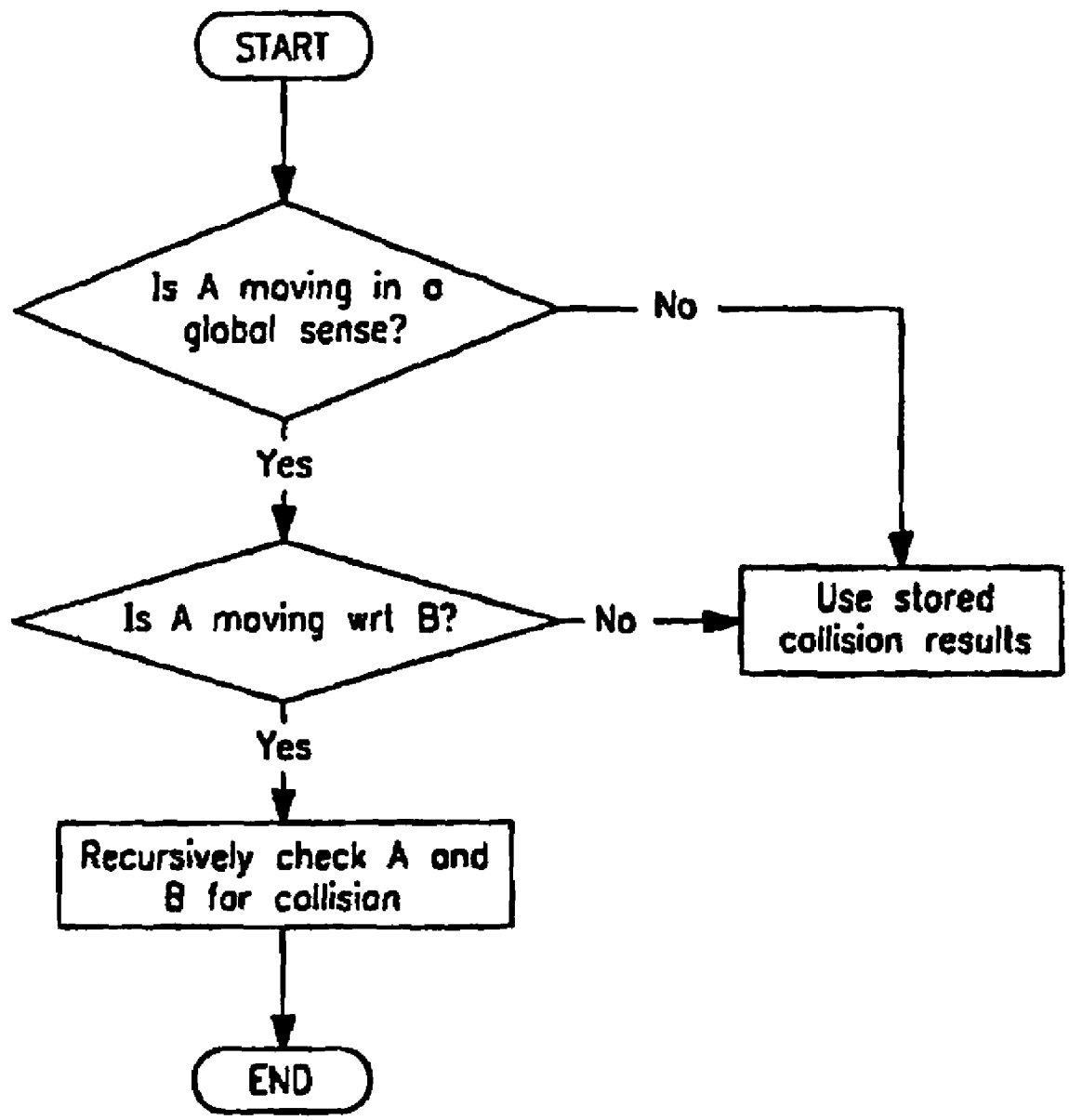
FIG. 9C is a flow chart illustrating steps for providing additional motion information to the collision detection process.

Moreover, the triangles in the model which are not required for collision data may also be specifically excluded from consideration when building an OBB tree. As depicted in FIG. 9C, additional information is provided to the collision algorithm to specify objects in motion. Motion may be viewed at two levels. Objects may be conceptualized as "moving" in a global sense, or they may be conceptualized as "moving" relative to other objects. The additional information improves the time taken for the collision detection by avoiding recomputation of collision information between objects which are at rest relative to each other since the state of the collision between such objects does not change.

Figure 18:
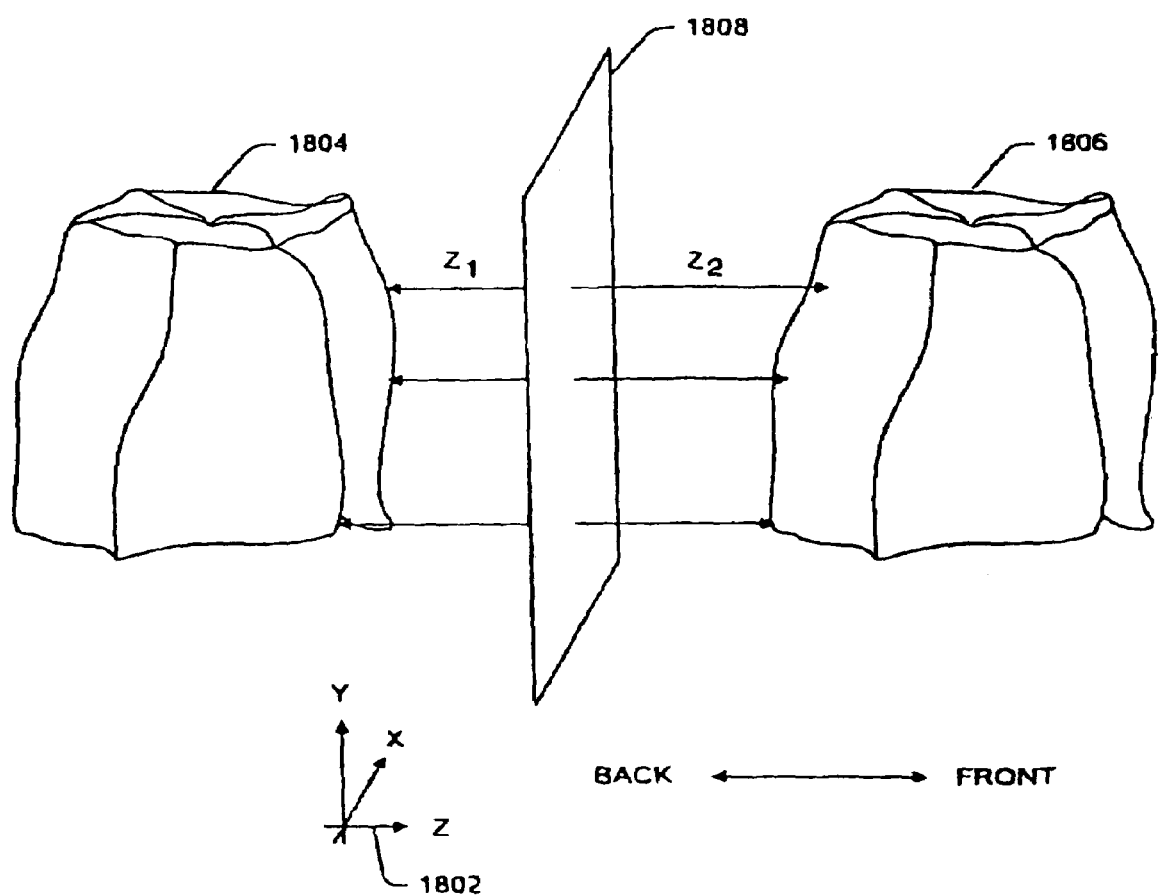
FIG. 18 is a diagram illustrating a buffering technique for use in a collision detection algorithm.

FIG. 18 illustrates an alternative collision detection scheme, one which calculates a "collision buffer" oriented along a z-axis 1802 along which two teeth 1804, 1806 lie. The collision buffer is calculated for each treatment step or at each position along a treatment path for which collision detection is required. To create the buffer, an x,y plane 1808 is defined between the teeth 1804, 1806. The plane must be "neutral" with respect to the two teeth. Ideally, the neutral plane is positioned so that it does not intersect either tooth. If intersection with one or both teeth is inevitable, the neutral plane is oriented such that the teeth lie, as much as possible, on opposite sides of the plane. In other words, the neutral plane minimizes the amount of each tooth's surface area that lies on the same side of the plane as the other tooth.

In the plane 1808 is a grid of discrete points. the resolution of which depends upon the required resolution for the collision detection routine. A typical high-resolution collision buffer includes a 400×400 grid; a typical low-resolution buffer includes a 20×20 grid. The z-axis 1802 is defined by a line normal to the plane 1808.

The relative positions of the teeth 1804, 1806 are determined by calculating, for each of the points in the grid, the linear distance parallel to the z-axis 1802 between the plane 1808 and the nearest surface of each tooth 1804, 1806. For example, at any given grid point (M,N), the plane 1808 and the nearest surface of the rear tooth 1804 are separated by a distance represented by the value $Z_{1(M,N)}$ while the plane 1808 and the nearest surface of the front tooth 1806 are separated by a distance represented by the value $Z_{2(M,N)}$. If the collision buffer is defined such that the plane 1808 lies at z=0 and positive values of z lie toward the back tooth 1804, then the teeth 1804, 1806 collide when $Z_{1(M,N)} \leq Z_{2(M,N)}$ at any grid point (MN) on the plane 1808.

Figure 19:
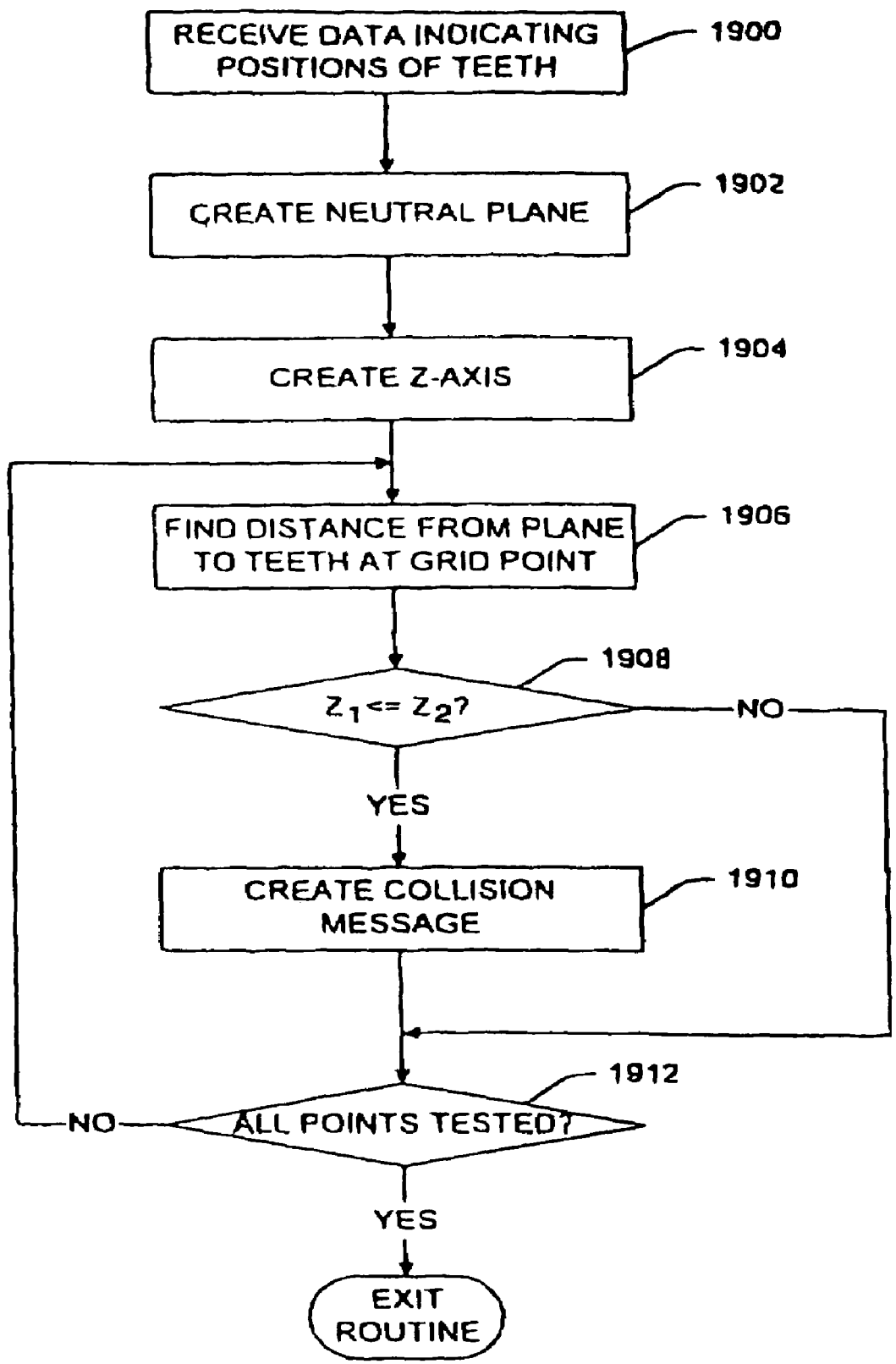
FIG. 19 is a flow chart for a collision detection technique.

FIG. 19 is a flow chart of a collision detection routine implementing this collision buffer scheme. The routine first receives data from one of the digital data sets indicating the positions of the surfaces of the teeth to be tested (step 1900). The routine then defines the neutral x,y-plane (step 1902) and creates the z-axis normal to the plane (step 1904).

The routine then determines for the x,y-position of the first grid point on the plane the linear distance in the z-direction between the plane and the nearest surface of each tooth (step 1906). To detect a collision at that x,y-position, the routine determines whether the z-position of the nearest surface of the rear tooth is less than or equal to the z-position of the nearest surface of the front tooth (step 1908). If so, the routine creates an error message, for display to a user or for feedback to the path-generating program, indicating that a collision will occur (step 1910). The routine then determines whether it has tested all x,y-positions associated with grid points on the plane (step 1912) and, if not, repeats the steps above for each remaining grid point. The collision detection routine is performed for each pair of adjacent teeth in the patient's mouth at each treatment step.

Incorporating a Model of an Orthodontic Appliance

Above-mentioned U.S. application Ser. No. 09/169,034; describes an appliance modeling system that implements techniques for modeling the interaction of the patient's teeth with orthodontic appliances, designed to cam-out the patient's treatment plan. Finite element analysis is used to determine the appliance configurations required to move the patient's teeth to the desired final positions along the prescribed treatment paths. In some situations, the appliance modeling system may determine that the desired tooth movement cannot be performed within constraints that are orthodontically acceptable or with an appliance that is manufacturable. The appliance modeling system therefore may determine that a tooth attachment should be added to the model or that the treatment plan should be modified. In these situations, feedback from the appliance modeling system is used to modify the geometric tooth models and the treatment plan accordingly.

Displaying the Treatment Plan Graphically

The system may also incorporate and the user may at any point use a "movie" feature to show an animation of the movement from initial to target states. This is helpful for visualizing overall component movement throughout the treatment process.

As described above, one suitable user interface for component identification is a three dimensional interactive graphical user interface (GUI). A three-dimensional GUI is also advantageous for component manipulation. Such an interface provides the treating professional or user with instant and visual interaction with the digital model components. The three dimensional GUI provides advantages over interfaces that permit only simple low-level commands for directing the computer to manipulate a particular segment. In other words, a GUI adapted for manipulation is better in many ways than an interface that accepts directives, for example, only of the sort: "translate this component by 0.1 mm to the right." Such low-level commands are useful for fine-tuning, but, if they were the sole interface, the processes of component manipulation would become a tiresome and time-consuming interaction.

Before or during the manipulation process, one or more tooth components may be augmented with template models of tooth roots. Manipulation of a tooth model augmented with a root template is useful, for example, in situations where impacting of teeth below the gumline is a concern. These template models could, for example, comprise a digitized representation of the patient's teeth x-rays.

The software also allows for adding annotations to the data sets which can comprise text and/or the sequence number of the apparatus. The annotation is added as recessed text (i.e., it is 3-D geometry), so that it will appear on the printed positive model. If the annotation can be placed on a part of the mouth that will be covered by a repositioning appliance, but is unimportant for the tooth motion, the annotation may appear on the delivered repositioning appliance(s).

The above-described component identification and component manipulation software is designed to operate at a sophistication commensurate with the operator's training level. For example, the component manipulation software can assist a computer operator, lacking orthodontic training, by providing feedback regarding permissible and forbidden manipulations of the teeth. On the other hand, an orthodontist, having greater skill in intraoral physiology and teeth-moving dynamics, can simply use the component identification and manipulation software as a tool and disable or otherwise ignore the advice.

Figure 20:
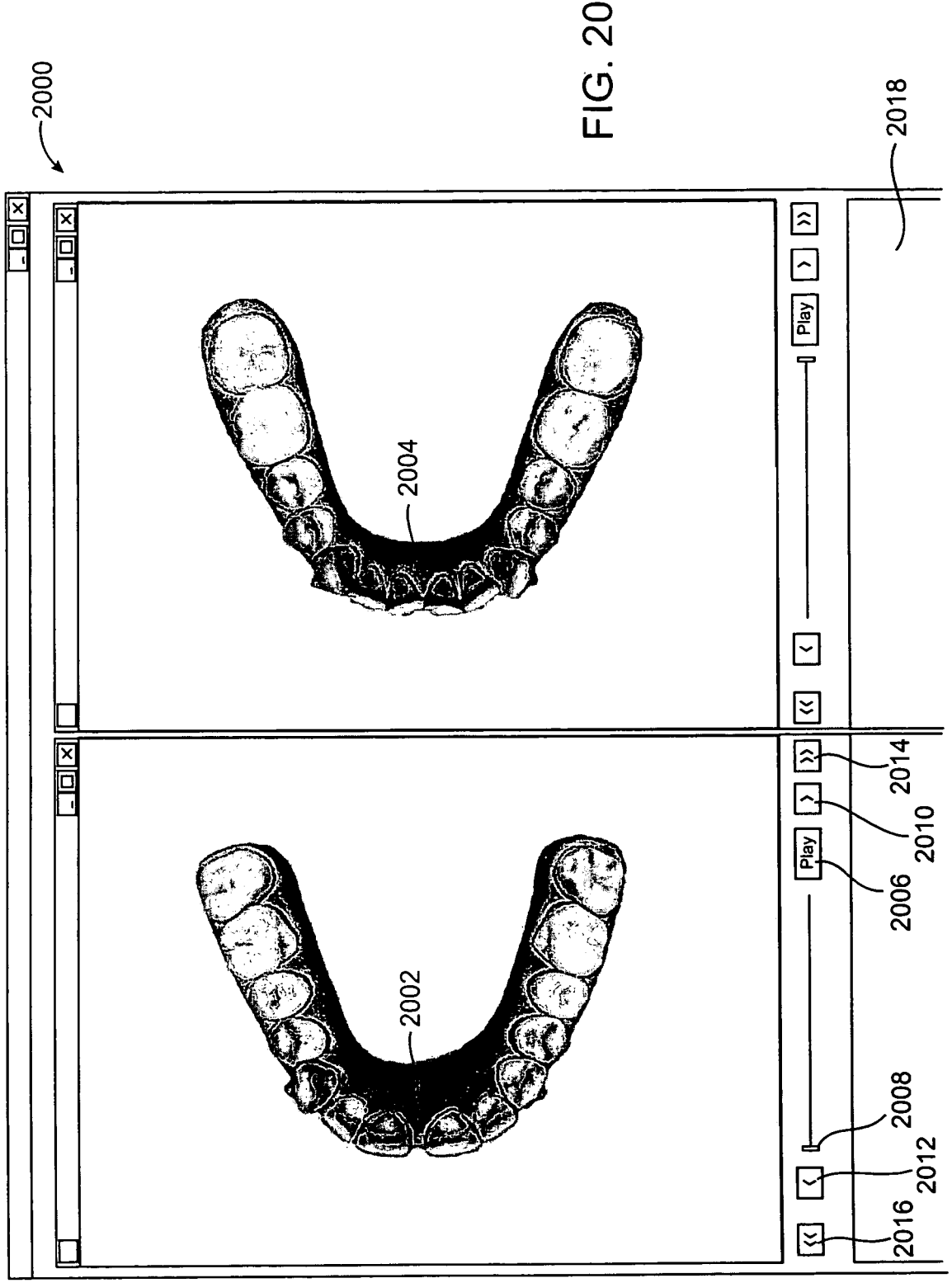
FIG. 20 is a screen shot of a GUI display used to render 3D images of an orthodontic patient's teeth.

FIG. 20 is a screen shot of the graphical user interface 2000 associated with a client viewer application through which a treating clinician is able to view a patient's treatment plan and alter or comment on the plan. The client viewer application is implemented in a computer program installed locally on a client computer at the clinician's site. The viewer program downloads a data file from a remote host, such as a, file transfer protocol (FTP) server maintained by the treatment plan designer, which can be accessed either through direct connection or through a computer network, such as the World Wide Web. The viewer program uses the downloaded file to present the treatment plan graphically to the clinician. The viewer program also can be used by the treatment plan designer at the host site to view images of a patient's teeth.

The data downloaded by the viewer program contains a fixed subset of key treatment positions, including the IDDS and the FDDS, that define the treatment plan for the patient's teeth. The viewer program renders the IDDS or the FDDS to display an image of the patient's teeth at the initial and final positions. The viewer program can display an image of the teeth at their initial positions (initial image 2002) and the final tooth positions (final image 2004) concurrently.

Because the data file contains a large amount of data, the download software in the remote host employs a "level-of-detail" technique to organize the download into data groups with progressively increasing levels of detail, as described below. The viewer program uses knowledge of orthodontic relevance to render less important areas of the image at a lower quality than it renders the more important areas. Use of these techniques reduces the time required to generate a single rendered image of the tooth models and the time required to display a rendered image on the screen after the download has begun.

Figure 21A:
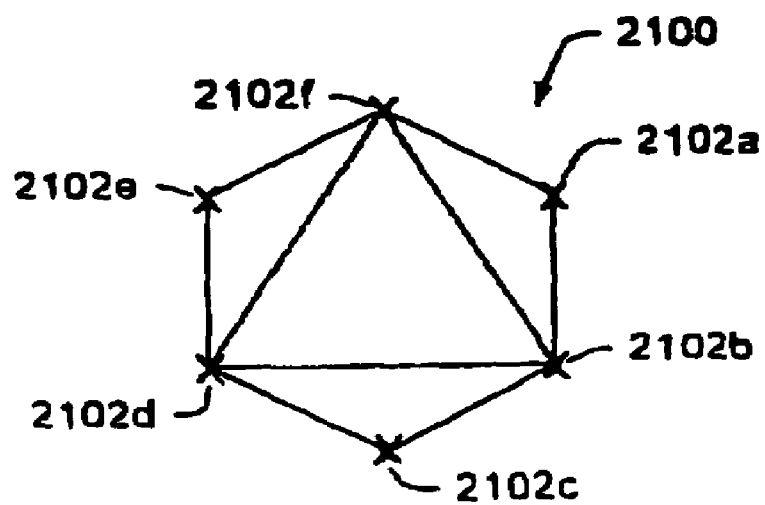
FIGS. 21A and 21B illustrate a technique for improving the downloading and rendering speed of an orthodontic image data file.
Figure 21B:
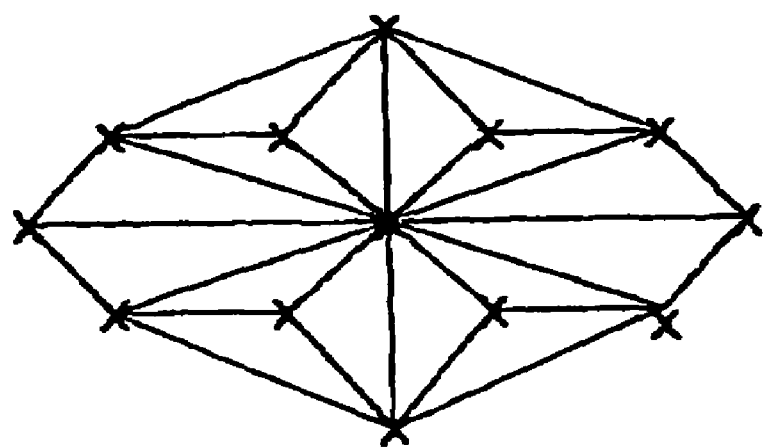

FIGS. 21A and 21B illustrate the use of the "level-of-detail" technique by the download software in the remote host. The software transfers the data in several groups, each of which adds detail incrementally for the rendered image of the teeth. The first group typically includes just enough data to render a rough polygon representation of the patient's teeth. For example, if a tooth is treated as a cube having six faces, the tooth can be rendered quickly as a diamond 2100 having six points 2102a–f, one lying in each face of the cube (FIG. 21A). The download software begins the download by delivering a few points for each tooth, which the interface program uses to render polygon representations of the teeth immediately.

The download software then delivers a second data group that adds additional detail to the rendered images of the teeth. This group typically adds points that allow a spheroid representation 2106 of the teeth (FIG. 21B). As the download continues, the software delivers additional groups of data, each adding a level of detail to the rendered image of the teeth, until the teeth are fully rendered.

The download software also improves download and rendering speed by identifying and, withholding data that is not critical to forming a rendered image of the teeth. This includes data for tooth surfaces obscured by other teeth or by tissue. The software applies rules based on common orthodontic structure to determine which data is downloaded and which is withheld. Withholding data in this manner reduces the size of the downloaded file and therefore reduces the number of data points that the interface program must take into account when rendering the initial and final images.

The viewer program also improves rendering speed by reducing the amount of data rendered. Like the download software, the viewer program applies rules of orthodontic relevance to determine which areas of the image can be rendered at lower quality. For example, the treating clinician usually does not want to view gum tissue in detail, so the viewer program renders the gums at low resolution as smooth surfaces, ignoring data that preserves the texture of the gums. Typically. the viewer program renders the less important areas at lower resolution before rendering the more important areas at higher resolution. The clinician can request high resolution rendering of the entire image.

As shown in FIG. 20 and discussed above, the viewer program displays an initial image 2002 of the teeth and, if requested by the clinician, a final image 2004 of the teeth as they will appear after treatment. The clinician can rotate the images in three dimensions to view the various tooth surfaces, and the clinician can snap the image to any of several predefined viewing angles. These viewing angles include the standard front, back, top, bottom and side views, as well as orthodontic-specific viewing angles, such as the lingual, buccal, facial, occlusal, and incisal views.

The viewer program also includes an animation routine that provides a series of images showing the positions of the teeth at each intermediate step along the treatment path. The clinician controls the animation routine through a VCR metaphor, which provides control buttons similar to those on a conventional video cassette recorder. In particular, the VCR metaphor includes a "play" button 2006 that, when selected, causes the animation routine to step through all of the images along the treatment path. A slide bar 2008 moves horizontally a predetermined distance with each successive image, displayed. Each position of the slide bar 2008 and each image in the series corresponds to one of the intermediate treatment steps described above.

The VCR metaphor also includes a "step forward" button 2010 and a "step back" button 2012, which allow the clinician to step forward or backward through the series of images, one key frame or treatment step at a time, as well as a "fast forward" button 2014 and a "fast back" button 2016, which allow the clinician to jump immediately to the final image 2004 or initial image 2002, respectively. The clinician also can step immediately to any image in the series by positioning the slide bar 2008 at the appropriate location.

As described above, the viewer program receives a fixed subset of key positions, including the IDDS and the FDDS, from the remote host. From this data, the animation routine derives the transformation curves required to display the teeth at the intermediate treatment steps, using any of a variety of mathematical techniques. One technique is by invoking the path-generation program described above. In this situation, the viewer program includes the path-generation program code. The animation routine invokes this code either when the downloaded key positions are first received or when the user invokes the animation routine.

The viewer program allows the clinician to alter the rendered image by manipulating the image graphically. For example, the clinician can reposition an individual tooth by using a mouse to click and drag or rotate the tooth to a desired position. In some implementations, repositioning an individual tooth alters only the rendered image; in other implementations, repositioning a tooth in this manner modifies the underlying data set. In the latter situation, the viewer program performs collision detection to determine whether the attempted alteration is valid and, if not, notifies the clinician immediately. Alternatively, the viewer program modifies the underlying data set and then uploads the altered data set to the remote host, which performs the collision detection algorithm. The clinician also can provide textual feedback to the remote host through a dialog box 2018 in the interface display 2000. Text entered into the dialog box 2018 is stored as a text object and later uploaded to the remote host or, alternatively, is delivered to the remote host immediately via an existing connection.

The viewer program optionally allows the clinician to isolate the image of a particular tooth and view the tooth apart from the other teeth. The clinician also can change the color of an individual tooth or group of teeth in a single rendered image or across the series of images. These features give the clinician a better understanding of the behavior of individual teeth during the course of treatment.

Another feature of the viewer program allows the clinician to receive information about a specific tooth or a specific part of the model upon command, e.g., by selecting the area of interest with a mouse. The types of information available include tooth type, distance between adjacent teeth, and forces (magnitudes and directions) exerted on the teeth by the aligner or by other teeth. Finite element analysis techniques are used to calculate the forces exerted on the teeth. The clinician also can request graphical displays of certain information, such as a plot of the forces exerted on a tooth throughout the course of treatment or a chart showing the movements that a tooth will make between steps on the treatment path. The viewer program also optionally includes "virtual calipers," a graphical tool that allows the clinician to select two points on the rendered image and receive a display indicating the distance between the points.

Fabricating the Aligners

Figure 10:
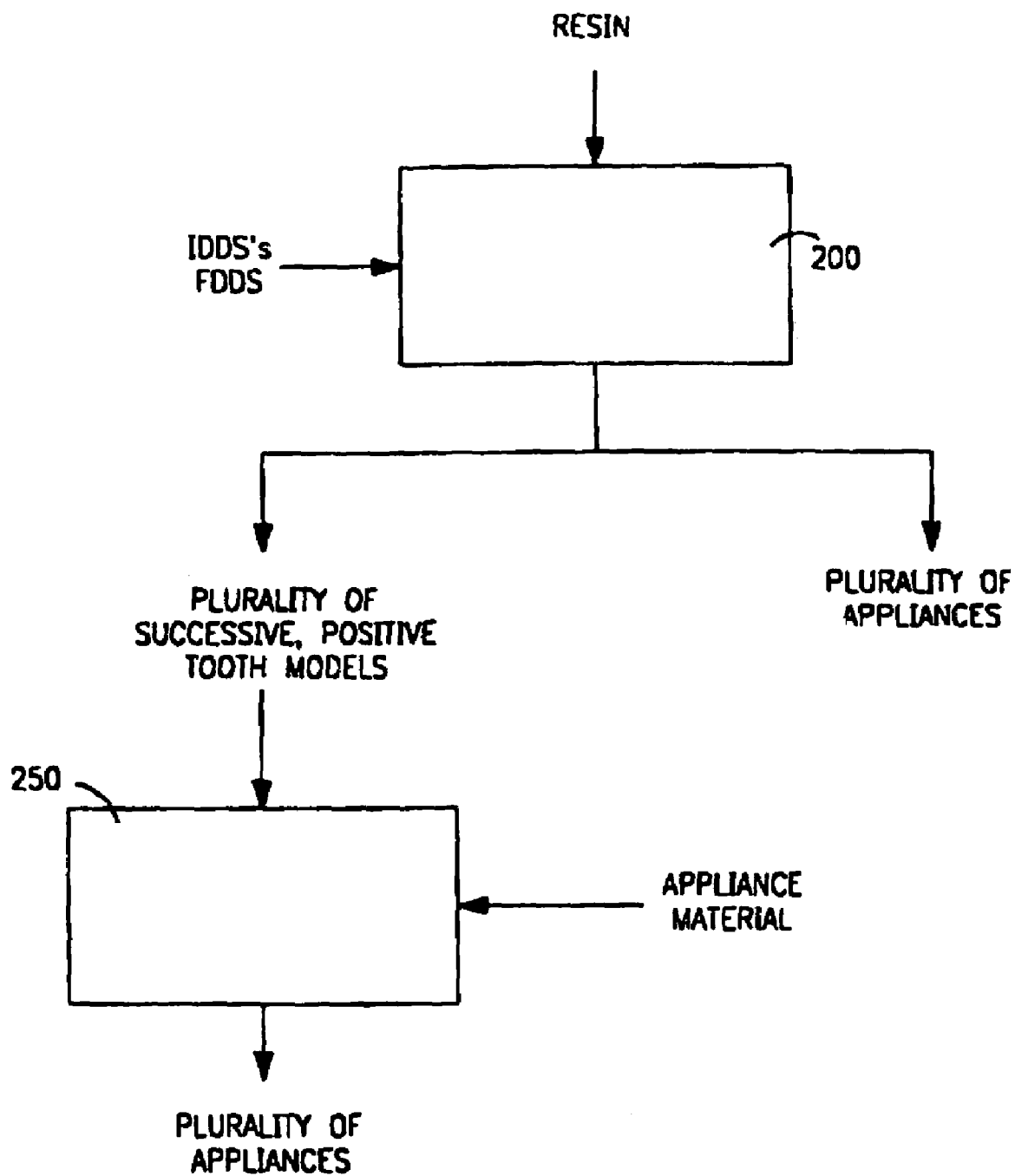
FIG. 10 illustrates alternative processes for producing a plurality of appliances utilizing digital data sets representing the intermediate and final appliance designs.

Once the intermediate and final data sets have been created, the appliances may be fabricated as illustrated in FIG. 10. Common fabrication methods employ a rapid prototyping device 200 such as a stereolithography machine. A particularly suitable rapid prototyping machine is Model SLA-250/50 available from 3D System, Valencia, Calif. The rapid prototyping machine 200 selectively hardens a liquid or other non-hardened resin into a three-dimensional structure which can be separated from the remaining non-hardened resin, washed, and used either directly as the appliance or indirectly as a mold for producing the appliance. The prototyping machine 200 receives the individual digital data sets and produces one structure corresponding to each of the desired appliances. Generally, because the rapid prototyping machine 200 may utilize a resin having non-optimum mechanical properties and which may not be generally acceptable for patient use, the prototyping machine typically is used to produce molds which are, in effect, positive tooth models of each successive stage of the treatment. After the positive models are prepared, a conventional pressure or vacuum molding machine is used to produce the appliances from a more suitable material, such as 0.03 inch thermal forming dental material, available from Tru-Tain Plastics, Rochester, Minn. 55902. Suitable pressure molding equipment is available under the trade name BIOSTAR from Great Lakes Orthodontics, Ltd., Tonawanda, N.Y. 14150. The molding machine 250 produces each of the appliances directly from the positive tooth model and the desired material. Suitable vacuum molding machines are available from Raintree Essix, Inc.

After production, the appliances can be supplied to the treating professional all at one time. The appliances are marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Because a patient's teeth may respond differently than originally expected, the treating clinician may wish to evaluate the patient's progress during the course of treatment. The system can also do this automatically, starting from the newly-measured in-course dentition. If the patient's teeth do not progress as planned, the clinician can revise the treatment plan as necessary to bring the patient's treatment back on course or to design an alternative treatment plan. The clinician may provide comments, oral or written, for use in revising the treatment plan. The clinician also can form another set of plaster castings of the patient's teeth for digital imaging and manipulation. The clinician may wish to limit initial aligner production to only a few aligners, delaying production on subsequent aligners until the patient's progress has been evaluated.

Figure 11:
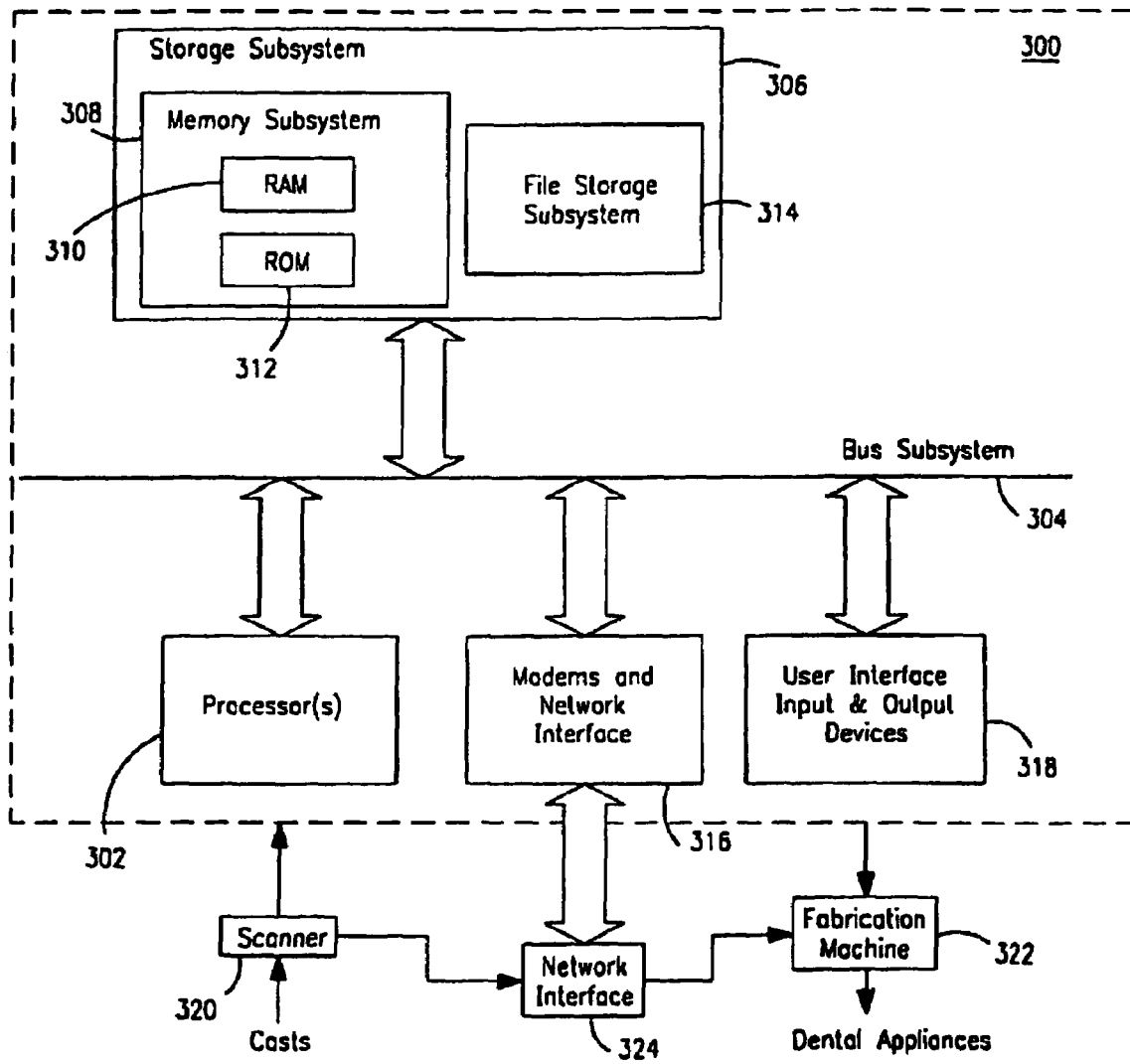
FIG. 11 is a simplified block diagram of a data processing system.

FIG. 11 is a simplified block diagram of a data processing system 300 that may be used to develop orthodontic treatment plans. The data processing system 300 typically includes at least one processor 302 which communicates with a number of peripheral devices via bus subsystem 304. These peripheral devices typically include a storage subsystem 306 (memory subsystem 308 and file storage subsystem 314), a set of user interface input and output devices 318, and an interface to outside networks 316, including the public switched telephone network. This interface is shown schematically as "Modems and Network Interface" block 316, and is coupled to corresponding interface devices in other data processing systems via communication network interface 324. Data processing system 300 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display, or a three dimensional pointing device, such as the gyroscopic pointing device described in U.S. Pat. No. 5,440,326, other types of user interface input devices, such as voice recognition systems, can also be used.

User interface output devices typically include a printer and a display subsystem, which includes a display controller and a display device coupled to the controller. The display device may be a cathode ray tube (CRT), a flat-panel de-ice such as a liquid crystal display (LCD), or a projection device. The display subsystem may also provide non-visual display such as audio output.

Storage subsystem 306 maintains the basic required programming and data constructs. The program modules discussed above are typically stored in storage subsystem 306. Storage subsystem 306 typically comprises memory subsystem 308 and file storage subsystem 314.

Memory subsystem 308 typically includes a number of memories including a main random access memory (RAM) 310 for storage of instructions and data during program execution and a read only memory (ROM) 312 in which fixed instructions are stored. In the case of Macintosh-compatible personal computers the ROM would include portions of the operating system; in the case of IBM-compatible personal computers, this would include the BIOS (basic input/output system).

File storage subsystem 314 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example. portions of the file storage system could be connected via various local-area or wide-area network media, including telephone lines. Similarly, the input devices and display need not be at the same location as the processor, although it is anticipated that personal computers and workstations typically will be used.

Bus subsystem 304 is shown schematically as a single bus, but a typical system has a number of buses such as a local bus and one or more expansion buses (e.g., ADB, SCSI, ISA, EISA. MICA, NuBus, or PCI), as well as serial and parallel ports. Network connections are usually established through a device such as a network adapter on one of these expansion buses or a modem on a serial port. The client computer may be a desktop system or a portable system.

Scanner 320 is responsible for scanning casts of the patient's teeth obtained either from the patient or from an orthodontist and providing the scanned digital data set information to data processing system 300 for further processing. In a distributed environment, scanner 320 may be located at a remote location and communicate scanned digital data set information to data processing system 300 via network interface 324.

Fabrication machine 322 fabricates dental appliances based on intermediate and final data set information received from data processing system 300. In a distributed environment, fabrication machine 322 may be located at a remote location and receive data set information from data processing system 300 via network interface 324.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly. Moreover, the tooth models may be posted on a hypertext transfer protocol (http) web site for limited access by the corresponding patients and treating clinicians Many alterations and modifications may be made by those of ordinary skill in this art, without departing from the spirit and scope of this invention. The illustrated embodiments have been shown only for purposes of clarity and the examples should not be taken as limiting the invention as defined in the following claims. Which claims are intended to include all equivalents, whether now or later devised.

What is claimed is:

1. A computer-implemented method for use in creating a treatment plan to reposition a patient's teeth from a set of initial tooth positions to a set of final tooth positions, the method comprising:
   receiving an initial digital data set representing the teeth at the initial positions, wherein receiving the initial digital data set comprises receiving data obtained by scanning the patient's teeth or a physical model thereof;
   generating a set of intermediate positions toward which the teeth will move while moving from the initial positions toward the final positions; and
   generating a plurality of successive appliances having cavities and wherein the cavities of successive appliances have different geometries shaped to receive and reposition teeth from the initial positions toward the final positions,
   wherein the plurality of successive appliances is generated at a stage of treatment prior to the patient wearing any appliance of said plurality so as to reposition the teeth.

2. The method of claim 1, wherein receiving the initial digital data set comprises receiving data obtained by scanning a physical model of the patient's teeth.

3. The method of claim 2, further comprising scanning the physical model with a destructive scanning system.

4. The method of claim 3, further comprising scanning the physical model with a laser scanning system before scanning the model with the destructive scanning system.

5. The method of claim 2, further comprising scanning physical models of the patient's upper and lower teeth in occlusion.

6. The method of claim 5, wherein scanning the physical models of the patient's upper and lower teeth comprises scanning the physical models with a laser scanning system.

7. The method of claim 2, wherein receiving the initial data set includes receiving image data obtained directly by imaging the patient's teeth.

8. The method of claim 7, wherein the image data is digital.

9. The method of claim 7, wherein the image data includes at least one of the following: 2D x-ray data, 3D x-ray data, CT scan data, and MRI data.

10. The method of claim 2, further comprising analyzing the data obtained by scanning the physical model to determine physical characteristics of a material used in the model.

11. The method of claim 1, wherein receiving the initial digital data set comprises receiving data obtained by scanning two physical models of the patient's teeth, one representing a positive impression of the teeth and one representing a negative impression of the teeth.

12. The method of claim 11, further comprising scanning the positive impression and the negative impression while interlocked with each other.

13. The method of claim 1, wherein the initial digital data set includes volume image data of the patient's teeth and the method includes converting the volume image data into a 3D geometric model of the tooth surfaces.

14. The method of claim 13, wherein converting the volume image data comprises detecting volume elements in the image data between which a large transition in image value occurs.

15. The method of claim 1, further comprising applying a set of predefined rules to segment the initial data set into 3D models of individual dentition components of the patient's mouth.

16. The method of claim 15, further comprising deriving the rules from a database of information indicating how a typical data set is segmented into individual tooth models.

17. The method of claim 15, wherein the rules include information about the cusp structure of typical teeth.

18. The method of claim 15, wherein one of the dentition components comprises at least a portion of an individual tooth.

19. The method of claim 15, wherein one of the dentition components comprises gum in the patient's mouth.

20. The method of claim 15, wherein applying the set of predetermined rules comprises applying a rule for recognizing noise in a tooth cast from which the initial data set is derived.

21. The method of claim 1, further comprising applying rules of orthodontic relevance to reduce the amount of data in the initial data set associated with less important orthodontic features.

22. The method of claim 1, further comprising modifying the initial data set to include data representing a hidden tooth surface.

23. The method of claim 22, wherein the hidden tooth surfaces include tooth roots.

24. The method of claim 22, wherein the data representing the hidden tooth surfaces comprises image data representing the hidden surfaces of the patient's teeth.

25. The method of claim 24, wherein the image data comprises at least one of the following: X-ray data, CT scan data, MRI data.

26. The method of claim 22, wherein the data representing the hidden tooth surfaces comprises data representing the hidden surfaces of typical teeth.

27. The method of claim 22, further comprising extrapolating visible surfaces of the patient's teeth to derive the data representing the hidden tooth surfaces.

28. The method of claim 22, further comprising:
receiving image data containing an image of the patient's teeth;
analyzing the image data to identify a particular feature of at least one of the patient's teeth; and
using the identified feature to guide the inclusion of the hidden tooth surface.

29. The method of claim 28, wherein the image data is digital.

30. The method of claim 28, wherein the image data comprises at least one of the following: 2D x-ray data, 3D x-ray data, CT scan data, and MRI data.

31. The method of claim 1, further comprising receiving information indicating whether the patient's teeth are moving as planned and, if not, using the information to revise the set of intermediate positions.

32. The method of claim 1, wherein generating the set of intermediate positions comprises generating more than one candidate set of intermediate position for each tooth and providing a graphical display of each candidate set to a human user for selection.

33. The method of claim 1, further comprising applying a set of rules to detect any collisions that will occur between teeth as the patient's teeth move toward the set of final positions.

34. The method of claim 33, wherein detecting collisions comprises calculating distances between a first tooth and a second tooth by:
establishing a neutral projection plane between the first tooth and the second tooth,
establishing a z-axis that is normal to the plane and that has a positive direction and a negative direction from each of a set of base points on the projection plane,
computing a pair of signed distances comprising a first signed distance to the first tooth and a second signed distance to the second tooth, the signed distances being measured on a line through the base points and parallel to the z-axis, and
determining that a collision occurs if any of the pair of signed distances indicates a collision.

35. The method of claim 34, wherein the positive direction for the first distance is opposite the positive direction for the second distance and a collision is detected if the sum of any pair of signed distances is less than or equal to zero.

36. The method of claim 1, further comprising applying a set of rules to detect any improper bite occlusions that will occur as the patient's teeth move toward the set of final positions.

37. The method of claim 36, further comprising calculating a value for a malocclusion index and displaying the value to a human user.

38. The method of claim 1, wherein generating the set of intermediate positions includes receiving data indicating restraints on movement of the patient's teeth and applying the data to generate the intermediate positions.

39. The method of claim 1, wherein generating the set of intermediate positions includes determining the minimum amount of transformation required to move each tooth from the initial position toward the final position and creating the intermediate positions to require the minimum amount of movement.

40. The method of claim 39, wherein each set of intermediate positions is created to require, in addition to the minimum amount of movement, any movement that is needed to satisfy an orthodontic restraint that applies to the corresponding tooth.

41. The method of claim 1, wherein generating the set of intermediate positions includes generating intermediate positions for at least one tooth between which the tooth undergoes translational movements of equal sizes.

42. The method of claim 1, further comprising rendering a representation of the teeth at the set of positions corresponding to a selected data set.

43. The method of claim 42, further comprising using only a portion of the data in the selected data set to render the graphical representation of the teeth.

44. The method of claim 42, further comprising applying level-of-detail compression to the data set to render the graphical representation of the teeth.

45. The method of claim 42, further comprising receiving an instruction from a human user to modify the graphical representation of the teeth and modifying the graphical representation in response to the instruction.

46. The method of claim 45, further comprising modifying the selected data set in response to the instruction from the user.

47. The method of claim 42, further comprising allowing a human user to select a tooth in the graphical representation and, in response, displaying information about the tooth.

48. The method of claim 47, wherein the information relates to the forces that the tooth will experience while moving toward the set of final positions.

49. The method of claim 47, wherein the information indicates a linear distance between the tooth and another tooth selected in the graphical representation.

50. The method of claim 42, wherein rendering the graphical representation comprises rendering the teeth at a selected one of multiple viewing orthodontic-specific viewing angles.

51. The method of claim 42, further comprising providing a user interface through which a human user can provide text-based comments after viewing the graphical representation of the patient's teeth.

52. The method of claim 42, wherein rendering the graphical representation comprises downloading data to a remote computer.

53. The method of claim 42, further comprising receiving an input signal from a 3D input device controlled by a human user and using the input signal to alter the orientation of the teeth in the graphical representation.

54. The method of claim 53, wherein the 3D input device comprises a gyroscopic pointing device.

55. The method of claim 42, further comprising subsequently rendering a graphical representation of the teeth at the set of positions corresponding to another of the data sets to illustrate how the patient's teeth will move during treatment.

56. The method of claim 55, wherein the graphical representation includes a three dimensional representation of the teeth.

57. The method of claim 42, further comprising:
receiving data indicating two positions in the graphical representation that a user has selected with a pointing device;
calculating the distance between the two points; and
displaying the distance in the graphical representation.

58. The method of claim 42, wherein the representation includes a three-dimensional (3D) graphical representation of the teeth.

59. The method of claim 1, further comprising providing a user interface with an input component that allows a human user to control an animation of the movement of the teeth.

60. The method of claim 59, wherein the input components allow the user to take any of the following actions: view the animation at a normal frame rate, step through the animation one frame at a time, select a particular frame in the animation for viewing, and stop the animation.

61. The method of claim 59, wherein the user interface includes a graphical user interface.

62. The method of claim 1, further comprising delivering data identifying the intermediate treatment positions to an appliance fabrication system for use in fabricating at least one orthodontic appliance structured to move the patient's teeth toward the final positions.

63. The method of claim 62, further comprising including in the data a digital model of an orthodontic attachment that the appliance must accommodate.

64. The method of claim 63, wherein the digital model represents an attachment to be placed on one of the patient's teeth.

65. The method of claim 63, wherein the digital model represents an anchor to be placed in the patient's mouth and against which the appliance must pull.

66. The method of claim 62, further comprising receiving data indicating material properties of the appliance to be fabricated and using the data to generate the set of intermediate positions.

67. The method of claim 1, further comprising generating a final data set representing the teeth at the final positions.

68. The method of claim 1, further comprising generating a series of orthodontic devices for repositioning the patient's teeth from the initial positions to the final positions.

69. The method of claim 68, further comprising:
using the appliances to treat the patient's teeth;
receiving an in-course digital data set representing actual positions of the patient's teeth after treatment has begun; and
displaying a graphical representation of the patient's teeth at the actual positions.

70. The method of claim 1, further comprising generating treatment paths among the intermediate positions along which the teeth will move from the initial positions toward the final positions.

71. The method of claim 1, further comprising generating an alternative set of intermediate treatment positions.

72. The method of claim 71, further comprising displaying at least two different sets of intermediate treatment positions to a user and allowing the user to select one of the sets for use in treating the patient's teeth.

73. The method of claim 1, further comprising generating, for each tooth at each tooth position, a transformation representing a translational position of the tooth and a rotational position of the tooth with respect to an origin.

74. The method of claim 1, wherein generating the intermediate positions comprises representing the teeth in a configuration space.

75. The method of claim 1, further comprising generating a renderable model of the patient's teeth at the final positions.

76. The method of claim 75, further comprising making the renderable model available on a computer accessible by the treating clinician.

77. The method of claim 76, further comprising generating a graphical representation of the patient's teeth at the final positions when the clinician accesses the renderable model.

78. The method of claim 75, further comprising making the renderable model available on a computer accessible by the patient.

79. The method of claim 78, further comprising generating a graphical representation of the patient's teeth at the final positions when the patient accesses the renderable model.

80. The method of claim 1, wherein generating the intermediate treatment positions comprises receiving information about a material property of a device that will be used to treat the patient's teeth and deriving from the information a constraint on the movement of at least one of the teeth.

81. A computer program, residing on a tangible storage medium, for use in creating a treatment plan to reposition a patient's teeth from a set of initial tooth positions to a set of final tooth positions, the program comprising executable instructions operable to cause a computer to:
receive an initial digital data set representing the teeth at the initial positions, wherein receiving the initial digital data set comprises receiving data obtained by scanning the patient's teeth or a physical model thereof;
generate a set of intermediate positions toward which the teeth will move while moving from the initial positions toward the final positions, as to allow
generating a plurality of successive appliances having cavities and wherein the cavities of successive appliances have different geometries shaped to receive and reposition teeth from the initial positions toward the final positions,
wherein the plurality of appliances is generated at a stage of treatment prior to the patient wearing any appliance of said plurality so as to achieve repositioning of the teeth.

82. The program of claim 81, wherein the initial digital data set includes data obtained by scanning a physical model of the patient's teeth.

83. The program of claim 81, wherein the initial digital data set includes data obtained by scanning a positive impression and a negative impression of the patient's teeth interlocked together.

84. The program of claim 81, wherein the initial digital data set includes volume image data of the patient's teeth and the computer converts the volume image data into a 3D geometric model of the tooth surfaces by detecting volume elements in the image data between which a large transition in image value occurs.

85. The program of claim 81, wherein the computer applies a set of predefined rules to segment the initial data set into 3D models of the individual teeth.

86. The program of claim 81, wherein the computer modifies the initial digital data set to include data representing hidden tooth surfaces.

87. The program of claim 81, wherein the computer applies a set of rules to detect any collisions that will occur as the patient's teeth move toward the final positions.

88. The program of claim 87, the computer detects collisions by calculating distances between a first tooth and a second tooth by:
establishing a neutral projection plane between the first tooth and the second tooth,
establishing a z-axis that is normal to the plane and that has a positive direction and a negative direction from each of a set of base points on the projection plane,
computing a pair of signed distances comprising a first signed distance to the first tooth and a second signed distance to the second tooth, the signed distances being measured on a line through the base points and parallel to the z-axis, and
determining that a collision occurs if any of the pair of signed distances indicates a collision.

89. The method of claim 88, wherein the positive direction for the first distance is opposite the positive direction for the second distance and a collision is detected if the sum of any pair of signed distances is less than or equal to zero.

90. The program of claim 81, wherein the computer applies a set of rules to detect any improper bite occlusions that will occur as the patient's teeth move toward the final positions.

91. The program of claim 81, wherein the computer renders a 3D graphical representation of the teeth at the positions corresponding to a selected data set.

92. The program of claim 91, wherein the computer animates the graphical representation of the teeth to provide a visual display of the movement of the teeth toward the final positions.

93. The program of claim 81, wherein the computer applies level-of-detail compression to the selected data set to render the graphical representation of the teeth.

94. The program of claim 81, wherein the computer receives an instruction from a human user to modify the graphical representation of the teeth and, in response to the instruction, modifies the graphical representation and the selected data set.

95. The program of claim 81, wherein the computer delivers data identifying the intermediate treatment positions to an appliance fabrication system for use in fabricating at least one orthodontic appliance structured to move the patient's teeth toward the final positions.

96. The program of claim 95, wherein the computer includes in the data a digital model of an orthodontic attachment that the appliance must accommodate.

97. The program of claim 81, wherein the computer generates a final data set representing the teeth at the final positions.

98. The program of claim 81, wherein the computer generates data for use in creating a series of orthodontic devices for repositioning the patient's teeth from the initial positions to the final positions.

99. The program of claim 81, wherein the computer generates treatment paths among the intermediate positions along which the teeth will move from the initial positions toward the final positions.

* * * * *

UNITED STATES PATENT AND TRADEMARK OFFICE
CERTIFICATE OF CORRECTION

PATENT NO. : 7,134,874 B2 Page 1 of 1
APPLICATION NO. : 10/718779
DATED : November 14, 2006
INVENTOR(S) : Muhammad Chishti et al.

It is certified that error appears in the above-identified patent and that said Letters Patent is hereby corrected as shown below:

On the title page item (63), delete "Continuation of application No. 09/686,190, filed on Oct. 10, 2000, now abandoned, which is a continuation of application No. 09/169,276, filed on Oct. 8, 1998, now abandoned, which is a continuation-in-part of application No. PCT/US98/12681, filed on Jun. 19, 1998."

and insert -- This application is a continuation of U.S. application Ser. No. 09/686,190, filed Oct. 10, 2000, (now abandoned), which was a continuation of U.S. application Ser. No. 09/169,276, filed Oct. 8, 1998, (now abandoned), which is a continuation-in-part of PCT Application No. PCT/US98/12861, filed Jun. 19, 1998, which claims priority from U.S. patent application Ser. No. 08/947,080, filed Oct. 8, 1997 (now U.S. Pat. No. 5,975,893), which claims priority from U.S. Provisional Application No. 60/050,342, filed on Jun. 20, 1997, the full disclosures of which are incorporated in this application by reference. --

Column 1, lines 12-13, please delete "PCT/US/99/12691" and insert
-- PCT/US98/12861 --.

Signed and Sealed this

First Day of May, 2007

JON W. DUDAS
*Director of the United States Patent and Trademark Office*